(12) United States Patent
Jeong

(10) Patent No.: US 7,864,334 B2
(45) Date of Patent: Jan. 4, 2011

(54) INTERFEROMETRIC DEFECT DETECTION

(75) Inventor: Hwan J. Jeong, Los Altos, CA (US)

(73) Assignee: JZW LLC, Sunnyvale, CA (US)

( * ) Notice: Subject to any disclaimer, the term of this patent is extended or adjusted under 35 U.S.C. 154(b) by 291 days.

(21) Appl. No.: 12/190,144

(22) Filed: Aug. 12, 2008

(65) Prior Publication Data
US 2009/0296096 A1 Dec. 3, 2009

Related U.S. Application Data

(60) Provisional application No. 61/130,729, filed on Jun. 3, 2008, provisional application No. 61/135,616, filed on Jul. 22, 2008.

(51) Int. Cl.
*G01N 21/00* (2006.01)
*G01B 11/02* (2006.01)

(52) U.S. Cl. .................................... 356/496; 356/239.7

(58) Field of Classification Search ............. 356/237.1, 356/239.1, 239.7, 450, 496
See application file for complete search history.

(56) References Cited

U.S. PATENT DOCUMENTS

| | | | |
|---|---|---|---|
| 6,259,055 B1 | 7/2001 | Sokol et al. | |
| 6,501,551 B1 | 12/2002 | Tearney et al. | |
| 6,934,035 B2 | 8/2005 | Yang et al. | |
| 7,061,625 B1 | 6/2006 | Hwang et al. | |
| 7,095,507 B1 | 8/2006 | Hwang et al. | |
| 7,138,629 B2 | 11/2006 | Noji et al. | |
| 7,209,239 B2 | 4/2007 | Hwang et al. | |
| 7,259,869 B2 | 8/2007 | Hwang et al. | |
| 7,351,969 B2 | 4/2008 | Watanabe et al. | |
| 7,357,513 B2 | 4/2008 | Watson et al. | |
| 7,365,858 B2 | 4/2008 | Fang-Yen et al. | |
| 7,428,057 B2 * | 9/2008 | De Lega et al. | 356/511 |
| 7,446,882 B2 * | 11/2008 | De Lega et al. | 356/512 |
| 7,616,323 B2 * | 11/2009 | De Lega et al. | 356/511 |
| 2002/0066318 A1 * | 6/2002 | Dubois et al. | 73/579 |
| 2005/0105097 A1 | 5/2005 | Fang-Yen et al. | |
| 2006/0132804 A1 * | 6/2006 | Dubois et al. | 356/614 |
| 2006/0158657 A1 * | 7/2006 | De Lega et al. | 356/497 |
| 2006/0158658 A1 * | 7/2006 | Colonna De Lega et al. | 356/497 |
| 2006/0158659 A1 * | 7/2006 | Colonna De Lega et al. | 356/497 |
| 2006/0215174 A1 * | 9/2006 | Dubois et al. | 356/502 |
| 2008/0007726 A1 | 1/2008 | Fairley et al. | |
| 2008/0024766 A1 | 1/2008 | Mieher et al. | |
| 2008/0088849 A1 * | 4/2008 | De Lega et al. | 356/450 |

(Continued)

OTHER PUBLICATIONS

M. Francon, "Optical Interferometry," Academic Press, New York and London, 1966, p. 289.

(Continued)

*Primary Examiner*—Patrick J Connolly
(74) *Attorney, Agent, or Firm*—Cooper & Dunham, LLP

(57) ABSTRACT

Methods and systems for using common-path interferometry are described. In some embodiments, a common-path interferometry system for the detection of defects in a sample is described. An illumination source generates and directs coherent light toward the sample. An optical imaging system collects light reflected from the sample including a scattered component of that is predominantly scattered by the sample, and a specular component that is predominantly undiffracted by the sample. A variable phase controlling system is used to adjust the relative phase of the scattered component and the specular component so as to improve the ability to detect defects in the sample.

129 Claims, 36 Drawing Sheets

U.S. PATENT DOCUMENTS

2008/0221814 A1* 9/2008 Trainer .................. 702/70
2008/0266547 A1* 10/2008 Clark et al. ............... 356/73
2008/0291465 A1* 11/2008 Lorraine et al. ........... 356/502
2009/0296096 A1* 12/2009 Jeong .................... 356/450
2010/0134786 A1* 6/2010 De Lega et al. ........... 356/73

OTHER PUBLICATIONS

Philip C. D. Hobbs. "Building Electro-Optical Systems; Making it all work," John Wiley & Sons, Inc., 2000, pp. 30-32.

R. M. A. Azzam and N. M. Bashara, "Ellipsometry and Polarized Light" Elsevier Science B. V., 1999, pp. 72-84.

Aug. 5, 2009 International Search Report in connection with counterpart International Application No. PCT/US2009/045999.

Aug. 5, 2009 Notification of Transmittal of the International Search Report and the Written Opinion of the International Searching Authority, or the Declaration in connection with counterpart International Application No. PCT/US2009/045999.

Aug. 5, 2009 Written Opinion of the International Searching Authority in connection with counterpart International Application No. PCT/US2009/045999.

* cited by examiner

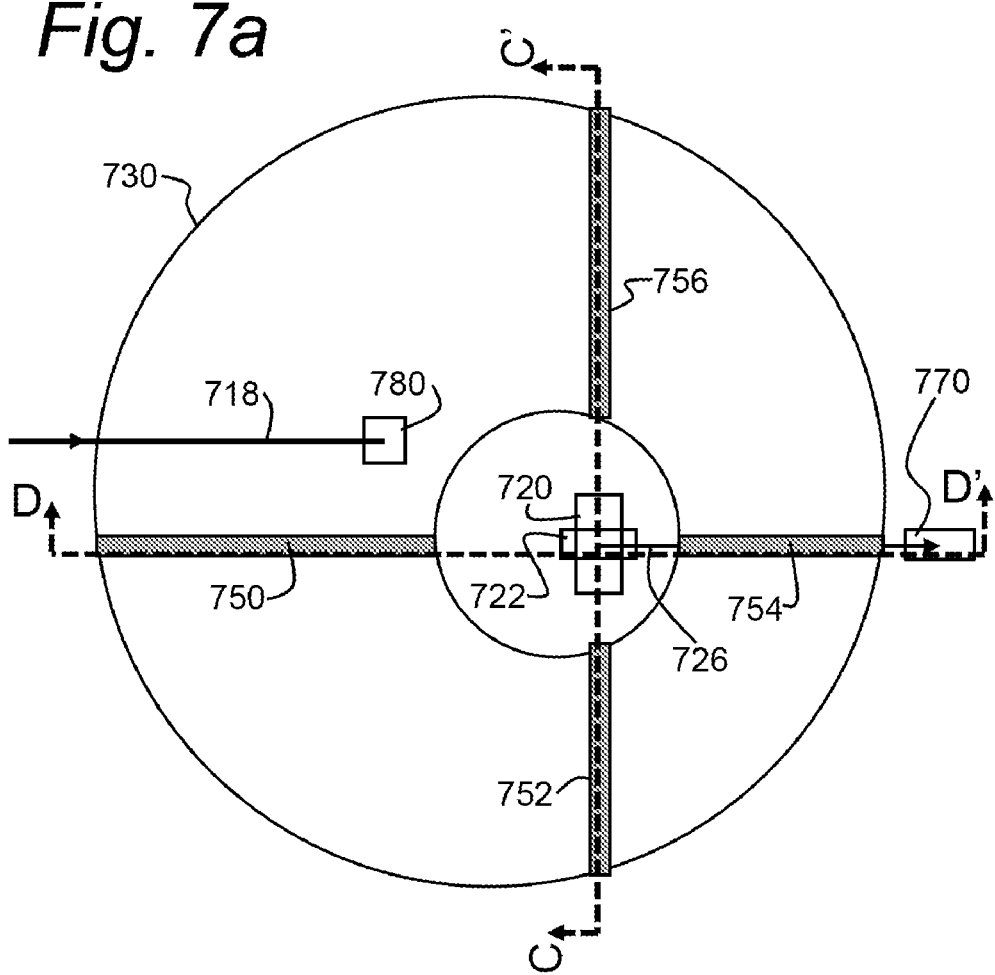
Fig. 7a
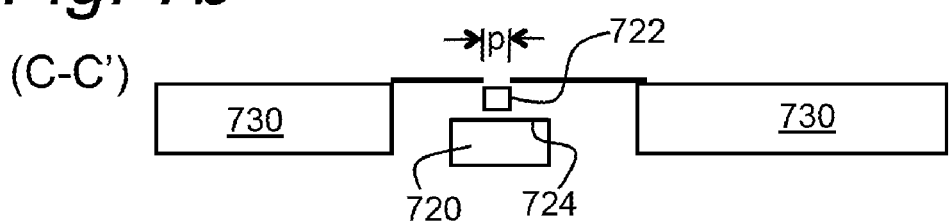
Fig. 7b (C-C')
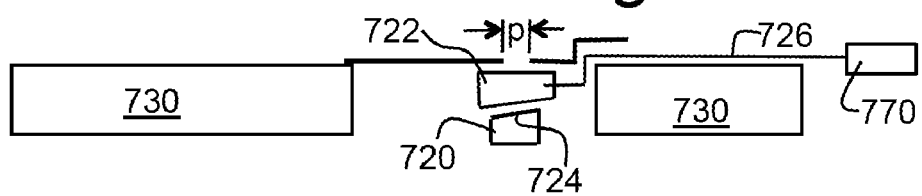
Fig. 7c (D-D')

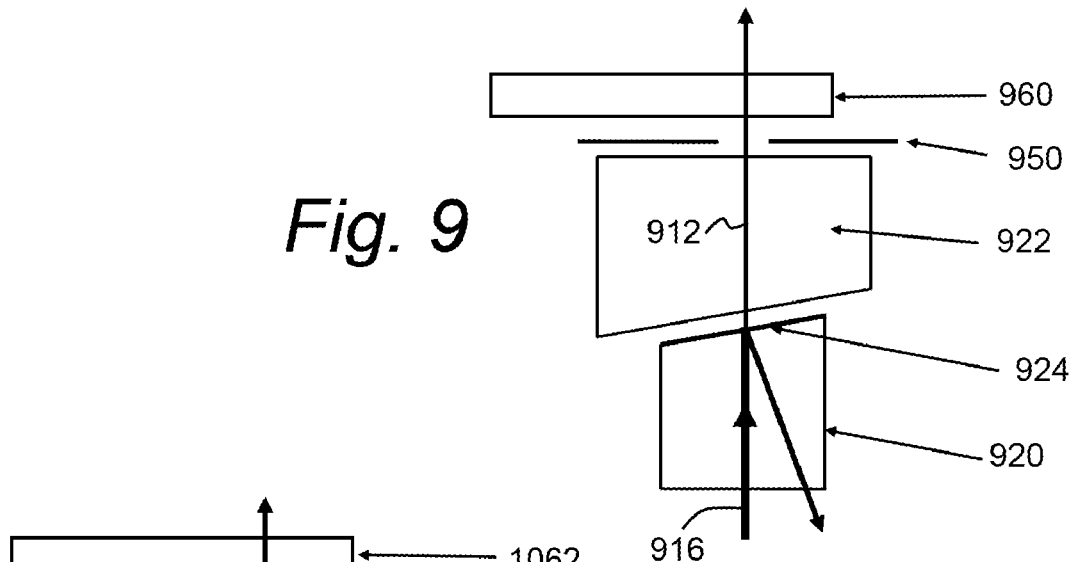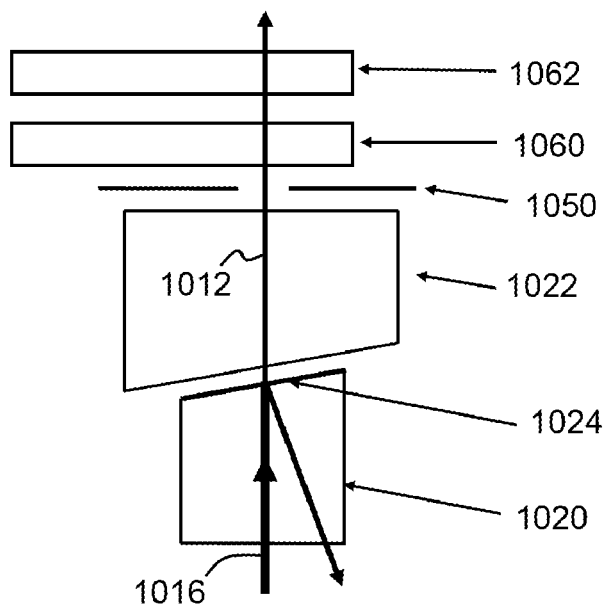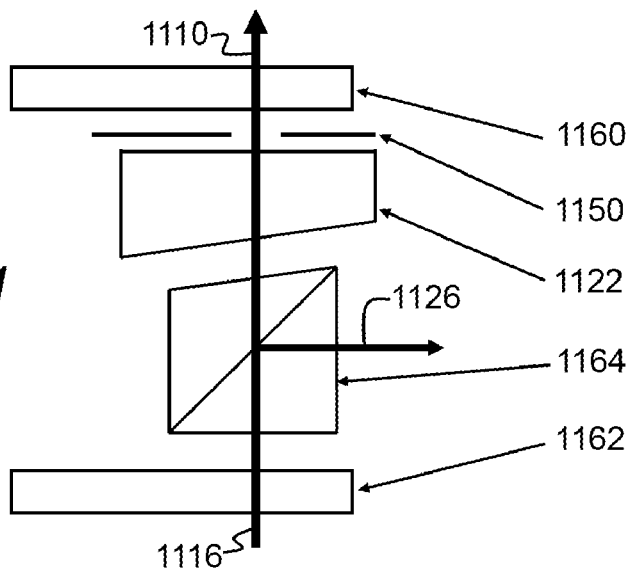

(E-E')

(F-F')

INTERFEROMETRIC DEFECT DETECTION

CROSS-REFERENCE TO RELATED APPLICATIONS

This patent claims the benefit of U.S. Provisional Ser. No. 61/130,729 filed Jun. 3, 2008, and of U.S. Provisional Ser. No. 61/135,616 filed Jul. 22, 2008, each of which is incorporated by reference herein.

FIELD

This patent specification relates to common-path interferometry. More particularly, the patent specification relates to high resolution common-path interferometry for use in detecting defects in microlithographic devices such as semiconductor devices and integrated circuits and defects in photolithographic reticles.

BACKGROUND

Optical defect detection technology has been the bread and butter for the detection of various kinds of defects in semiconductor wafers. It has provided both high performance and high throughput, which other technologies like electron beam microscopy could not offer. However, as the design rules of IC chips decreased, it became harder to detect defects reliably. Especially, design rules of future generations of IC chips are so small that there is a real possibility that none of the current optical defect detection technologies work. Therefore, in order to extend the life of optical technology into future generation systems of defect detection, a major overhaul of optical defect detection technology is needed.

Known optical defect detection systems include both bright field systems and dark field systems. Unlike bright field systems, dark field systems attempt to exclude the unscattered beam from the image. However, limitations of the current dark field and bright field defect detection systems exist which cause difficulty in accurately detecting defects especially as the design rules progressively decrease. Separate path interferometric techniques have been proposed according to which two beams, probe and reference beams, are generated using a beam splitter and brought to an image sensor through different paths or subsystems. For example, separate path systems designed for defect detection are described in U.S. Pat. Nos. 7,061,625, 7,095,507, 7,209,239 and 7,259,869. Another separate path system which is designed for high resolution surface profiling is Linnik interferometer (see, M. Francon, "Optical Interferometry," Academic Press, New York and London, 1966, p 289.) These separate path interferometric systems are, in principle, capable of amplifying the defect signal or measuring both the amplitude and phase of the defect signal. However, these systems are not only complex and expensive but also have a very critical drawback; they are unstable due to the two different paths the probe and reference beams take. Small environmental perturbations like floor vibrations, acoustic disturbance, temperature gradient, etc., can easily destabilize the system. Consequently, it is not only hard to build but also difficult to use this kind of separate path interferometric systems in industrial environments.

Conventional phase-contrast microscopes are designed to provide a fixed amount of phase control to specular component, usually $\pi/2$ or $-\pi/2$. These systems commonly use extended light sources such as an arc or halogen lamp. Although they are generally suitable for observing biological samples, conventional phase-contrast microscopes are not generally well suited for detecting a wide variety of defects that exist in semiconductor wafers and/or reticles.

U.S. Pat. No. 7,365,858. and U.S. Application Publication No. 2005/0105097 A1 describe a system for imaging biological samples. Two modes of operation are described, a "phase mode" and an "amplitude mode." The goal in the described amplitude mode is to obtain high contrast raw images. In phase mode, the described techniques attempt to extract phase information only. The descriptions mention liquid crystal spatial light modulation which is performed in a pupil conjugate through the use of beam splitters and additional lens groups, which are prone to power losses.

SUMMARY

A common-path interfermetry system and method and system are provided. According to some embodiments, a common-path interferometry system for the detection of defects in a sample is provided. The system includes an illumination source for generating electromagnetic energy directed toward the sample; optical imaging system for collecting a portion of the electromagnetic energy from the sample including a scattered component of the electromagnetic energy that is predominantly scattered by the sample, and a specular component of the electromagnetic energy that is predominantly undiffracted by the sample; a variable phase controlling system for adjusting the relative phase of the scattered component and the specular component so as to improve the ability to detect defects in the sample; and a sensing system for sensing at least portions of the scattered component and specular component.

According to yet other embodiments, a method of using common-path interferometry to detect defects in a sample is provided. The method includes directing electromagnetic energy toward the sample; collecting with an optical imaging system from the sample a scattered component of the electromagnetic energy that is predominantly scattered by the sample, and a specular component of the electromagnetic energy that is predominantly undiffracted by the sample; adjusting the relative phase of the scattered component and the specular component using a variable phase controlling system so as to improve the ability to detect defects in the sample; and sensing at least portions of the scattered component and specular component after said phase adjustment.

According to yet other embodiments, a common-path interferometry system is provided which includes: an illumination source for generating electromagnetic energy directed toward a sample; an optical imaging system for collecting a portion of the electromagnetic energy from the sample including a scattered component of the electromagnetic energy that is predominantly scattered by the sample, and a specular component of the electromagnetic energy that is predominantly undiffracted by the sample; a variable phase controlling system for adjusting the relative phase of the scattered component and the specular component so as to improve the ability to observe the sample; and a sensing system for sensing at least portions of the scattered component and specular component.

According to yet other embodiments, a method of using common-path interferometry to observe a sample is provided. The method includes directing electromagnetic energy toward the sample; collecting with an optical imaging system from the sample a scattered component of the electromagnetic energy that is predominantly scattered by the sample, and a specular component of the electromagnetic energy that is predominantly undiffracted by the sample; adjusting the relative phase of the scattered component and the specular component using a variable phase controlling system so as to improve observation of the sample; and sensing at least portions of the scattered component and specular component after said phase adjustment.

BRIEF DESCRIPTION OF THE DRAWINGS

The inventive body of work will be readily understood by referring to the following detailed description in conjunction with the accompanying drawings, in which:

FIGS. 7a-7c show an example of a compensation plate with Fourier filter strips for use with an interferometric defect detection system, according to some embodiments;

FIG. 9 shows a phase controller combined with a polarization rotator, according to some embodiments;

FIG. 10 shows an example of a polarization controller, according to some embodiments;

FIG. 11 shows an example of a continuously-variable attenuator using polarization, according to some embodiments;

DETAILED DESCRIPTION

Figure 1:
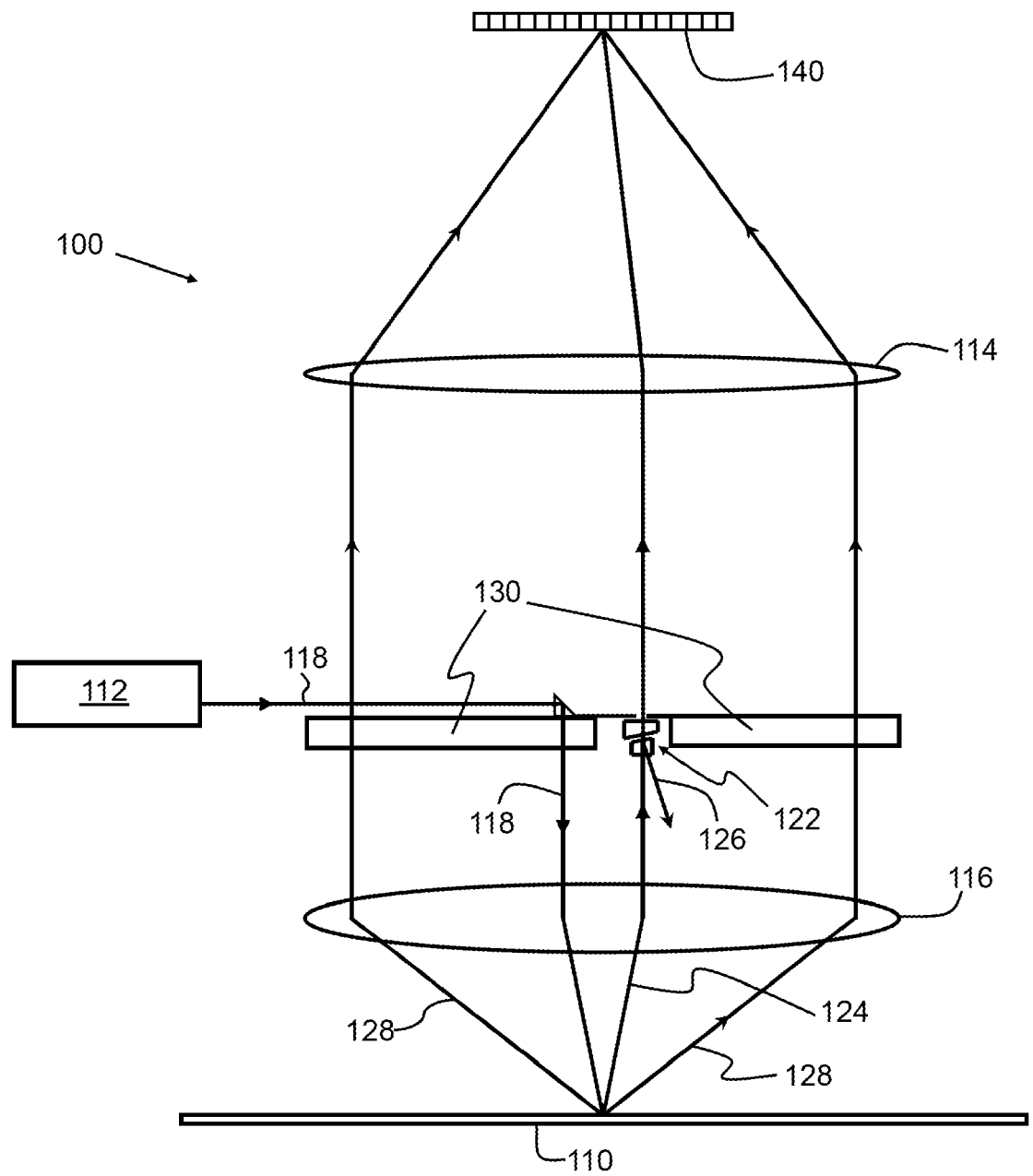
FIG. 1 shows an example of an interferometric defect detection system, according to some embodiments.

A detailed description of the inventive body of work is provided below. While several embodiments are described, it should be understood that the inventive body of work is not limited to any one embodiment, but instead encompasses numerous alternatives, modifications, and equivalents. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work.

The optical field can be described with complex amplitudes. Complex amplitudes can be conveniently represented in a Cartesian or in a polar coordinate system. It is represented by real and imaginary parts in a Cartesian coordinate system and amplitude and phase in a polar coordinate system. Therefore, the three phrases: "complex amplitude", "real and imaginary parts," and "amplitude and phase" are equivalent to each other as used herein, and the three terms are treated equivalently and can be exchanged with one another.

I. Defect Signal Equation

When a ray of light hits a wafer, the majority of the light is specularly reflected (or undiffracted) and a small part of the light is scattered (or diffracted) by both circuit patterns and defects in the wafer. The light intensity that an image sensor detects can be expressed as follows.

$$I \equiv |b + a + s|^2 + |q_a + q_s|^2 + |g|^2 \quad (1)$$
$$= |b|^2 + |a + s|^2 + |q_a + q_s|^2 + |g|^2 + 2|b||a + s|\cos(\varphi_{a+s})$$
$$= |b|^2 + |a + s|^2 + |q_a + q_s|^2 + |g|^2 + 2|b|(a_x + s_x)$$

where $b \equiv |b|\exp(i\phi_b)$; Complex amplitude of specular component, $a \equiv |a|\exp(i(\phi_a + \phi_b)) \equiv (a_x + ia_y)\exp(i\phi_b)$; Complex amplitude of light scattered by circuit patterns, $s \equiv |s|\exp(i(\phi_s + \phi_b)) \equiv (s_x + is_y)\exp(i\phi_b)$; Complex amplitude of light scattered by defects, $$a + s = |a|\exp(i(\varphi_a + \varphi_b)) + |s|\exp(i(\varphi_s + \varphi_b))$$
$$= |a + s|\exp(i(\varphi_{a+s} + \varphi_b))$$
$$= ((a_x + s_x) + i(a_y + s_y))\exp(i\varphi_b)$$

$q_a \equiv |q_a|\exp(i(\phi_{qa} + \phi_b))$; Complex amplitude of orthogonal polarization of circuit pattern component of total scattered light, $q_s \equiv |q_s|\exp(i(\phi_{qs} + \phi_b))$; Complex amplitude of orthogonal polarization of defect signal, and $g \equiv |g|\exp(i(\phi_g + \phi_b))$; Complex amplitude of stray light.

Note that all complex amplitudes are functions of position on the wafer. Additionally, only relative phases between different components matter. Therefore, the absolute phase of specular component $\phi_b$ does not play any role and can be set to zero without losing generality.

The optical path length difference of a stray light is assumed to be larger than the coherence length of an illumination light. Therefore, a stray light is added incoherently in the signal equation.

Equation (1) shows that the image comprises of not only a defect signal but also many of other unwanted components. In order to find a defect, components other than the defect signal need to be removed as much as possible. This is commonly done by die-to-die subtraction of the image of neighboring die from the image of current die. Note that in general at least two die-to-die subtractions, for example, [(current die image)−(left die image)] and [(current die image)−(right die image)], are required in order to correctly identify defect signals. Defects that show up in both subtracted images belong to a current die. Defects that show up in only one of the two subtracted images belong to neighboring dies. Therefore, by comparing two subtracted images, we can tell which defects belong to which die unambiguously. For memory area inspection, cell-to-cell image subtractions rather than die-to-die image subtractions are performed in order to minimize noises from wafer patterns. This method works effectively because the chance of having defects at the same locations in two different dies is negligibly small. The image intensity difference after die-to-die subtraction can be expressed as follows.

$$\Delta I \equiv I - I(s = q_s = 0) \quad (2)$$
$$= |a + s|^2 - |a|^2 + |q_a + q_s|^2 - |q_a|^2 + 2|b|s_x$$
$$= |a + s|^2 - |a|^2 + |q_a + q_s|^2 - |q_a|^2 + 2|b||s|\cos(\varphi_s) \quad (3)$$

Equation (3) is a general defect signal equation. The equation shows that the signal is a mixed bag of different kinds of signals. The first four terms constitute the dark field signal because they exist even if the specular component is filtered out. All dark field systems detect this part of the signal. Note that the raw dark field signal, the first four terms in equation (1) is always positive. But, this is not the part that is of interest. Rather, it is the defect signal, equation (3), that is of interest. The dark field part of the defect signal, i.e. the first four terms in equation (3), is a combination of both positive and negative terms whose magnitudes depend not only on the defect pattern but also on circuit patterns around the defect. Therefore, the dark field part of a defect signal can either be positive, negative, or zero depending on the circuit pattern around the defect. This means that dark field systems cannot detect defects in a consistent manner. Furthermore, as the defect size gets much smaller than the wavelength, the magnitude of the dark field signal becomes so small that it can be easily swamped by noise. The last term in the signal equation is the interference term. That is, the last term originates from interference between the defect signal amplitude and the specular component. The sign and magnitude of the interference term depends not only on the strength of the specular component but also on the relative phase between the defect signal amplitude and the specular component. Current bright field systems detect both dark field and interference terms simultaneously without controlling the relative phase between the defect signal amplitude and the specular component. In this case, the dark field terms and interference terms can either bolster or cancel each other depending on the pattern of defect itself and surrounding circuit patterns as well. This means that the current bright field systems cannot offer a consistent performance of defect detection. Therefore, both current dark field and bright field systems are severely handicapped.

The solutions described herein come out of the signal equation naturally. The signal equation shows the importance of controlling the relative phase between the defect signal amplitude and the specular component for a consistent performance. By controlling the relative phase, both the sign and the magnitude of interference term can be controlled. For example, if we set the relative phase to zero, the magnitude of interference term attains positive maximum. If we set the relative phase to 180°, the magnitude of interference term attains negative maximum. Thus, controlling of the relative phase not only can be used to vary the magnitude of interference term, but can also be used to change the sign of magnitude value. Owing to this capability of changing the sign, it is always possible to match the signs of the interference term and the dark field term. When the signs of interference term and dark field term are the same, they bolster each other. The total defect signal can be maximized by making the interference term attain one of its maximum values with the same sign as that of dark field term. Maximizing the total defect signal through the control of relative phase between the defect signal amplitude and the specular component is important for a consistent system performance in the future. The relative phase can be controlled by controlling either the phase of specular component or the phase of scattered component.

However, it is usually easier to control the phase of specular component because the etendue of specular component is much smaller than that of scattered component.

The signal equation reveals another important fact: the interference term is actually an amplified defect signal by the specular component. That is, even if the original defect signal is small, it can be amplified by the specular component by a large amount because the specular component is usually very intense. This is akin to the coherent detection of optical signals used in high sensitivity optical communication systems. Furthermore, this amplification process turns out to be a noiseless. See, e.g., Philip C. D. Hobbs. "Building Electro-Optical Systems; Making it all work," John Wiley & Sons, Inc., 2000, pp 30-32, which is incorporated by reference herein. This signal amplification process is so ideal that it does not degrade but rather maintains the signal-to-noise ratio. This kind of amplification is called "noiseless parametric amplification". In signal amplification, the quality of the first stage amplifier is the most important. The specular component provides the possibility of noiseless first stage signal amplification. The techniques described herein can take advantage of this by fully controlling the amplitude of specular component and the relative phase between the defect signal amplitude and the specular component. By realizing this noiseless amplification of signal, high signal-to-noise ratio can be achieved with the described techniques even if the original signal is weak. The high signal-to-noise ratio means high sensitivity and low false detection in defect detection.

According to certain embodiments, the scattered component and the specular component are interfered with each other at image plane and the relative phase between the two components are actively controlled in order to detect defects in a more sensitive and reliable way.

II. System Configuration:

The interferometric defect detection system can be configured in many different ways. Many examples include a common path and the controllability of the relative phase between the defect signal and the specular component.

1. Example of System Configuration. FIG. 1 shows an example of an interferometric defect detection system 100, according to some embodiments. A light beam 118 is generated by illumination source 112 which according to some embodiments is a coherent source such as a laser. Beam 118 is reflected towards the surface of the sample 110 as shown and illuminates a sample surface. The sample 110 can be a wafer, reticle, or other sample being inspected. The surface of sample 110 scatters (or diffracts) part of the illumination beam and specularly reflects the rest. The scattered and specularly reflected portions of the whole light are referred to herein as the "scattered component" and "specular component" respectively. The scattered component is represented by beams 128, and the specular component is represented by beam 124. A high-resolution optical system including front-end lens system 116 and back-end lens system 114 collects both the scattered and specular components of light and directs them to an image sensor 140. Note that many different kinds of image sensors could be used for system 100. According to some embodiments, two-dimensional image sensors such as CCD, Time Delay and Integration (TDI), and the like, have been found to be appropriate for many applications. As shown in FIG. 1, both the scattered component 128 and specular components 124 pass through the same optical system. Thus, the embodiments described are a type of common path interferometer system. This feature is advantageous for the stability of the system performance. This is because any disturbances to the common path interferometer are likely to affect both optical paths by the same amount and the relative phase difference between scattered and specular components is likely to be maintained.

According to some embodiments, phase controller and attenuator 122 is installed in the path of the specular component 124. The specular component passes through a phase controller 122 and its phase can be controlled to maximize defect detection sensitivity or to determine both phase and amplitude of defect signals. Scattered light beams 128 are passed through a compensation plate 130 to compensate the large amount of path length difference between the specular and scattered components. Phase control is an advantageous feature—as will be shown in later sections—and can be utilized to dramatically improve the defect detection capability. According to some embodiments, the specular component 124 can also be attenuated to improve image contrast by adding reflective coating on one of the surfaces of phase controller components. The reflected portion of specular component 124 is represented in FIG. 1 with beam 126. Note that the phase controller and attenuator are located at the primary pupil plane or aperture stop, which advantageously avoids power loss and complexity due to additional pupil relay system, beam splitters and other components that may be needed otherwise.

Many different kinds of light sources can be used for source 118. Bright sources are preferred in many applications because they allow a clean spatial separation of specular component from scattered component at pupil conjugate planes of the optical imaging system and also make the Fourier filtering very effective. In general, the brighter the source, the better. The brightest sources currently available are lasers. Therefore, lasers are the preferred sources for many applications. The sample can be illuminated with a laser in either coherent or incoherent fashion. However, incoherent illumination with a laser has significant drawbacks; it not only requires a costly speckle buster but also makes Fourier filtering much less effective compared with coherent illumination. Therefore, coherent illumination with laser is preferred in the technique herein. Other sources like arc lamp, light emitting diodes (LED), etc, can also be used. Note that the use of lasers as a light source can create damaging hot spots on or in some lenses. This problem can be mitigated by lens design or by the use of sturdy lens material such as specially formulated fused silica, calcium fluoride, lithium fluoride, etc.

The phase controller 122 should be placed at or close to pupil conjugates of the optical imaging system in order to be able to spatially separate the specular component from the scattered component in a clean fashion and also to achieve uniform performance over the whole imaging field. The primary pupil conjugate is the aperture stop of the optical imaging system. The phase controller 122 is placed at or close to the aperture stop plane of the imaging system in FIG. 1. Placing the phase controller at or close to the aperture stop plane of the optical imaging system is preferred for many applications because it does not require additional optical parts that are not only bulky and costly but also can reduce image quality and energy efficiency. It has been found that in cases where a laser is used as light source 112 and the sample 110 is illuminated coherently, the size of specular component at pupil conjugate plane becomes tiny, usually smaller than 1 mm, and consequently, the phase controller can be made quite small and not to take much space or interfere with other system components.

The ability to place the phase controller directly at or close to the aperture stop plane of the optical imaging system even if the area is narrow and crowded with other parts is a practical advantage in many applications. This advantage is especially valuable in the current and future defect detection system designs because it is very hard and also very costly to add more optical elements to relay out the aperture stop into less crowded area when the wavelengths are as short as those of deep ultraviolet (DUV) light used in the current and future defect detection systems. According to some alternate embodiments, in cases where area of aperture stop is too narrow or crowded to be able to position a phase controller, the aperture stop plane can be relayed out to a less crowed area by designing in a high quality pupil relay system. However, this design brings with it undesirable side effects. Additionally, in many cases, especially in the designs of high etendue DUV systems, it is difficult and costly to design in a suitable pupil relay system.

Figure 2A:
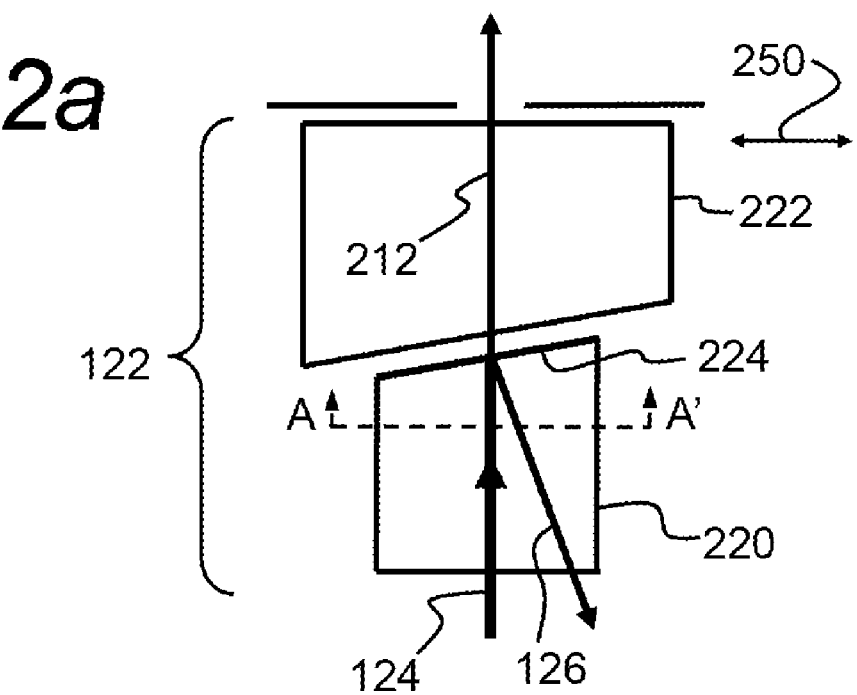
FIGS. 2a and 2b show an example of a phase controller and attenuator, according to some embodiments.
Figure 2B:
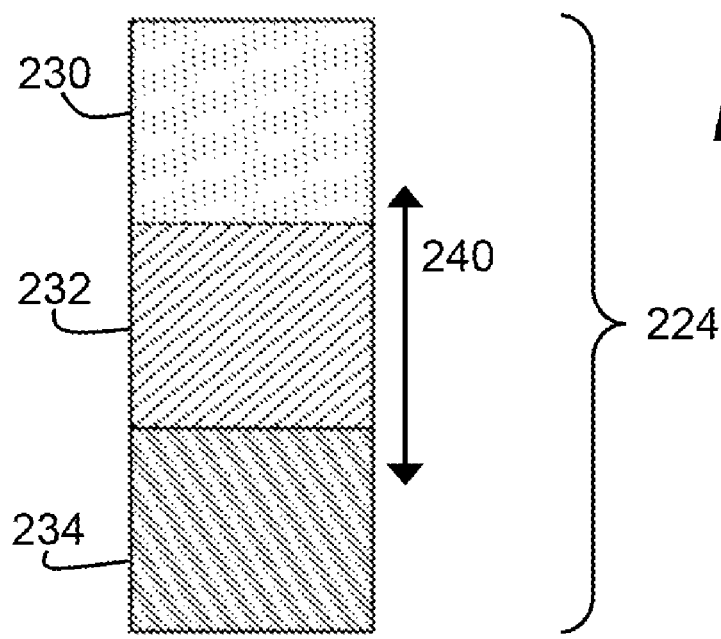

2. Phase Controller. FIGS. 2a and 2b show an example of a phase controller and attenuator. According to some embodiments, a phase controller is used to change the relative phase between scattered and specular components of light. Note that absolute phase is generally not of interest. Rather, it is the relative phase between scattered and specular components that is generally of interest. Therefore, the phase controller can be installed in the path of either the specular or scattered component. While most figures herein show the phase controller installed in the path of the specular component, according to some embodiment, the phase controller is installed in the path of the scattered component. There are a variety of ways of changing the phase of a beam of light. One technique of changing the phase is to change the optical path length of the beam. The optical path length can be changed easily by varying the thickness of the optical material that the beam passes through. These kinds of phase controllers can be made in many different ways. One way of making these kinds of phase controllers is to overlap two wedged glass plates as shown in FIG. 2a. Phase controller 122 makes use of an upper glass wedge 222 and a lower glass wedge 220. Incoming light beam 124 enters the lower wedge 220 and at least a portion passes through the upper wedge 222 as light beam 212. By moving one of the wedged plates in directions indicated by arrow 250, the optical path length of the passing-through beam is changed. For example, the upper wedge 222 can be moved rightward to increase the path length and leftward to decrease the path length.

An attenuator can be added easily to the kind of phase controller shown in FIG. 2a by putting reflective coating on one of the surfaces of phase controller components. For example, in FIG. 2a a reflective coating 224 is positioned at a surface of lower wedge 220 as shown. According to this example, a portion of incoming beam 124 is reflected by coating 224 and dumped as represented by dump beam 126. According to some embodiments, the attenuation amount can be step-varied by putting several different reflective coatings in a row and making the component movable. FIG. 2b shows an example of reflective coating 224 a viewed along the line A-A' of FIG. 2a. In this example, coating 224 is made up of three different reflective coatings 230, 232 and 234, arranged as shown in the direction of arrow 240. By moving lower wedge 220, different levels of attenuation can be achieved.

Figure 3:
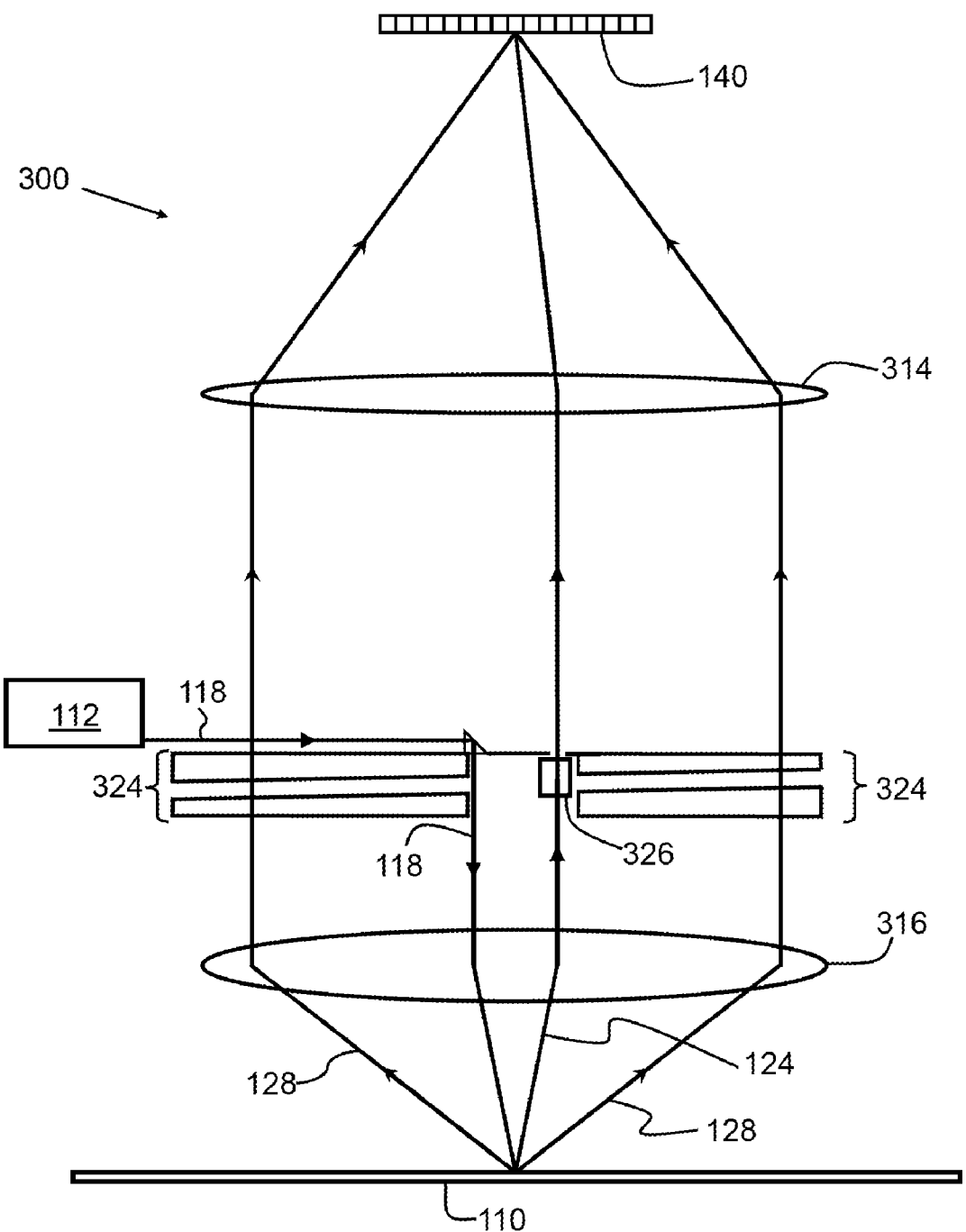
FIG. 3 shows and an example of an interferometric defect detection system, according to some embodiments.

FIG. 3 shows and an example of an interferometric defect detection system 300, according to some embodiments. In FIG. 3, the phase of the scattered component, represented by beams 128 are varied using the glass wedges 324. Coherent light source 112 generates illumination beam 118 which is reflected toward the surface of sample 110. The scattered component of the reflected light is represented by beams 128 and the specular component is represented by beam 124. By moving the upper wedge relative to the lower wedge, the effective path length and phase of the scattered component is changed. Specular component 124 passes through a compensation block 326 to compensate for path length difference between the specular and scattered components. Front-end lens system 316 and back-end lens system 314 collect the light from sample 110 and focus the light on the image sensor 140.

Figure 4A:
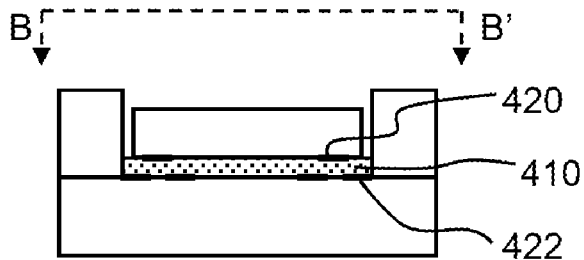
FIGS. 4a and 4b show an example for changing optical path length, according to some embodiments.
Figure 4B:
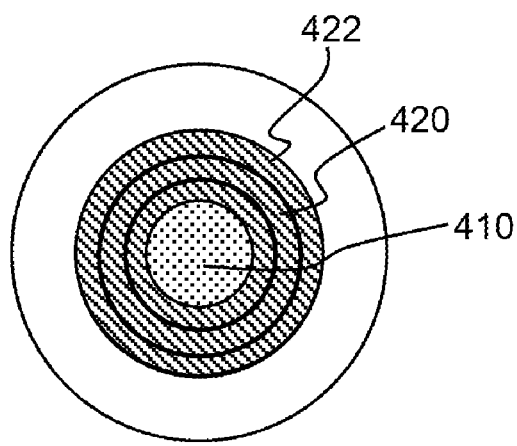

Another way of changing the optical path length is shown in FIGS. 4a and 4b. In this example, as shown in FIG. 4a, an optically transparent liquid 410 is injected between electrodes 420 and 422 of a ring capacitor. The thickness of the liquid 410 is varied by varying the voltage across the capacitor electrodes 420 and 422. Liquid crystal rather than regular liquid can also be used for liquid 410. In this case, optical path length can be varied by just changing the orientation of liquid crystal molecules. FIG. 4b shows a plan view of the structure of FIG. 4a in the direction along B-B'. Upper electrode 420 is shown along with liquid 410.

Figure 5:
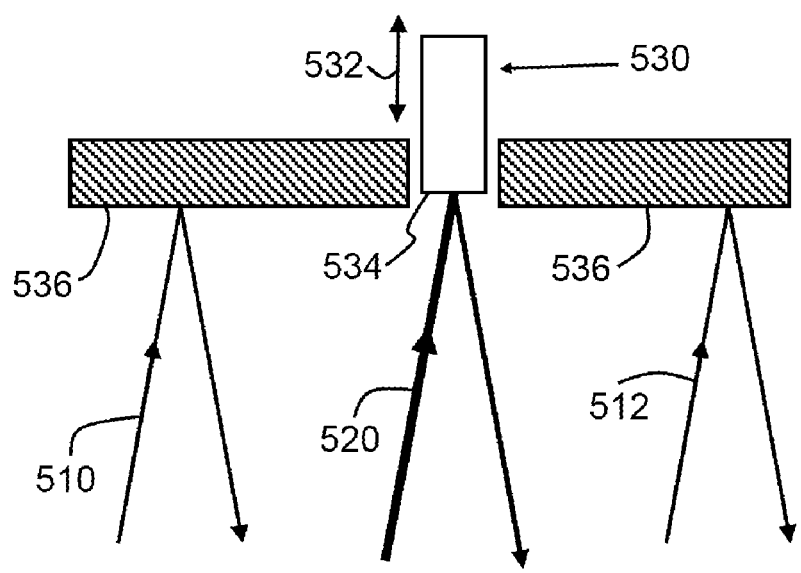
FIG. 5 shows an example of a movable mirror used to change the optical path length, according to some embodiments.

FIG. 5 shows an example of a movable mirror used to change the optical path length, according to some embodiments. The system includes a movable member 530 having a reflective surface. Incoming specular reflection beam 520 is partially reflected from surface 534 of member 530. Scattered light beams 510 and 512 are reflected from fixed reflective member 536. A movable mirror type phase controller has been found to be especially useful for applications using extremely short wavelength light, like a vacuum ultraviolet light or extreme ultraviolet light which might be used in future generation defect detection systems. This is because it is relatively difficult to find or develop transmissive optical materials for those wavelengths. The phase controlling mirror does not always need to be highly reflective. For many applications, especially when the dynamic range of image sensor is low, a low reflectivity is preferred because attenuating the specular component is useful in achieving proper image contrast. For example, it has been found that bare glass without any coating can provide adequate reflectivity. According to other embodiments, especially where a fast response is desirable, a phase controller can be constructed using electro-optical components.

Figure 6:
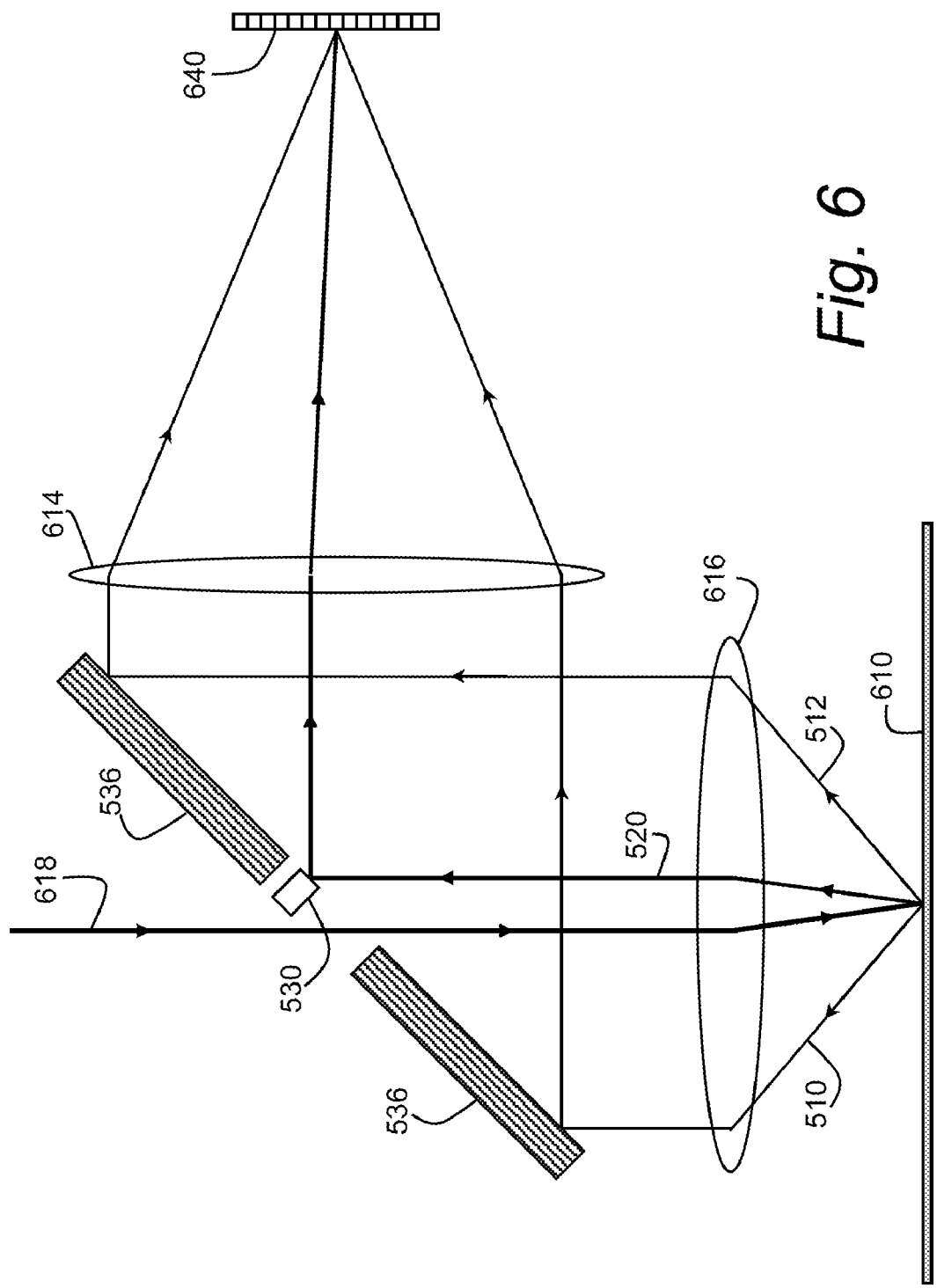
FIG. 6 shows an example of an interferometric defect detection system making use of a moveable mirror phase controller, according to some embodiments.

FIG. 6 shows an example of an interferometric defect detection system making use of a moveable mirror phase controller, according to some embodiments. Incoming light beam 618 is directed toward the surface of sample 610 which could be a wafer, reticle, or other sample being inspected. The scattered component, represented by beams 510 and 512 pass through lens system 616, are reflected from reflective member 536 before passing through lens system 614 which directs the beams toward the image sensor 640. The specular component beam 520 is reflected from the surface of moveable reflective member 530 as described with respect to FIG. 5.

Note that although a continuously-variable phase controller is shown for many of the embodiments described herein, according to some embodiments, a discretely-variable phase controller can be used. In general, a discretely-variable phase controller cannot perform as well as continuously-variable phase controller. However, if the total number of phase selections is three or larger, it may be acceptable in practice for some applications. For example, if the total number of phase selections is limited to four, the best choices of phase values for the discretely-variable phase controller may be 0°, ±180°, −90° and 90°. Even three phase selections may work in some applications. In this case, the best choices of phase values is 0°, 120° and −120°. Reducing the number of phase selections to two, e.g. {0°, 180°} or {90°, −90°} is less preferred for many applications since the sign of interference term cannot be made the same as that of dark field term for both amplitude-type defects and phase-type defects.

3. Fourier Filtering. Blocking unwanted light at a pupil plane or aperture stop is called Fourier filtering because the light distribution at a pupil plane or aperture stop is the same as a Fourier transform of light distribution at an object plane. Fourier filtering is a desirable feature in many applications because it can effectively reduce the amount of noise-generating light. The majority of circuit patterns are formed in x- or y-directions and consequently scatter (or diffract) light in y- or x-directions. This kind of scattered light does not carry much information about defects but generate noise or saturates image sensors. Therefore, it is desirable to filter out this kind of light. FIGS. 7a-7c show an example of a compensation plate with Fourier filter strips for use with an interferometric defect detection system, according to some embodiments. In FIG. 7a, compensation plate 730 is shown with narrow Fourier filter strip members 750, 752, 754 and 756. In this example, light scattered in the x- and y-directions land on the filter strip members 750, 752, 754 and 756 at the pupil plane or aperture stop. In this way, this kind of unwanted light can be filtered out very effectively. A couple of crossed metal strips are all that are needed. Note that strip members 750, 752, 754 and 756 do not block much of the defect signal light while blocking most of the unwanted light in both x- and y-directions. This kind of Fourier filter that blocks unwanted light in both x- and y-directions is called two-dimensional Fourier filter. Two-dimensional Fourier filtering is much more effective in blocking unwanted light than the existing one-dimensional Fourier filtering. This also means that two dimensional Fourier filter makes the intensity of image much more uniform across the field compared with one dimensional Fourier filter. Uniform image intensity is important for many applications because it allows us to fully utilize the dynamic range of image sensor for the amplification of defect signal. The location of the strips does not need to be varied as long as the illumination beam 718 and prism 780 remains the same. Therefore, the Fourier filter does not need any driving mechanism and can be installed in a permanent fashion. Thus, two-dimensional Fourier filtering is achieved not only simply and easily but also with minimal impact to signal light. Also shown in FIG. 7a is upper glass wedge 722 and lower glass wedge 720. FIG. 7b shows a cross-sectional view of the arrangement of FIG. 7a along the line C-C', according to some embodiments. Compensation plate 730 is shown with an opening in which are disposed upper glass wedge 722 and lower glass wedge 720. The upper surface of lower glass wedge 720 has a variable reflective surface as shown and described with respect to FIGS. 2a-2b. FIG. 7c shows a cross-sectional view of the arrangement of FIG. 7a along the line D-D', according to some embodiments. Compensation plate 730 is shown with an opening in which are disposed upper glass wedge 722 and lower glass wedge 720 having a reflective surface 724.

According to other embodiments, Fourier filters in different directions than x- and y-directions can be added if needed. However, it has been found that too much Fourier filtering can be detrimental because Fourier filters block defect signal light as well as noise-generating light. The blocking of signal light can impact the final defect signal in two ways: it not only reduces the total amount of signal light but also makes the image of defect a little fuzzier through diffraction. There is usually an optimum amount of Fourier filtering that depends on the patterns on the wafer. Thus the amount of Fourier filtering which is desirable depends on the particular application.

4. Variable Pinhole Stop. Note that the techniques described herein work even without any pinhole or pinhole stop in the path of the specular component. However, it has been found that in many applications, a variable pinhole stop in the path of the specular component can improve the system performance. Most figures of a phase controller herein show variable pinhole stop on the top of the phase controller. The term "specular component" cannot be precisely defined because there are no clear boundaries between specular and scattered components. The specular component must contain some, even an extremely tiny amount of scattered (or diffracted) component. Therefore, the specular component actually means a combination of both unscattered (or undiffracted) light and low angle scattered light. The term "specular component" is used in this actual sense herein and is allowed to contain some amount of low angle scattered component. Because the specular component is allowed to contain some amount of low angle scattered light, we can vary the characteristics of the specular component by changing the amount of low angle scattered light contained. A variable pinhole stop is one of the simplest devices that can change the amount of scattered light in an actual specular component of light. A larger pinhole puts more scattered components into the specular component and vice versa. The important thing is that the pinhole size is directly related to spatial uniformity of the specular component of light at the image plane. A larger pinhole provides less spatial uniformity of specular component at the image plane because it passes more scattered light and vice versa. In other words, a larger pinhole averages less of the local variations of image intensity and vice versa. Thus, not only can we change the total amount of the specular component that can reach image sensor, but also the spatial uniformity of the specular component at an image plane by varying the pinhole size. The pinhole size of the variable pinhole diameter is shown in FIGS. 7b and 7c as dimension "p." This kind of variability of the specular component can be utilized to improve the defect detection capability.

5. Actuators. A phase controller uses some kind of mechanical or electrical actuator. The most convenient place to put an actuator may be right next to the phase controller. However, placing an actuator right next to the phase controller may introduce too much blocking of the signal light. In some examples, the actuator is placed at the periphery of the optical imaging system. The periphery of the optical imaging system is an attractive choice because it provides more space for the actuator. However, the drawback of this choice is that it requires some mechanism to transfer the actuator motion to the phase controller. The motion transfer mechanism must go across the pupil and can block the signal light. However, according to some embodiments, the problem of light blocking is resolved by making use of the fixed locations of Fourier filters. By installing the motion transfer mechanism like moving or rotating wires on the top of Fourier filters, further blocking of light than Fourier filters can be avoided. In FIGS. 7a and 7c, motion transfer member 726 is provided that runs along the path of Fourier filter member 754. Motion transfer member is driven by actuator 770. Similarly, motion transfer mechanisms for other parts like variable pinhole stops or wave plates can also be implemented the same way to minimize light blockage.

Figure 8:
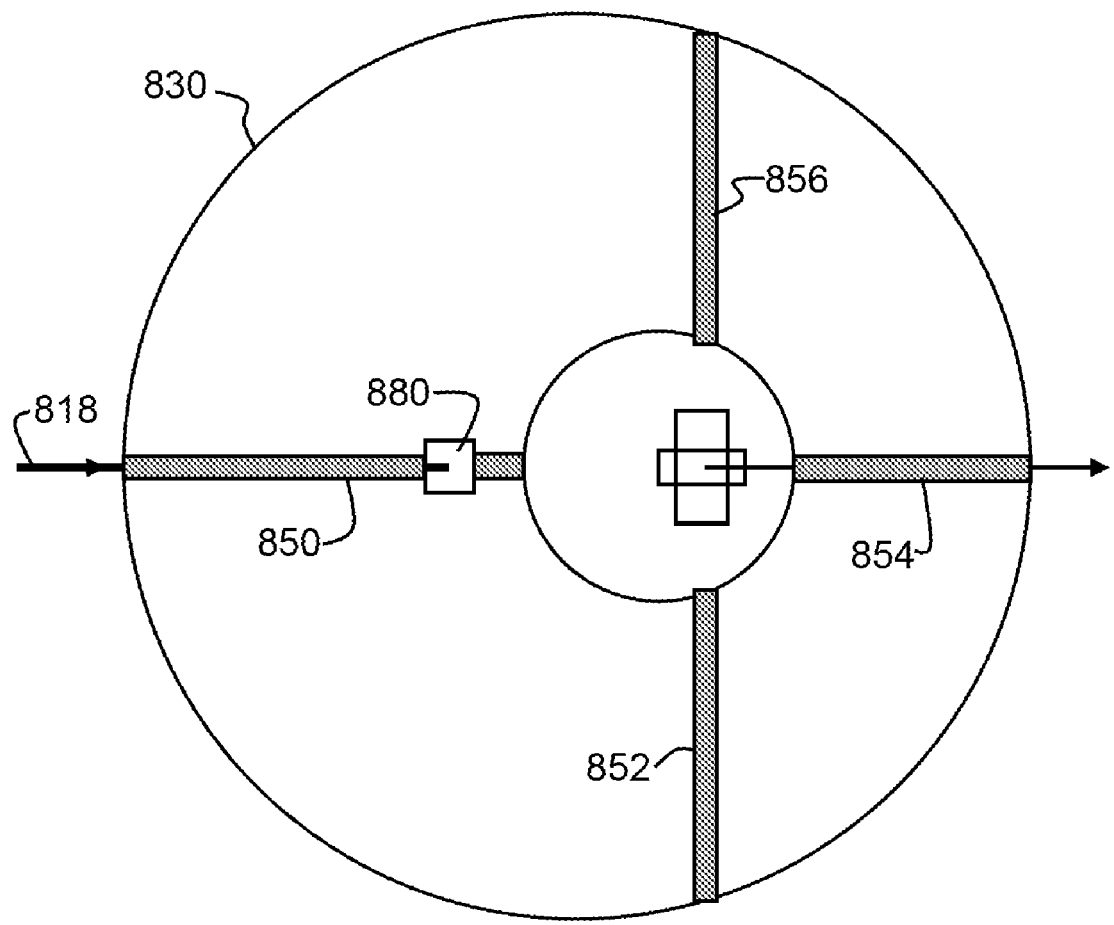
FIG. 8 shows an example of a placement of a folding prism for the illumination light, according to some embodiments.

6. Obscuration. The phase controller and its actuator unavoidably obscure (or block) some of the signal light. This kind of light blockage reduces not only the total amount of signal light that can reach the image sensor but also the resolving power of the optical system by diffracting light. This is an undesirable side effect. This undesirable side effect should be minimized as much as possible. In order to do that, both optical components and the actuator of the phase controller should be made as small as possible or the actuator should be placed at the periphery of the optical imaging system. FIG. 8 shows an example of a placement of a folding prism for the illumination light, according to some embodiments. Compensation plate 830 is arranged with Fourier filter strips 850, 852, 854 and 856 in a fashion similar to that shown in FIG. 7a. In the example of FIG. 8, an additional small reduction of obscuration can be achieved by placing the folding prism 880 for the illumination light beam 818 in line with the Fourier filter 850 as shown. Also, softening of the edges of the obscuration and optical imaging system's aperture stop can reduce the undesirable side effect.

Note that there is a beneficial side effect from the rather large obscuration caused by the phase controller. The obscuration works as the guard band in dark field mode. The large guard band along with two-dimensional Fourier filter makes the dark field mode very dark. This means that the dark field mode is characterized by low noise and, consequently, can maintain higher defect detection sensitivity compared with dark field systems with less darkness.

7. Polarization Control of Illumination Light. Tie detection sensitivity of some types of defects can critically depend on the polarization of the illumination light. Therefore, the capability of polarization control of the illumination light can be an important feature. Polarization of the illumination light can be easily and precisely controlled in the arrangements described herein because the etendue of the illumination light is small. Existing polarization control devices can be used. If polarization can be changed during the travel of illumination light through optical components, polarization change can be pre-compensated by experimentally determining the polarization characteristics of the illumination system.

8. Polarization Control of Collected Light. The polarization of a signal light can be different than that of the specular component. In order to achieve high defect detection sensitivity, the polarization of the specular component can be made parallel to that of a signal light to as great a degree as is possible. Therefore, according to some embodiments, the polarization of the specular component can be varied. The polarization of the specular component can be varied easily and precisely because the etendue of the specular component is small.

FIG. 9 shows a phase controller combined with a polarization rotator, according to some embodiments. FIG. 9 shows a lower wedged glass plate 920 having a reflective coating 924, an upper moveable wedged glass plate 922 and a variable pinhole stop 950. A rotatable $\lambda/2$ plate 960 is positioned above the variable pinhole stop 950. Incoming specular light beam 916 is partially reflected by coating 924, and a portion of the beam 912 passes through the moveable wedged glass plate 922, pinhole stop 950 and rotatable $\lambda/2$ plate 960. The polarization controllability of the arrangement shown in FIG. 9 is somewhat limited in that it cannot transform the polarization of an incoming specular component to an arbitrary type of polarization. However, the arrangement can rotate an incoming linear polarization in any direction. As long as the defect and its surrounding patterns do not have any helical structure, no polarizations other than linear polarizations are needed to maximize the defect detection sensitivity. This has been found to be the case for semiconductor wafers and reticles. Therefore, a simple polarization control device shown in FIG. 9 will be adequate for a wafer or reticle defect detection.

If a more general polarization control is needed, a slightly more complicated polarization controller shown in FIG. 10 can be employed. FIG. 10 shows a lower wedged glass plate 1020 having a reflective coating 1024, an upper moveable wedged glass plate 1022 and a variable pinhole stop 1050. A rotatable $\lambda/2$ plate 1060 and a rotatable $\lambda/4$ plate 1062 are positioned above the variable pinhole stop 1050. Incoming specular light beam 1016 is partially reflected by coating 1024, and a portion of the beam 1012 passes through the moveable wedged glass plate 1022, pinhole stop 1050, rotatable $\lambda/2$ plate 1060 and rotatable $\lambda/4$ plate 1062. The arrangement shown in FIG. 10 can convert any incoming polarization to any type of polarization. Its working principle is described in: R. M. A. Azzam and N. M. Bashara, "Ellipsometry and Polarized Light" Elsevier Science B. V., 1999, pp 72-84, which is incorporated by reference herein.

Figure 12:
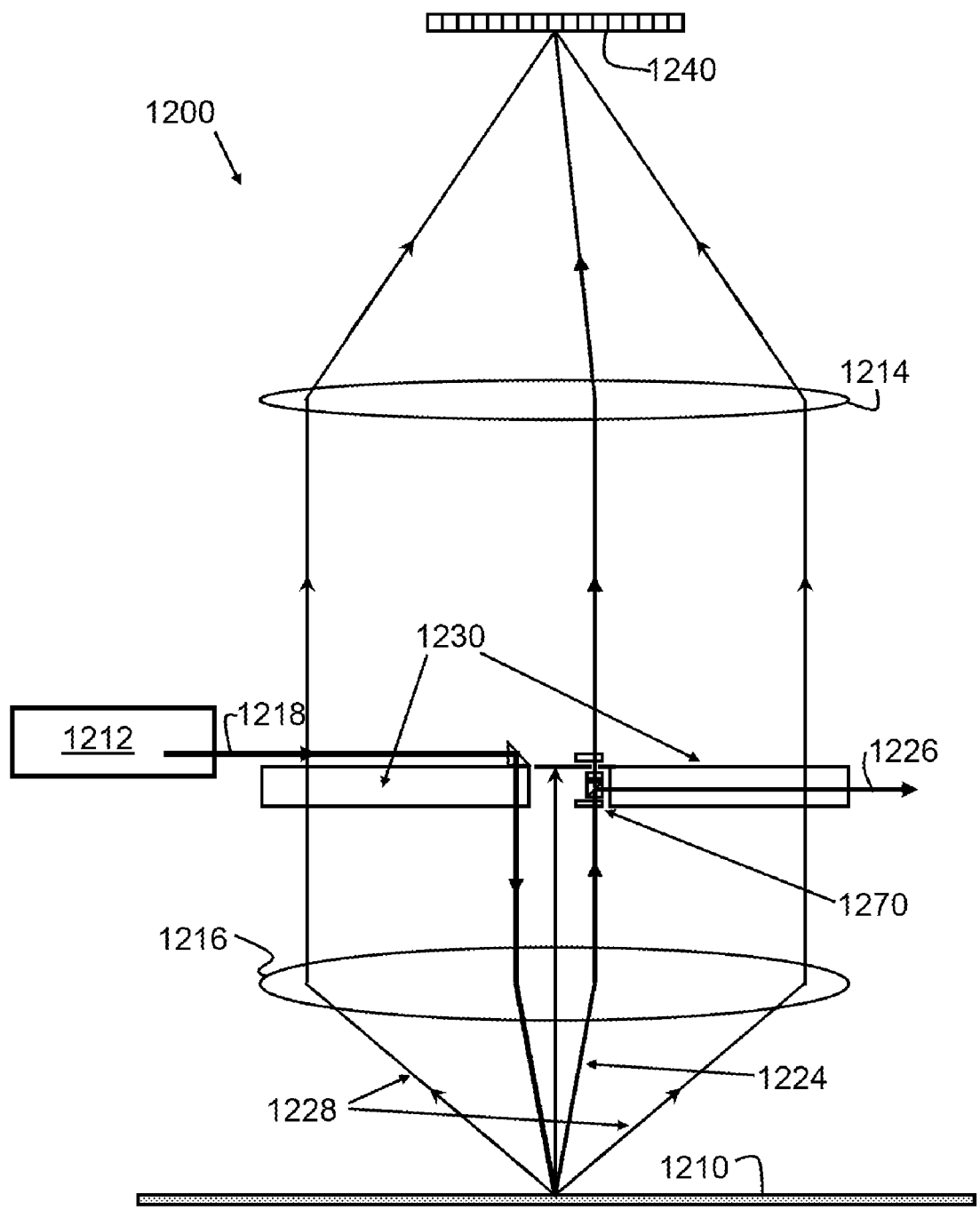
FIG. 12 shows an example implementation of a system using the type of attenuator shown in FIG. 11.
Figure 13A:
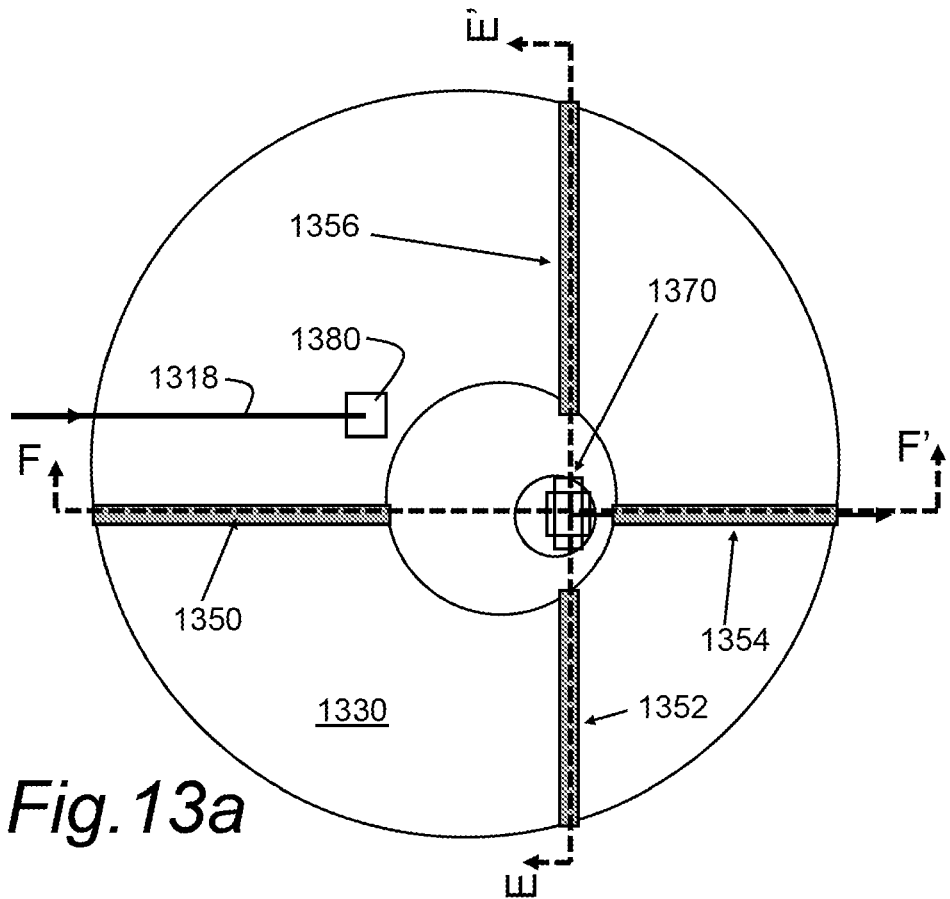
FIGS. 13a-13c show further detail of the system in the vicinity of the pupil or aperture stop, according to some embodiments.
Figure 13B:
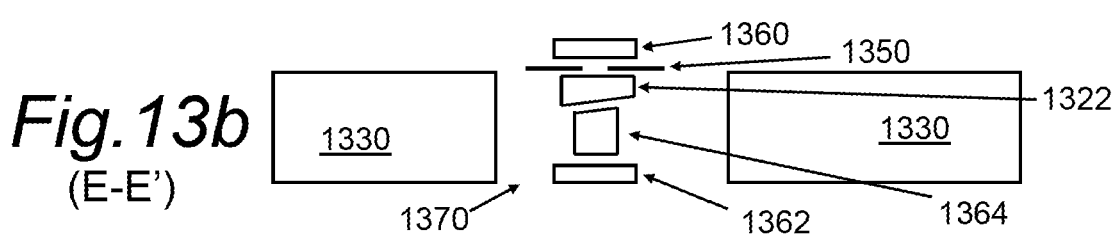
Figure 13C:
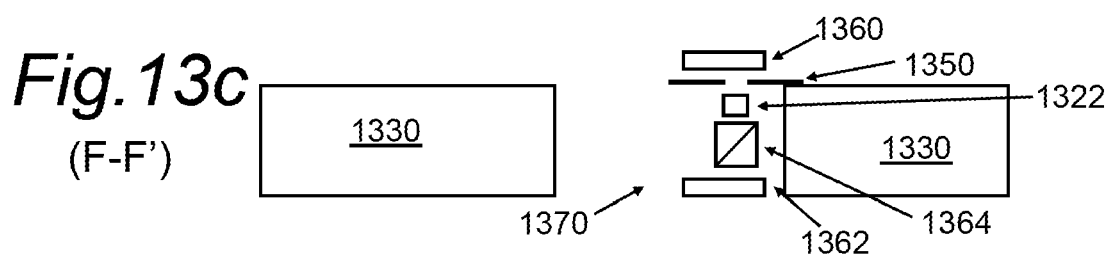
Figure 14:
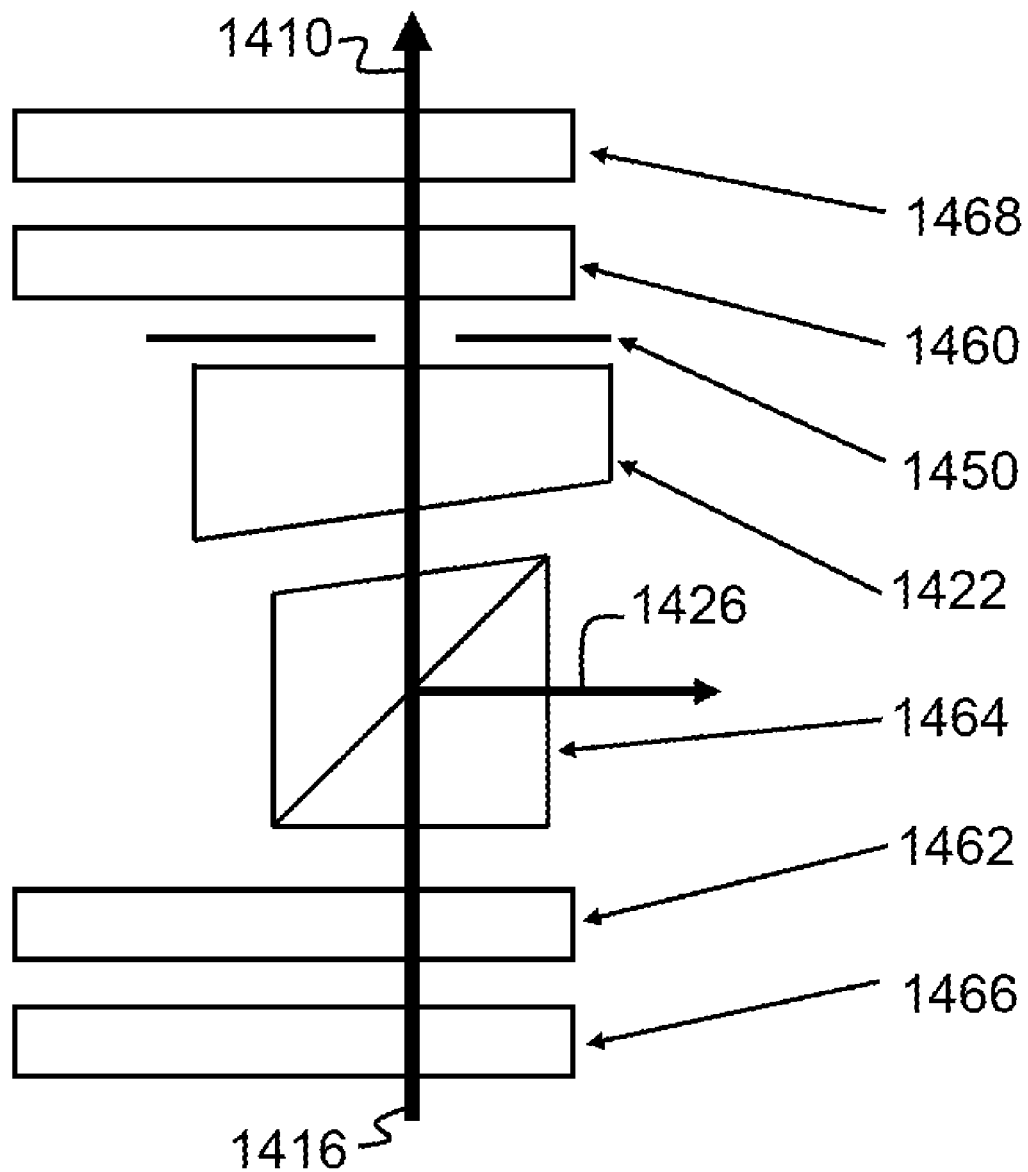
FIG. 14 shows an example of an attenuator having both λ/2 and λ/4 plates, according to some embodiments.

9. Amplitude Attenuation. As mentioned previously, the specular component amplifies the defect signal. The stronger the specular component is, the more amplification of the defect signal. Therefore, unattenuated or a strong specular component is preferred in most cases. However, too strong of the specular component can saturate the image sensor of limited dynamic range. Saturation of the image sensor not only reduces but also distorts the defect signal. In this case, some enhancement of the contrast of raw images, sometimes along with the increase of illumination light intensity, is useful to recover the defect signal. The simplest method is absorbing the specular component using some light absorbing material. However, this simple attenuation method is not suitable for wafer or reticle defect detection due to the high power of the specular component. The high power of the specular component is very likely to damage light-absorbing attenuators. A more suitable way of attenuating the specular component is to reflect off the excessive portion of the specular component. This kind of attenuator can easily be constructed by putting reflective dielectric coating on one of the phase controller components as shown in FIGS. 2a and 2b. The amount of attenuation can be varied by putting several different reflective coatings in a row and make them movable as shown in FIG. 2b. This kind of attenuator is simple and does not require additional optical component. However, it is hard to achieve continuous variation of attenuation with this kind of simple attenuators. For increased performance, a continuously-variable attenuator can be used. One way to make continuously-variable attenuator is to utilize polarization property of light. It is well-known that continuously-variable attenuator can be constructed using polarization optical parts. FIG. 11 shows an example of a continuously-variable attenuator using polarization, according to some embodiments. FIG. 12 shows an example implementation of a system using the type of attenuator shown in FIG. 11. FIGS. 13a-13c show further detail of the system in the vicinity of the pupil or aperture stop, according to some embodiments. Referring to FIG. 11, beam 1116 enters a polarization beam splitter 1164 which reflects off the s-polarized light 1126 while transmitting p-polarized light 1110. By controlling the polarization direction of incoming light using the rotatable $\lambda/2$ plate 1162, the amount of specular component that passes through the polarization beam splitter can be controlled in continuous fashion. P-polarized light 1110 pass through moveable wedged glass plate 1122 and variable pinhole stop 1150 as previously described. The rotatable $\lambda/2$ plate 1160 on the output side can be used to reorient the polarization of the exiting light in any direction. This attenuation method is very well suited for wafer or reticle inspection. However, this method is not completely general. It works nicely particularly with linear polarizations. If more general polarizations need to be used, additional optical components can to be added to the attenuator. FIG. 14 shows an example of an attenuator having both $\lambda/2$ and $\lambda/4$ plates, according to some embodiments. Beam 1416 enters a polarization beam splitter 1464 which reflects off the s-polarized light 1426 while transmitting p-polarized light 1410. By controlling the polarization direction of incoming light using both the rotatable λ/4 plate 1466 and the rotatable λ/2 plate 1462, the amount of specular component that passes through the polarization beam splitter can be controlled in continuous fashion. P-polarized light 1410 pass through moveable wedged glass plate 1422 and variable pinhole stop 1450 as previously described. The rotatable λ/2 plate 1460 and the rotatable λ/4 plate 1468 on the output side can be used to reorient the polarization of the exiting light in any direction. By rotating both λ/2 and λ/4 plates, any kind of polarization of the specular component can be obtained with proper attenuation.

Referring to FIG. 12, interferometric defect detection system 1200, includes an illumination source 1212 which generates a coherent beam 1218. Beam 1218 is directed towards the surface of the sample 1210 as shown. The sample 1210 can be a wafer, reticle, or other sample being inspected. The scattered component from sample 1210 is represented by beams 1228, and the specular component is represented by beam 1224. A high-resolution optical system including lens systems 1214 and 1216 collects both the scattered and specular components of light and directs them to an image sensor 1240. Subsystem 1270 is positioned in the path of specular component 1224 and includes a phase controller, variable attenuator, and one or more polarization rotators such as described and shown with respect to FIGS. 11 and 14. Scattered light beams 1228 are passed through a compensation plate 1230 to compensate for the path length difference between the specular and scattered components. A beam dump 1226 represents the portion of specular component 1224 that is attenuated by the variable attenuator.

Referring to FIG. 13a, compensation plate 1330 is shown with narrow Fourier filter strip members 1350, 1352, 1354 and 1356. Illumination beam 1318 is reflected toward the sample (not shown) using prism 1380. Subsystem 1370 is positioned as shown and includes a phase controller, variable attenuator, and one or more polarization rotators such as described and shown with respect to FIGS. 11 and 14. FIGS. 13b and 13c show cross-sectional views of the arrangement of FIG. 13a along the line E-E' and F-F' respectively. In both FIGS. 13b and 13c, compensation plate 1330 is shown with an opening in which are disposed the various components of subsystem 1370. Polarization beam splitter 1364 reflects off the s-polarized light while transmitting p-polarized light. By controlling the polarization direction of incoming light using the rotatable λ/2 plate 1362, the amount of specular component that passes through the polarization beam splitter can be controlled in continuous fashion. P-polarized light passes through moveable wedged glass plate 1322 and variable pinhole stop 1350. The rotatable λ/2 plate 1360 on the output side can be used to reorient the polarization of the exiting light in any direction.

10. High Incidence Angle Illumination. For some applications, it is desirable to increase the incidence angle of illumination light to reduce the wafer pattern noise. The techniques described herein are flexible with the incidence angle of illumination light. The techniques can accommodate not only a low incidence angle but also a high incidence angle illumination light. FIGS. 15 through 18 show examples of this.

Figure 15:
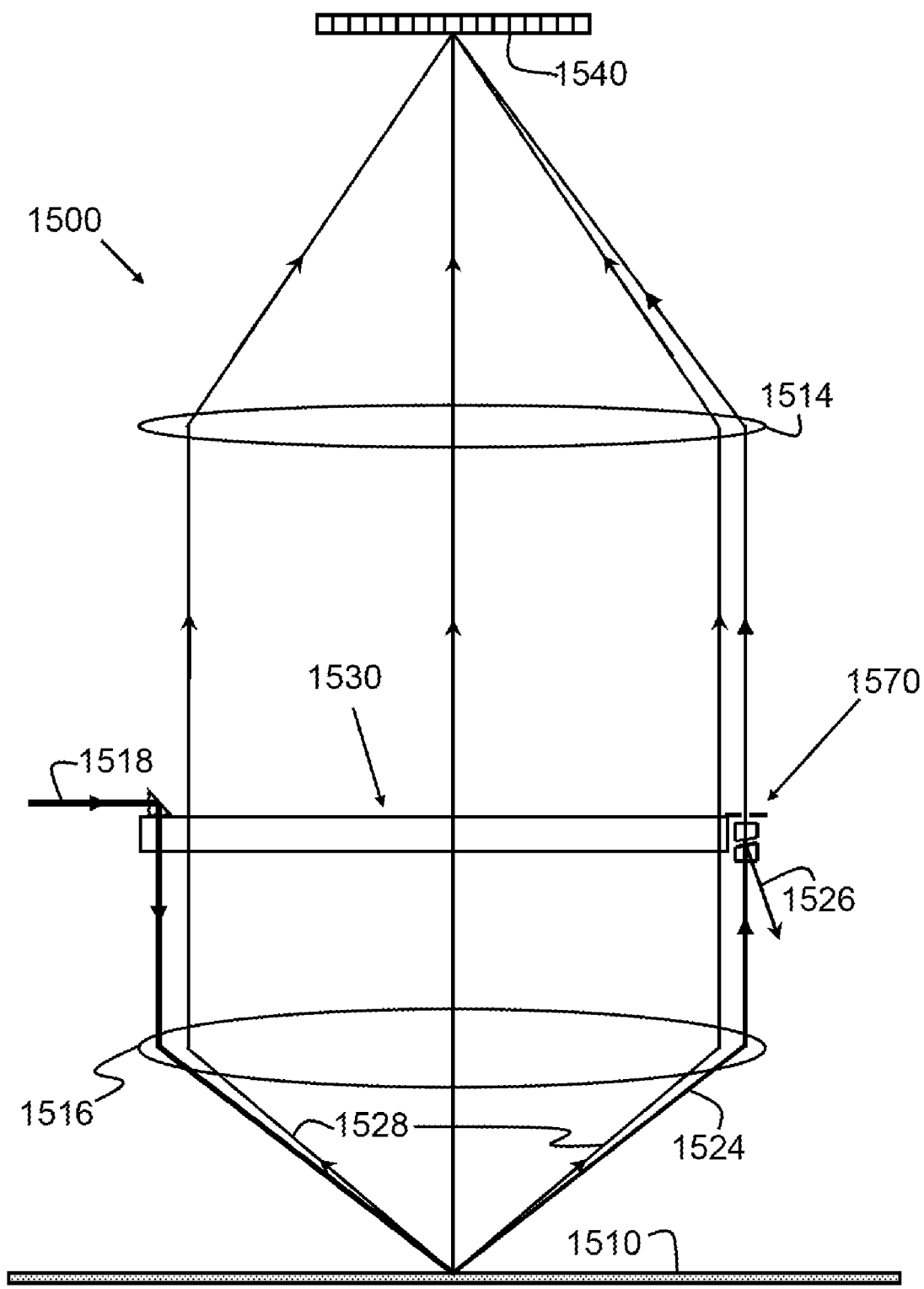
FIG. 15 shows an example of an interferometric defect detection system with high incidence angle illumination, according to some embodiments.

FIG. 15 shows an example of an interferometric defect detection system with high incidence angle illumination, according to some embodiments. Interferometric defect detection system 1500, includes an illumination source beam 1518 which is directed towards the surface of the sample 1510 as shown. The sample 1510 can be a wafer, reticle, or other sample being inspected. The scattered component from sample 1510 is represented by beams 1528, and the specular component is represented by beam 1524. A high-resolution optical system including lens systems 1514 and 1516 collects both the scattered and specular components of light and directs them to an image sensor 1540. Subsystem 1570 is positioned in the path of specular component 1524 and includes a phase controller and attenuator such as described and shown with respect to FIGS. 2a and 2b. Scattered light beams 1528 are passed through a compensation plate 1530 to compensate for path length differences between the specular and scattered components. A beam dump 1526 represents the portion of specular component 1524 that is attenuated by the attenuator.

Figure 16:
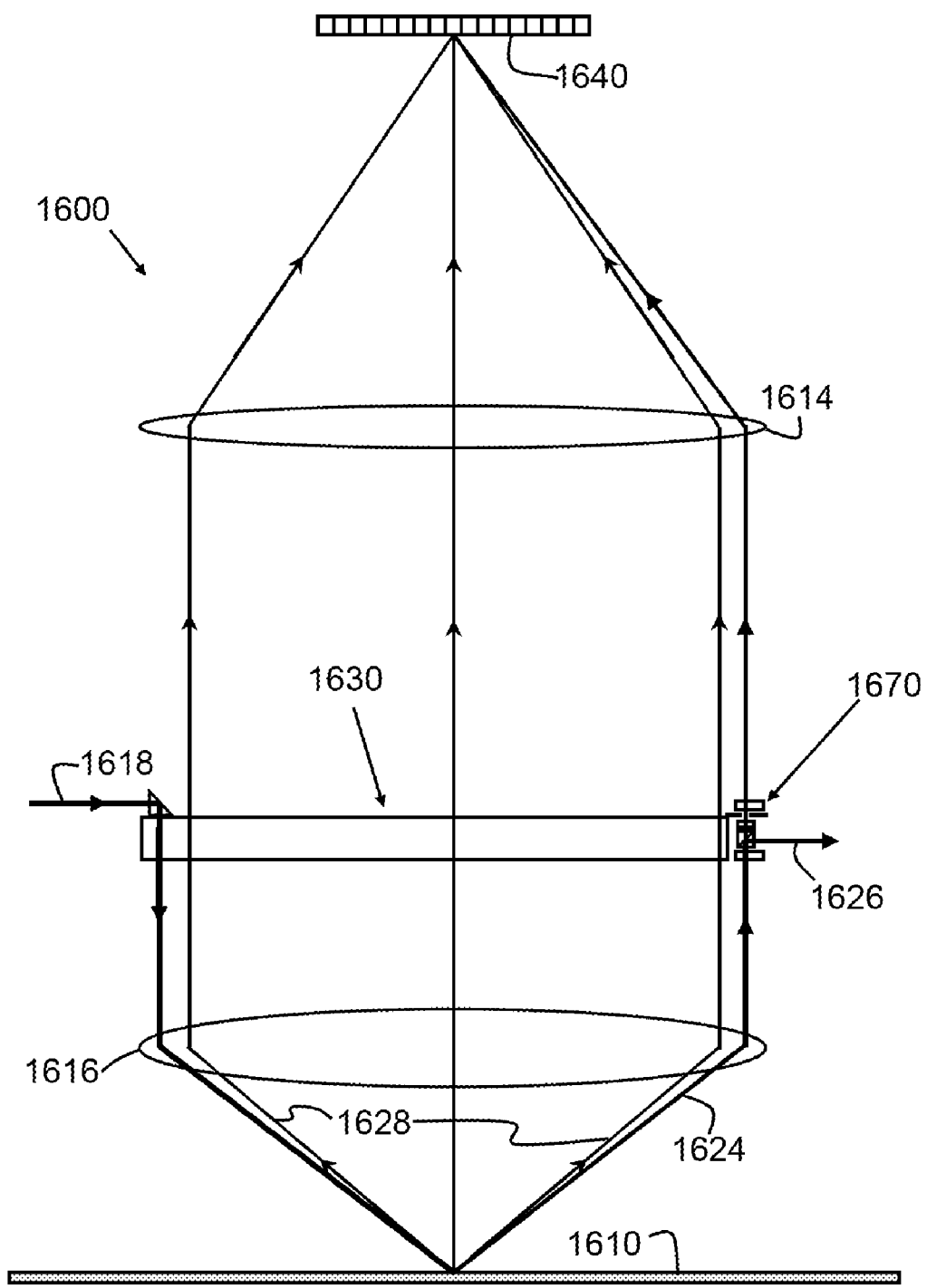
FIG. 16 shows an example of an interferometric defect detection system with high incidence angle illumination and a variable attenuator, according to some embodiments.

FIG. 16 shows an example of an interferometric defect detection system with high incidence angle illumination and a variable attenuator, according to some embodiments. Interferometric defect detection system 1600, includes an illumination source beam 1618 which is directed towards the surface of the sample 1610 as shown. The sample 1610 can be a wafer, reticle, or other sample being inspected. The scattered component from sample 1610 is represented by beams 1628, and the specular component is represented by beam 1624. A high-resolution optical system including lens systems 1614 and 1616 collects both the scattered and specular components of light and directs them to an image sensor 1640. Subsystem 1670 is positioned in the path of specular component 1624 and includes a phase controller and variable attenuator such as described and shown with respect to FIGS. 9-11 and 14. Scattered light beams 1628 are passed through a compensation plate 1630 to compensate for path length differences between the specular and scattered components. A beam dump 1626 represents the portion of specular component 1624 that is attenuated by the variable attenuator.

Figure 17:
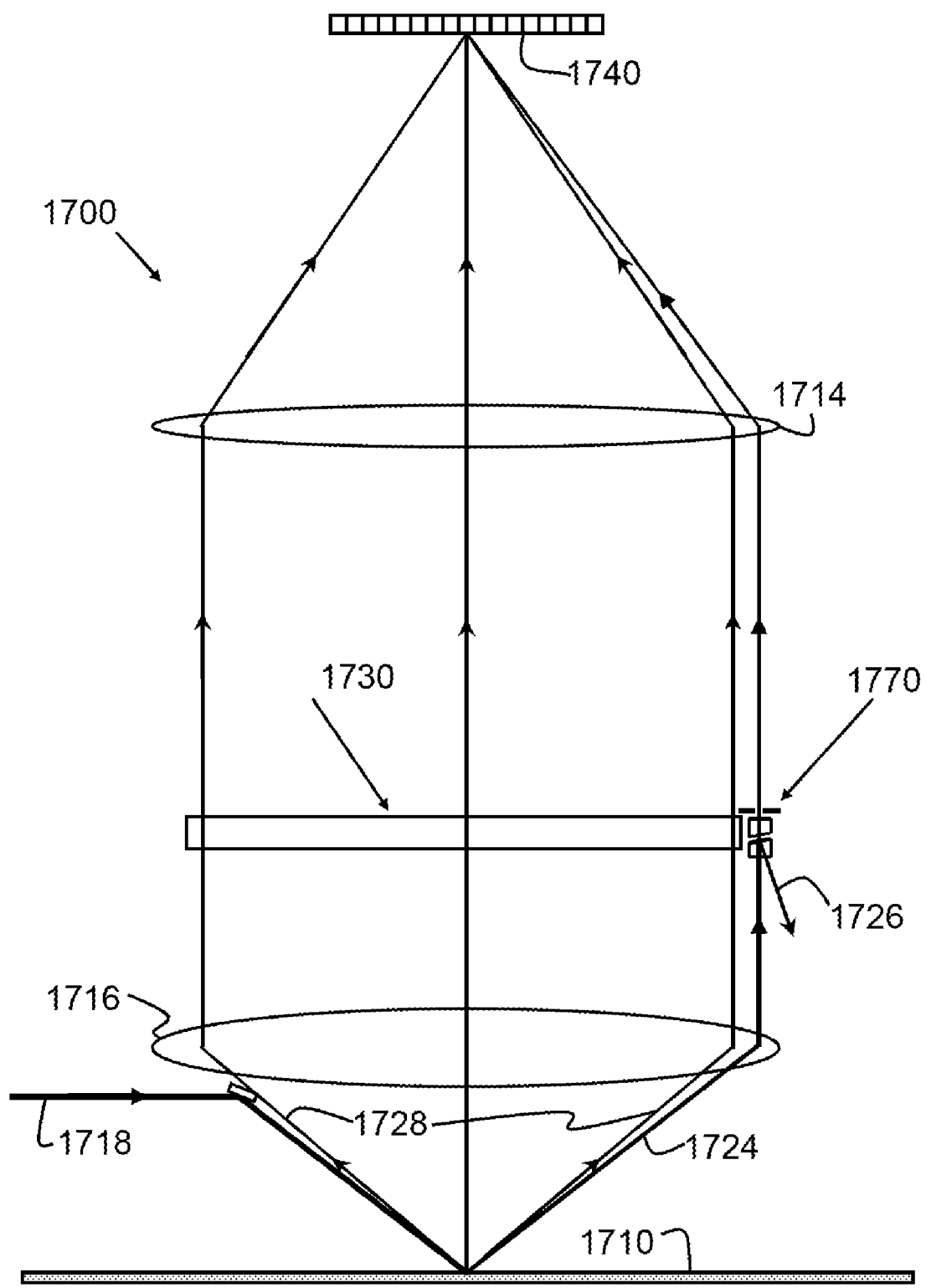
FIG. 17 shows an example of an interferometric defect detection system with a low-flare high-incidence angle illumination, according to some embodiments.

FIG. 17 shows an example of an interferometric defect detection system with a low-flare high-incidence angle illumination, according to some embodiments. Interferometric defect detection system 1700, includes an illumination source beam 1718 which is directed towards the surface of the sample 1710 as shown. The sample 1710 can be a wafer, reticle, or other sample being inspected. The scattered component from sample 1710 is represented by beams 1728, and the specular component is represented by beam 1724. A high-resolution optical system including lens systems 1714 and 1716 collects both the scattered and specular components of light and directs them to an image sensor 1740. Subsystem 1770 is positioned in the path of specular component 1724 and includes a phase controller and attenuator such as described and shown with respect to FIGS. 2a and 2b. Scattered light beams 1728 are passed through a compensation plate 1730 to compensate for path length differences between the specular and scattered components. A beam dump 1726 represents the portion of specular component 1724 that is attenuated by the attenuator.

Figure 18:
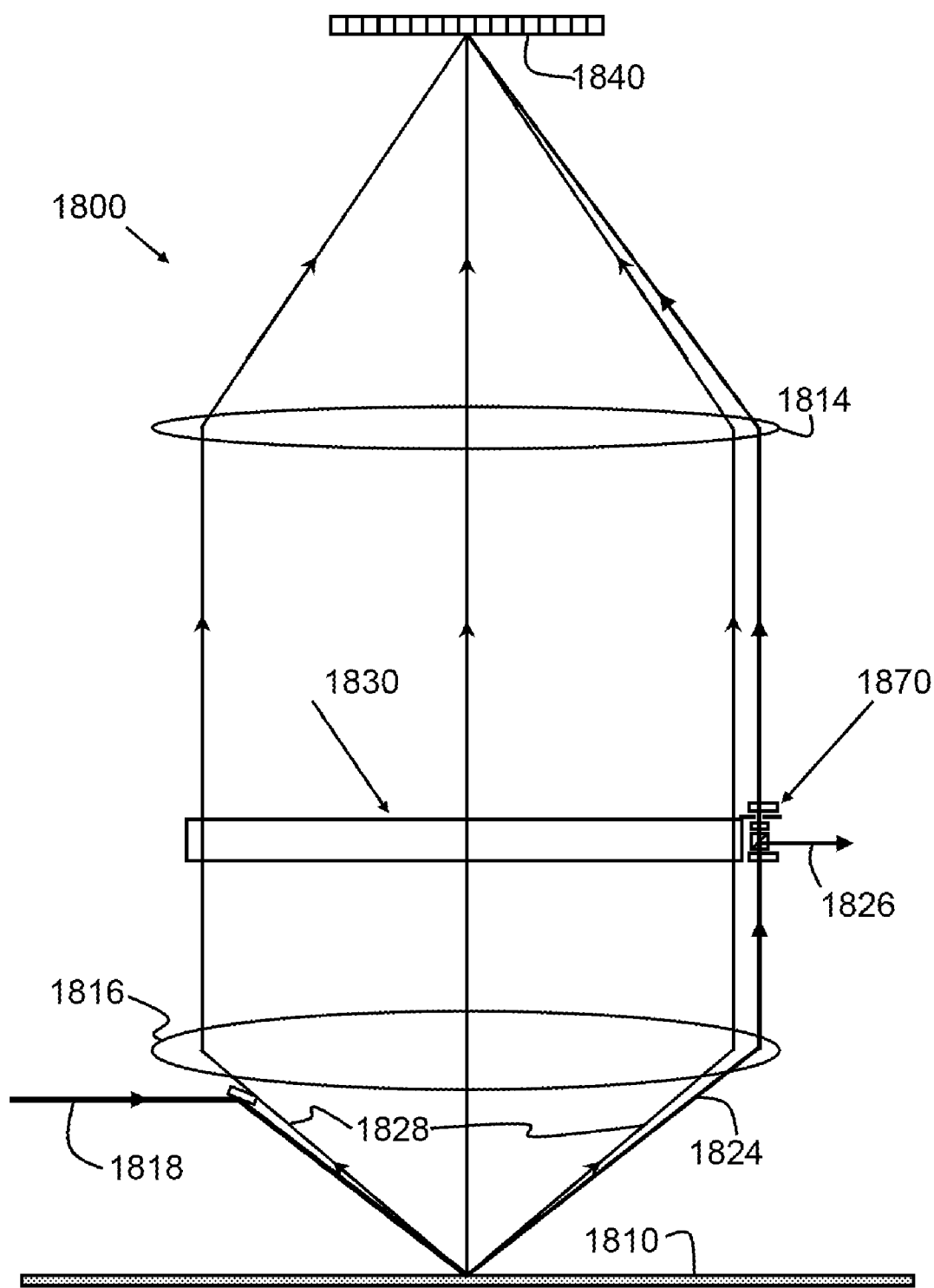
FIG. 18 shows an example of an interferometric defect detection system with low-flare high-incidence angle illumination and a variable attenuator, according to some embodiments.

FIG. 18 shows an example of an interferometric defect detection system with low-flare high-incidence angle illumination and a variable attenuator, according to some embodiments. Interferometric defect detection system 1800, includes an illumination source beam 1818 which is directed towards the surface of the sample 1810 as shown. The sample 1810 can be a wafer, reticle, or other sample being inspected. The scattered component from sample 1810 is represented by beams 1828, and the specular component is represented by beam 1824. A high-resolution optical system including lens systems 1814 and 1816 collects both the scattered and specular components of light and directs them to an image sensor 1840. Subsystem 1870 is positioned in the path of specular component 1824 and includes a phase controller and variable attenuator such as described and shown with respect to FIGS. 9-11 and 14. Scattered light beams 1828 are passed through a compensation plate 1830 to compensate for path length differences between the specular and scattered components. A beam dump 1826 represents the portion of specular component 1824 that is attenuated by the variable attenuator.

As shown in FIGS. 15 through 18, by shifting the beam location toward the edge at the pupil plane/aperture stop or feed illumination light externally, the high incidence angle of illumination can be achieved. An external feeding of the illumination light will reduce the stray light significantly. All the aforementioned techniques of phase control, amplitude attenuation, and polarization control of the specular component can be employed.

Figure 19:
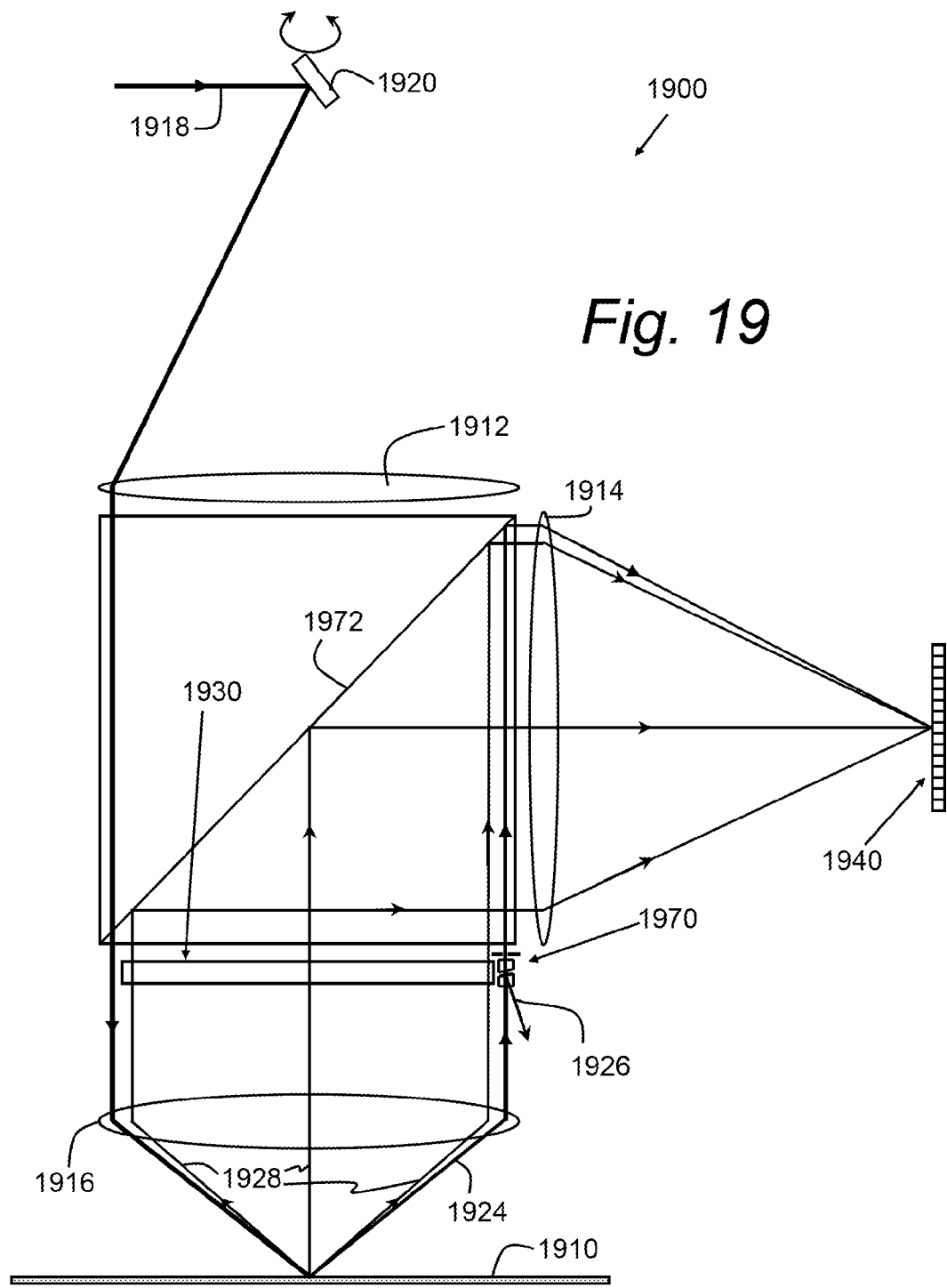
FIG. 19 shows an example of an interferometric defect detection system with an azimuthally rotatable high incidence angle illumination, according to some embodiments.
Figure 20:
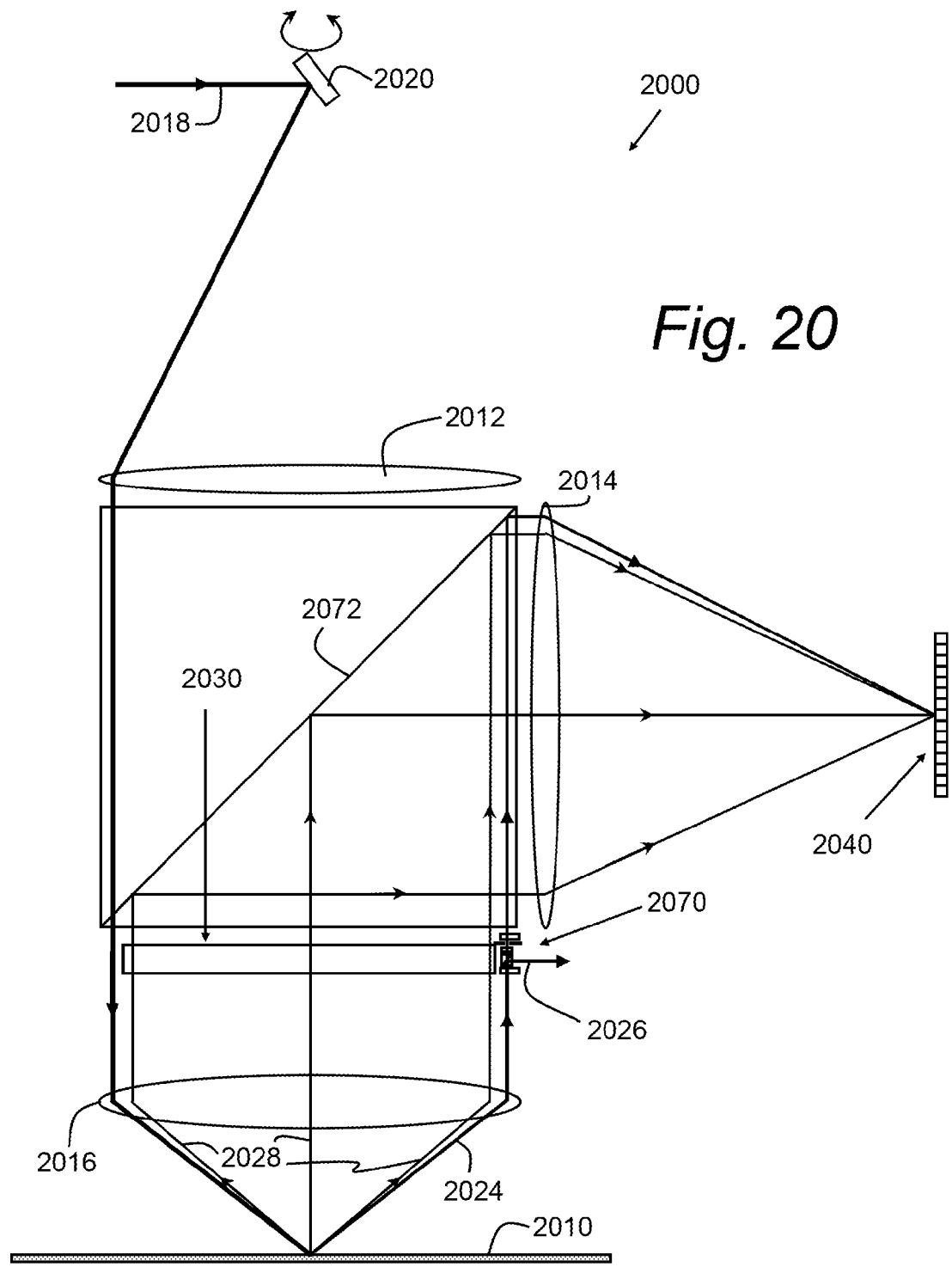
FIG. 20 shows an example of an interferometric defect detection system with an azimuthally rotatable high incidence angle illumination with a variable attenuator for the specular component, according to some embodiments.

11. Azimuthal Rotation of Illumination Light. Defect detection sensitivity generally depends not only on the polar angle but also on the azimuthal angle of incidence of the illumination light. In order to maximize the defect detection sensitivity, for some applications it is desirable to be able to put the illumination at any azimuthal angle of incidence. An effective way of covering all azimuthal angle of incidence is to put a rotatable prism or mirror at the conjugate location of the sample. This scheme is shown in FIGS. 19 through 22. The configuration of FIGS. 19 and 20 is more flexible because the illumination system and collection system share only the high power part of lens system.

FIG. 19 shows an example of an interferometric defect detection system with an azimuthally rotatable high incidence angle illumination, according to some embodiments. Interferometric defect detection system 1900, includes an illumination source beam 1918 which is directed towards a rotatable surface 1920 such as a mirror or prism. The reflected beam passes through lens system 1912 and is directed towards the surface of the sample 1910 as shown. The sample 1910 can be a wafer, reticle, or other sample being inspected. The scattered component from sample 1910 is represented by beams 1928, and the specular component is represented by beam 1924. A high-resolution optical system including lens systems 1914 and 1916, and beam splitter 1972 collects both the scattered and specular components of light and directs them to an image sensor 1940. Subsystem 1970 is positioned in the path of specular component 1924 and includes a phase controller and attenuator such as described and shown with respect to FIGS. 2a and 2b. Scattered light beams 1928 are passed through a compensation plate 1930 to compensate for path length differences between the specular and scattered components. A beam dump 1926 represents the portion of specular component 1924 that is attenuated by the attenuator.

FIG. 20 shows an example of an interferometric defect detection system with an azimuthally rotatable high incidence angle illumination with a variable attenuator for the specular component, according to some embodiments. Interferometric defect detection system 2000, includes an illumination source beam 2018 which is directed towards a rotatable surface 2020 such as a mirror or prism. The reflected beam passes through lens system 2012 and is directed towards the surface of the sample 2010 as shown. The sample 2010 can be a wafer, reticle, or other sample being inspected. The scattered component from sample 2010 is represented by beams 2028, and the specular component is represented by beam 2024. A high-resolution optical system including lens systems 2014 and 2016, and beam splitter 2072 collects both the scattered and specular components of light and directs them to an image sensor 2040. Subsystem 2070 positioned in the path of specular component 2024 and includes a phase controller and variable attenuator such as described and shown with respect to FIGS. 9-1*l* and 14. Scattered light beams 2028 are passed through a compensation plate 2030 to compensate for path length differences between the specular and scattered components. A beam dump 2026 represents the portion of specular component 2024 that is attenuated by the variable attenuator.

Figure 21:
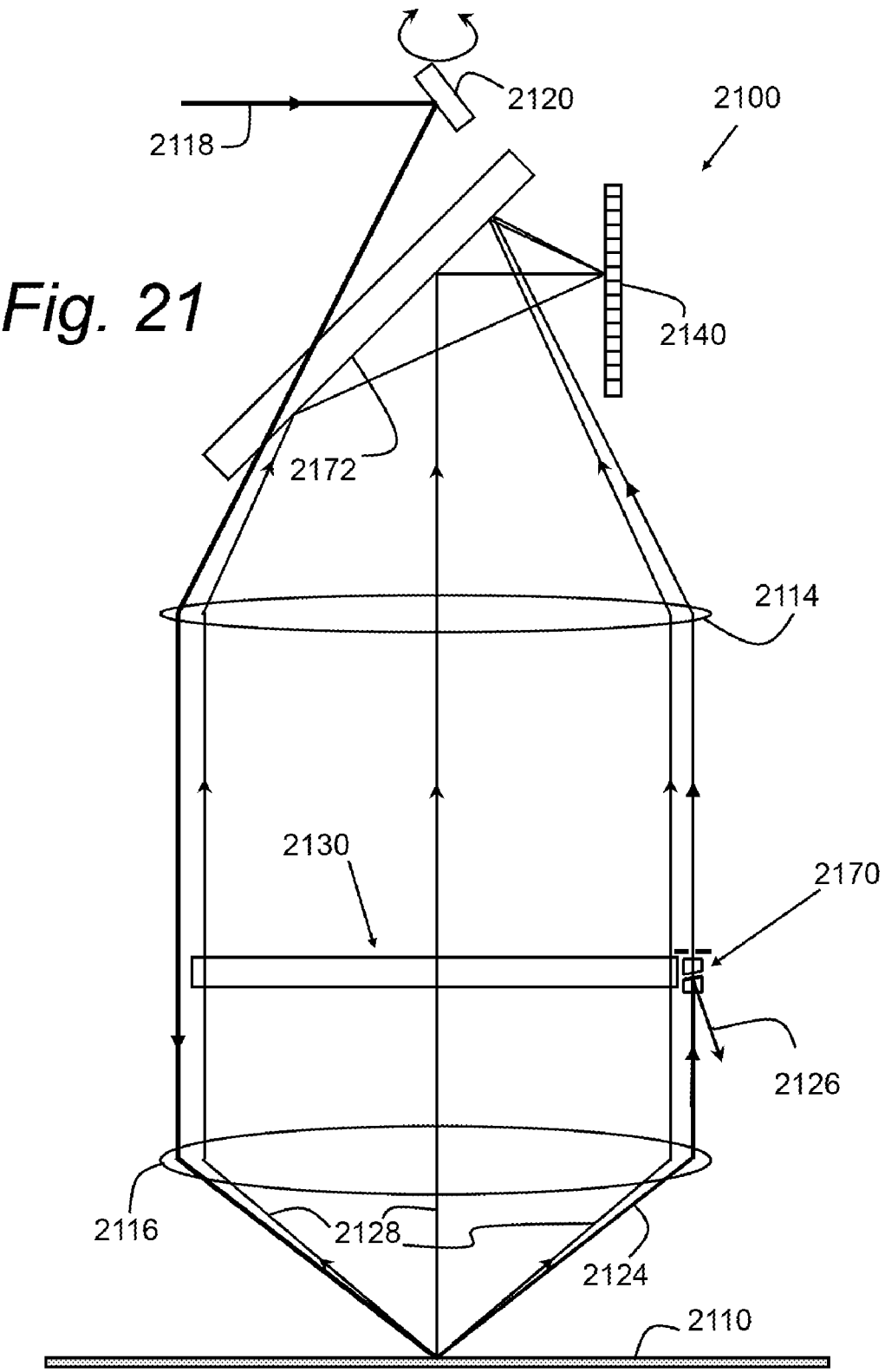
FIG. 21 shows an example of an interferometric defect detection system with an azimuthally rotatable high incidence angle illumination, according to some embodiments.
Figure 22:
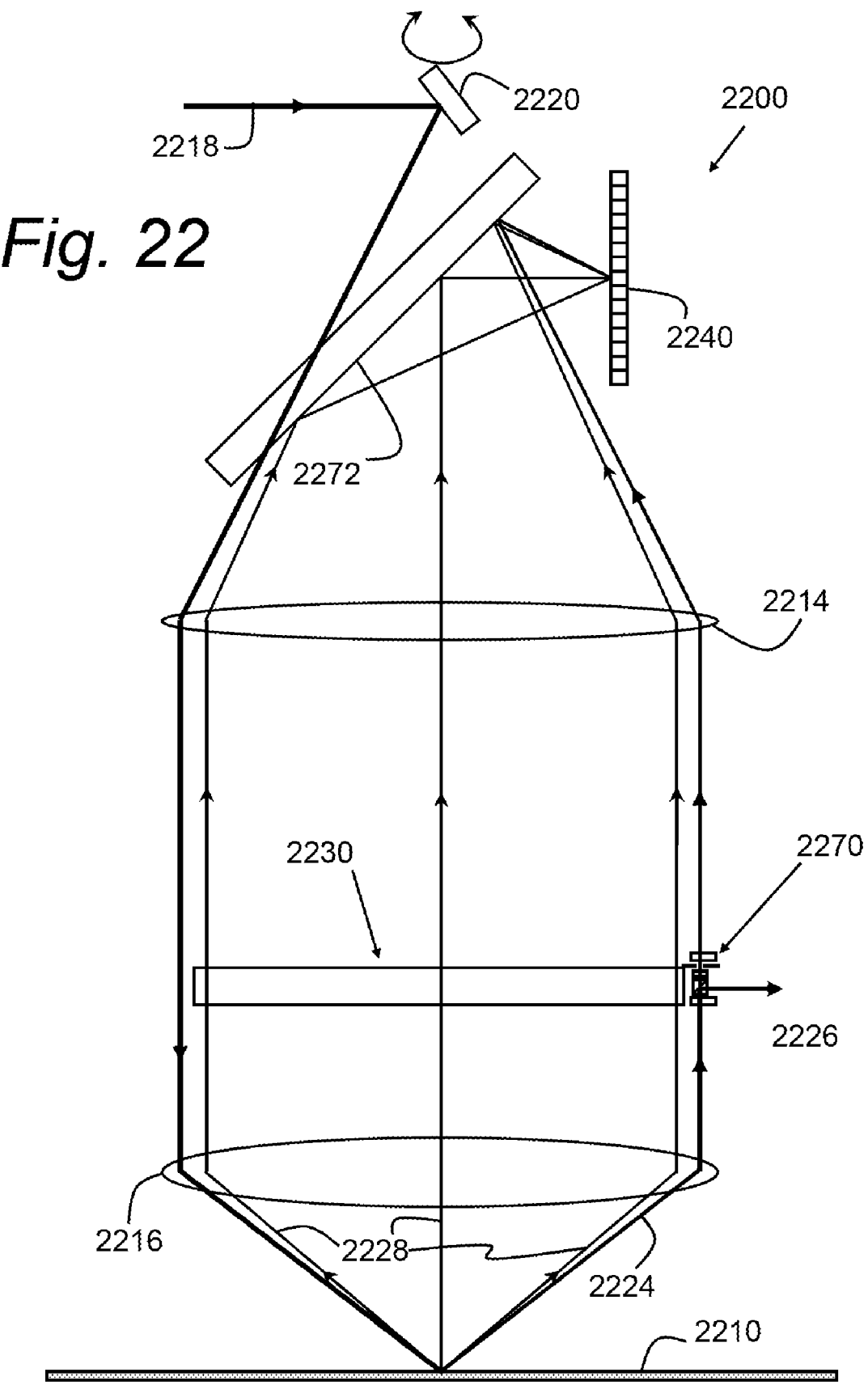
FIG. 22 shows an example of an interferometric defect detection system with an azimuthally rotatable high incidence angle illumination with a variable attenuator for the specular components according to some embodiments.

For some applications, especially in large etendue systems, there may be very little space available in the middle section of lens system for the beam splitter. In this case, the beam splitter can be positioned where more space is usually available. FIGS. 21 and 22 show this configuration. FIG. 21 shows an example of an interferometric defect detection system with an azimuthally rotatable high incidence angle illumination, according to some embodiments. Interferometric defect detection system 2100, includes an illumination source beam 2118 which is directed towards a rotatable surface 2120 such as a mirror or prism. The reflected beam is directed towards the surface of the sample 2110 as shown. The sample 2110 can be a wafer, reticle, or other sample being inspected. The scattered component from sample 2110 is represented by beams 2128, and the specular component is represented by beam 2124. A high-resolution optical system including lens systems 2114 and 2116, and beam splitter 2172 collects both the scattered and specular components of light and directs them to an image sensor 2140. Subsystem 2170 is positioned in the path of specular component 2124 and includes a phase controller and attenuator such as described and shown with respect to FIGS. 2a and 2b. Scattered light beams 2128 are passed through a compensation plate 2130 to compensate for path length differences between the specular and scattered components. A beam dump 2126 represents the portion of specular component 2124 that is attenuated by the attenuator.

FIG. 22 shows an example of an interferometric defect detection system with an azimuthally rotatable high incidence angle illumination with a variable attenuator for the specular component, according to some embodiments. Interferometric defect detection system 2200, includes an illumination source beam 2218 which is directed towards a rotatable surface 2220 such as a mirror or prism. The reflected beam is directed towards the surface of the sample 2210 as shown. The sample 22 10 can be a wafer, reticle, or other sample being inspected. The scattered component from sample 2210 is represented by beams 2228, and the specular component is represented by beam 2224. A high-resolution optical system including lens systems 2214 and 2216, and beam splitter 2272 collects both the scattered and specular components of light and directs them to an image sensor 2240. Subsystem 2270 positioned in the path of specular component 2224 and includes a phase controller and variable attenuator such as described and shown with respect to FIGS. 9-11 and 14. Scattered light beams 2228 are passed through a compensation plate 2230 to compensate for path length differences between the specular and scattered components. A beam dump 2226 represents the portion of specular component 2224 that is attenuated by the variable attenuator.

By rotating the prism or mirror located conjugate place of the sample, it is in principle possible to rotate the azimuthal angle of incidence of illumination light by 360 degrees. However, a 360 degree azimuthal rotatability of illumination light is rather difficult to achieve in practice because of mechanical collisions with other mechanical or optical parts. According to some embodiments, a 180 degree azimuthal rotation of illumination light is used. In these cases, 360 degree coverage of azimuthal rotation of illumination light relative to the sample is achieved by rotating the sample by 180 degrees. A 180 degree rotation of the sample usually does not cause any problems because the patterns on the wafers or reticles are predominantly oriented in 0°-180° or 90°-270° directions. An azimuthal rotation of the illumination beam can be very effective for the increase of the defect detection sensitivity if it is combined with polarization control. Polarization control of illumination is not mechanically coupled with azimuthal rotation of illumination light. Therefore, the combination of the two controls can be implemented without difficulty. Note that when azimuthal rotation of illumination light is used, the phase controller in the path of the specular component should also be azimuthally rotated in a synchronized fashion with the azimuthal rotation of the illumination light.

Figure 23:
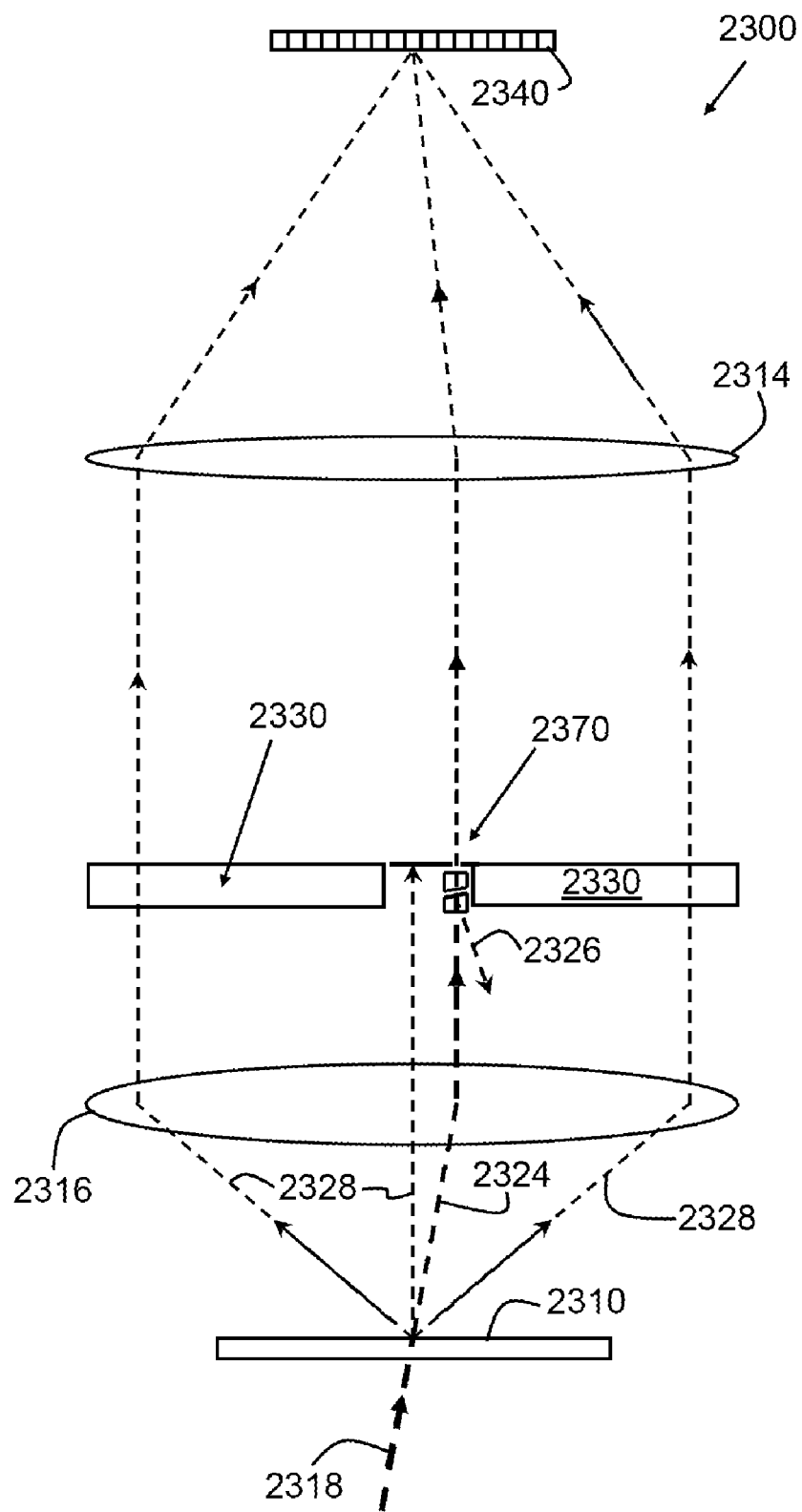
FIG. 23 shows an example of an interferometric defect detection system with illumination through transmissive samples, according to some embodiments.

12. Transmissive Configuration. Some samples like biological tissues can be transmissive rather than reflective. In order to inspect transmissive samples, the system should be configured into transmission mode. FIG. 23 shows an example of an interferometric defect detection system with illumination through transmissive samples, according to some embodiments. The only significant difference from the embodiments previously described is the illumination path. Other aspects remain the same. Interferometric defect detection system 2300, includes an illumination source which generates a coherent beam 2318. Beam 2318 is directed towards the transmissive sample 2310 as shown. The sample 2310 can be, for example a reticle or a biological sample being inspected. The scattered component from sample 2310 is represented by beams 2328, and the specular component is represented by beam 2324. A high-resolution optical system including lens systems 2314 and 2316 collects both the scattered and specular components of light and directs them to an image sensor 2340. Subsystem 2370 is positioned in the path of specular component 2324 and can includes a phase controller, attenuator, and/or one or more polarization controllers such as described and shown with respect to FIGS. 2a-b, 9-11 and 14. Scattered light beams 2328 are passed through a compensation plate 2330 to compensate for the path length difference between the specular and scattered components. A beam dump 2326 represents the portion of specular component 2324 that is attenuated by the variable attenuator.

Most reticles are both transmissive and reflective. However, they are usually used in transmission mode. In this case, only the transmission, not the reflectivity, of the reticle is of the final concern. Unlike conventional reticle inspection tools, the complex transmission coefficient of reticle can be determined by measuring both amplitude and phase of the transmitted light. Therefore, the transmissive configuration described herein can be used for reticle inspection very effectively in terms of both performance and cost.

Figure 24:
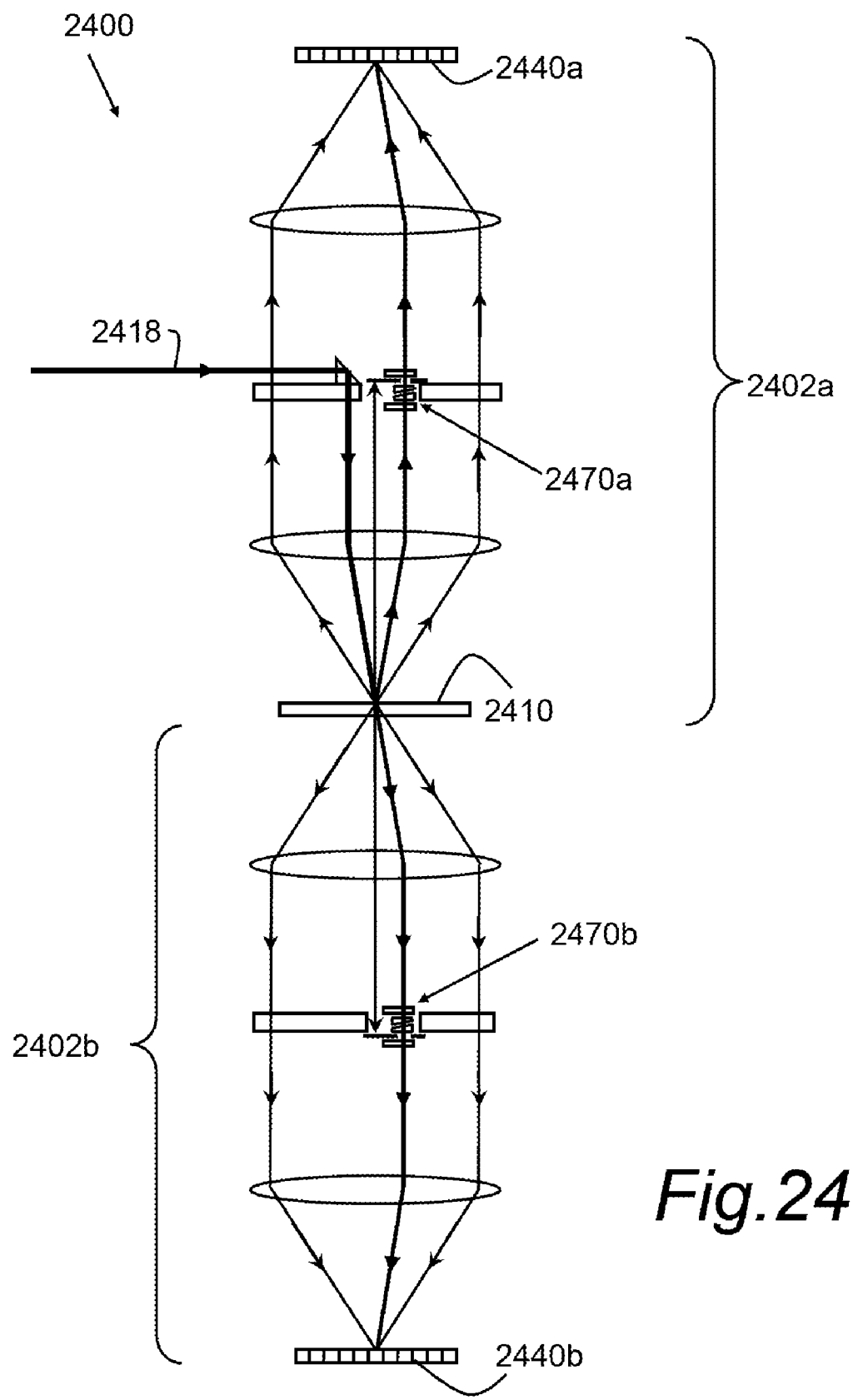
FIG. 24 shows an example of a sample inspection system incorporating both reflection and transmission modes, according to some embodiments.

13. Dual Mode Configuration. Some samples can be both reflective and transmissive. A good example is reticle. In order to inspect this kind of sample in a more thorough fashion, the system needs to incorporate both reflection and transmission modes at the same time. An example configuration of this kind of systems is shown in FIG. 24. System 2400 includes a reflective subsystem 2402a and a transmissive subsystem 2402b. A single source beam 2418 is directed toward sample 2410, which is, for example, a reticle. The reflected and transmitted lights are detected by two separate image sensors 2440a and 2440b simultaneously. Phase control and attenuation are achieved through each respective subsystem 2470a and 2470b. There is no change of working principles from those previously described herein. All aforementioned controls of phase, amplitude and polarization can be implemented. In case of reticle inspection, die-to-die image subtraction technique cannot be used. The image of defect-free reticle must be generated from reticle data by computer. Then, the image of actual reticle is compared with the computer-generated image of defect-free reticle to find defects. In order to facilitate fast data processing, image of defect-free reticle must be generated fast. A fully coherent illumination source such as a laser minimizes the amount of computations required for reticle image construction, thus allowing fast image construction with minimal computational resources.

14. Multiple Wavelength Configurations

The detection sensitivity of some defects depends on the wavelength used. Therefore for some applications, multiple wavelengths can be used to more effectively detect a variety of defects. According to some embodiments, multiple wavelengths can be implemented cost-effectively in either sequentially-operational or simultaneously-operational configuration.

Figure 25:
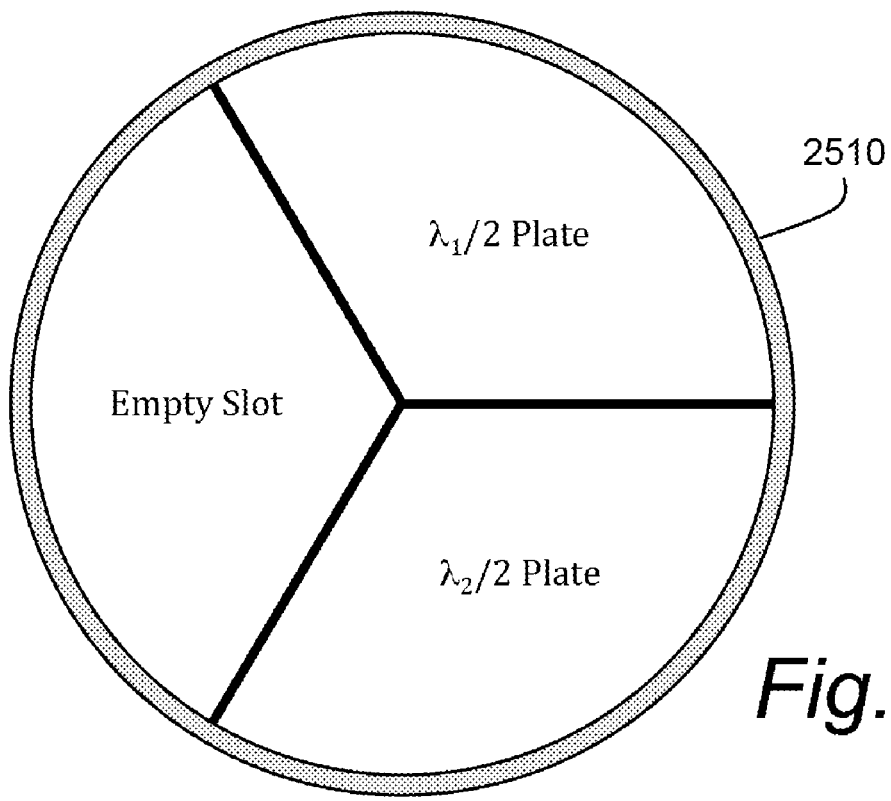
FIGS. 25 through 27 show various examples of waveplates for use in operation of a detection system in a sequential multiple wavelength mode, according to some embodiments.
Figure 26:
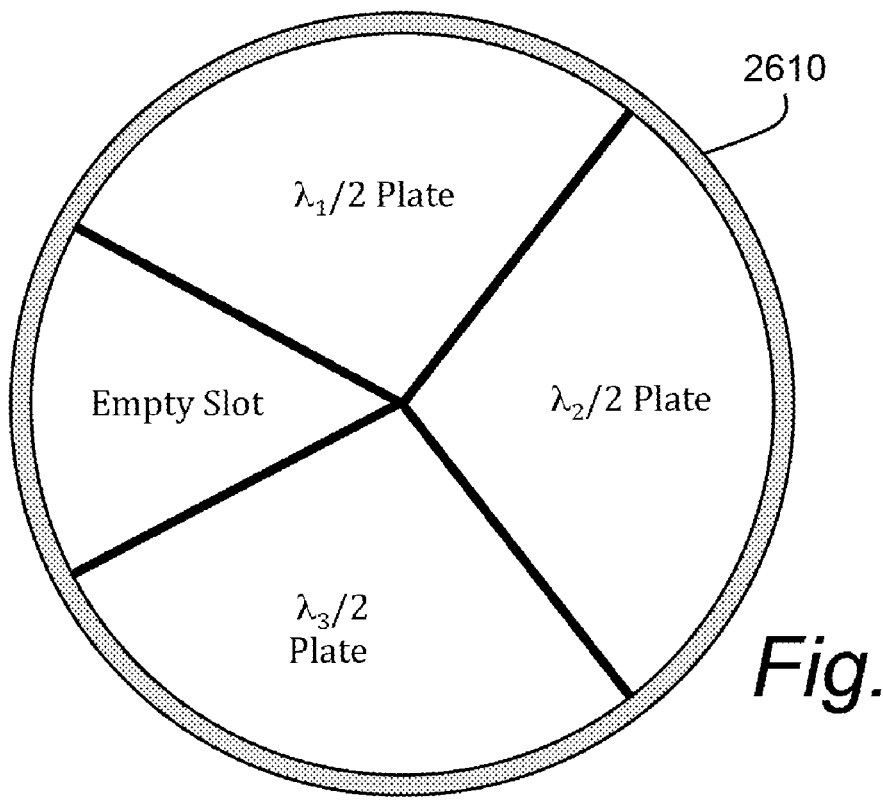
Figure 27:
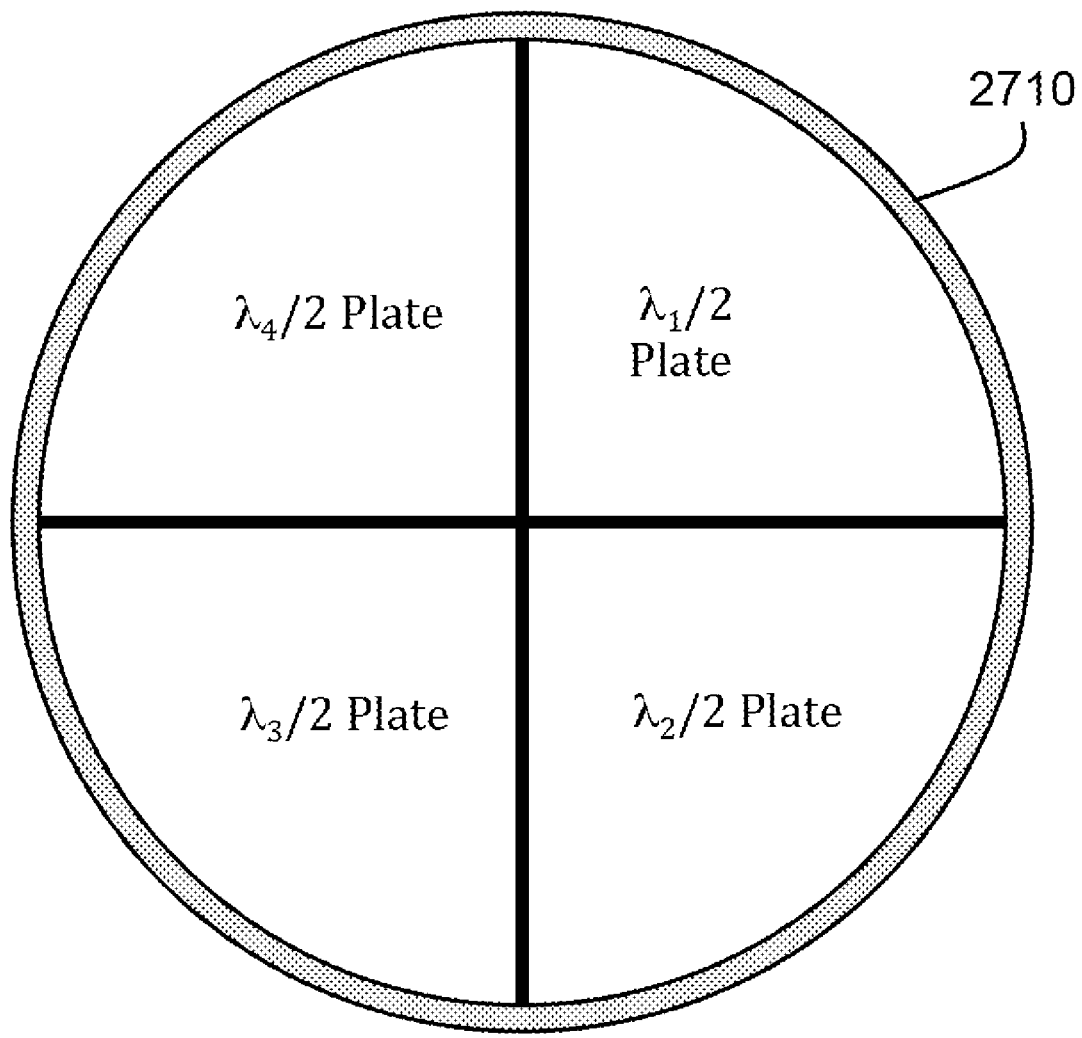

Sequential Multiple Wavelengths: In this configuration, only one image sensor needs to be used and one wavelength at a time is used to detect defects. The hardware is simpler but the operation takes more time compared with the configuration for the simultaneous multiple wavelength operation. The phase controller does not need to be modified but wave plates for amplitude attenuation and polarization control are modified to be able to handle multiple wavelengths. FIGS. 25 through 27 show some possible modifications of $\lambda/2$ plates. FIG. 25 shows an example of a $\lambda/2$ wave plate 2510 for two wavelengths. FIG. 26 shows an example of a $\lambda/2$ wave plate 2610 for three wavelengths. FIG. 27 shows an example of a $\lambda/2$ wave plate 2710 for four wavelengths. Modifications analogous to those shown in FIGS. 25-27 can be applied to $\lambda/4$ plates. When the wavelength is switched, the wave plates need to be switched accordingly. Wave plate switching is achieved by rotating the modified waveplate by an appropriate amount. The wave plates are rotated by a maximum of 90° to cover all possible amplitude attenuation and polarization states. Therefore, a maximum of four wave plates for four different wavelengths can be packaged in a single mount as shown in FIG. 27. If the beam size is not very small compared with the area of each wave plate, two or three plates in the single mount, as shown in FIGS. 25 and 26, is more practical.

Figure 28:
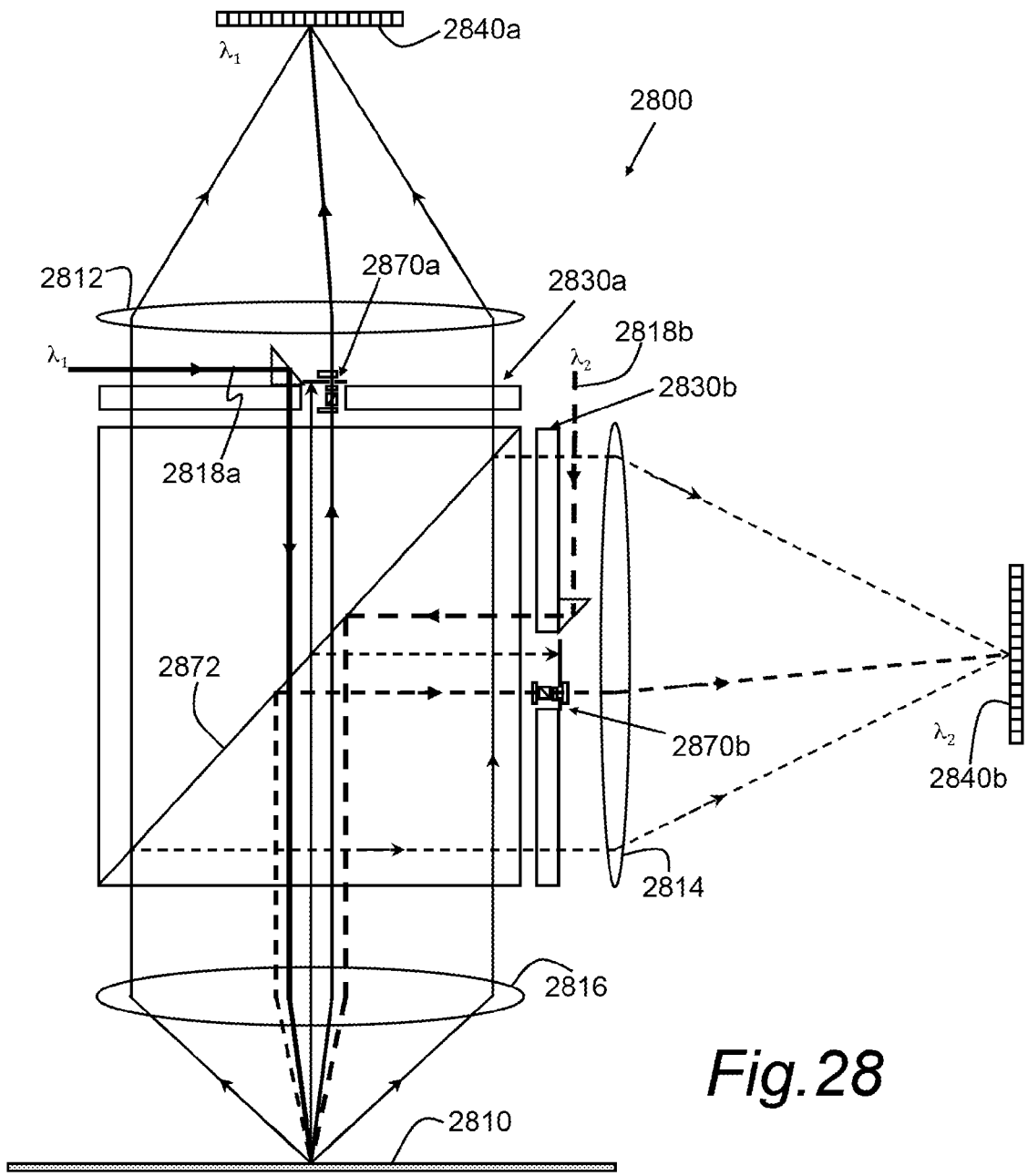
FIG. 28 shows an example system configuration for two wavelengths, according to some embodiments.

Simultaneous Multiple Wavelengths: Multiple wavelengths can be used simultaneously by adding a wavelength splitter and a separate image sensor for each wavelength. FIG. 28 shows an example system configuration for two wavelengths, according to some embodiments. System 2800 for inspection of sample 2810 uses two separate illumination source beams 2818a and 2818b having two different wavelengths. The two wavelengths are combined and separated by a wavelength splitter 2872. Two wavelengths share the same front end of the collection optics 2816 which is usually the most critical and also the most expensive part of the whole optical system. By sharing the front end of the collection optics 2816, the system achieves not only simplicity but also stability. The back-end components 2812 and 2814 which are usually of low optical power and less expensive are separated in order to give maximum flexibilities in phase control, magnification adjustments, and sensor choices. Subsystems 2870a and 2870b are used to control the phase and attenuation such as shown and described with respect to FIGS. 2a-b, 9-11 and 14. Each wavelength also uses its own compensation plate 2830a and 2830b, and image sensor 2840a and 2840b. According to some embodiments, 266 nm and 532 nm are used for the two wavelengths. The technology for producing these two wavelengths is mature and a single laser system can provide both wavelengths, thus reducing cost. According to some embodiments, more than two wavelengths are implemented by adding more wavelength splitters in the back-end optical paths.

Figure 29:
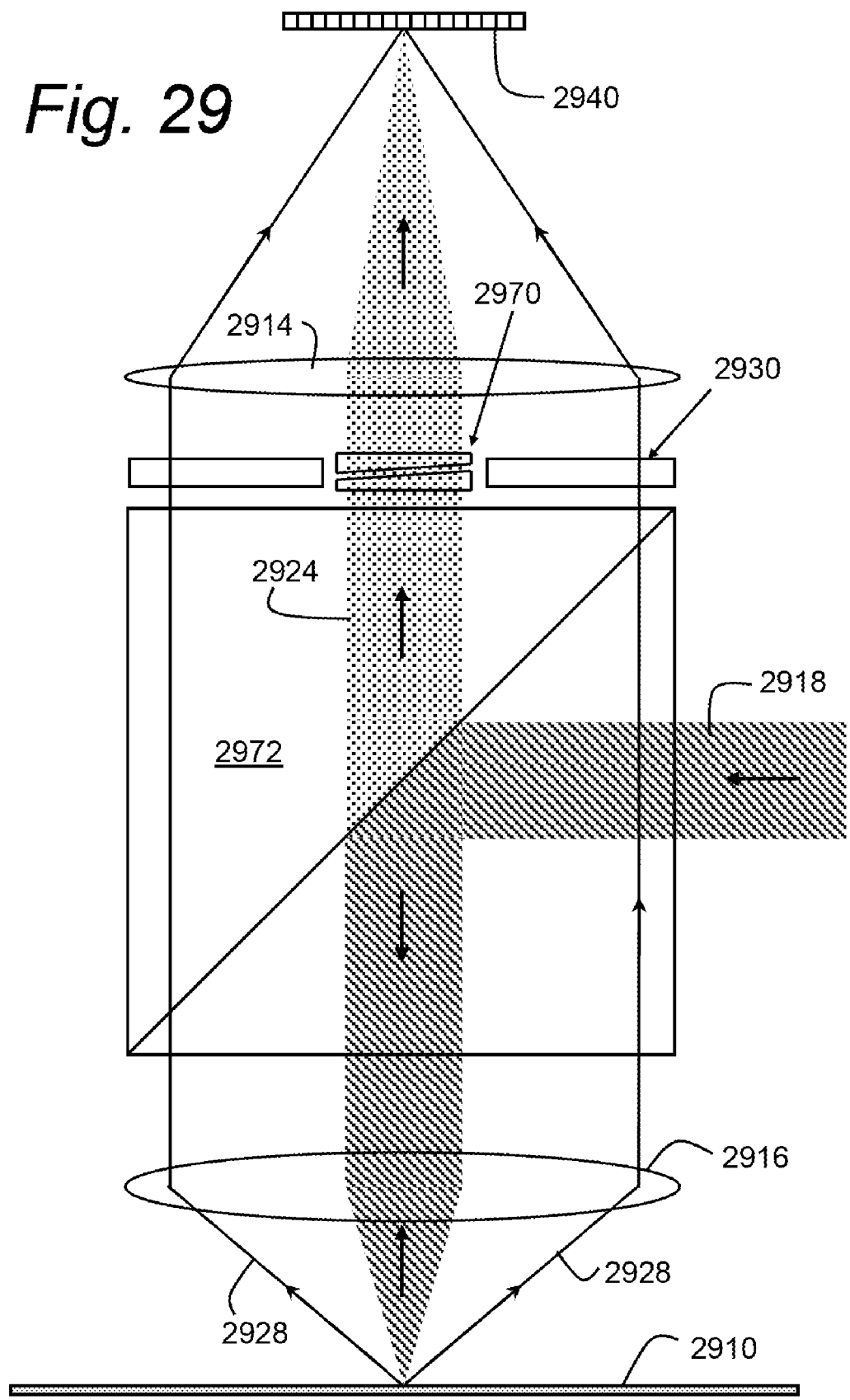
FIG. 29 shows an example of an interferometric defect detection system having a low incidence angle illumination with an extended light source, according to some embodiments.
Figure 30:
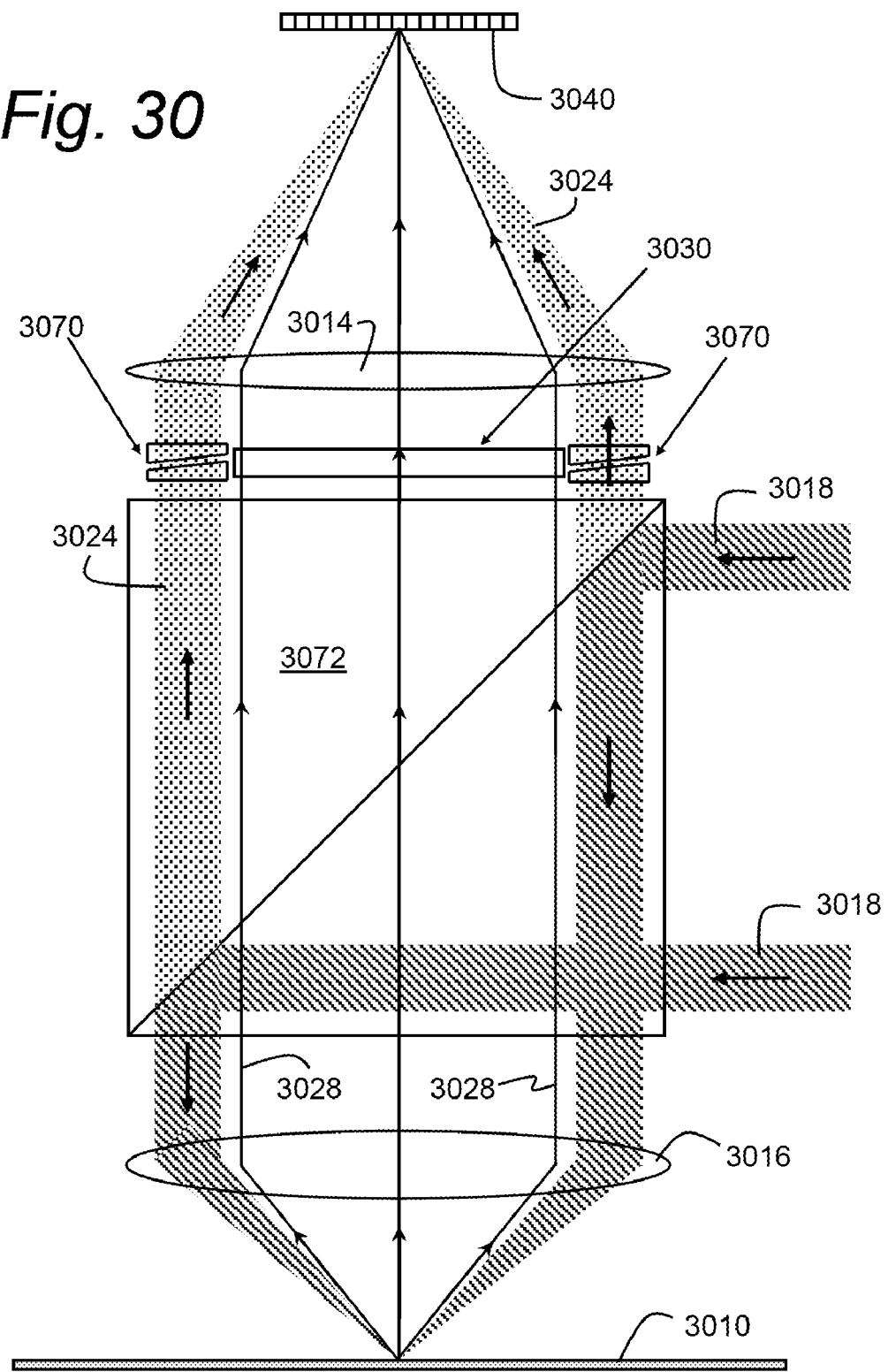
FIG. 30 shows an example of an interferometric defect detection system having a high incidence angle illumination with an extended light source, according to some embodiments.
Figure 31:
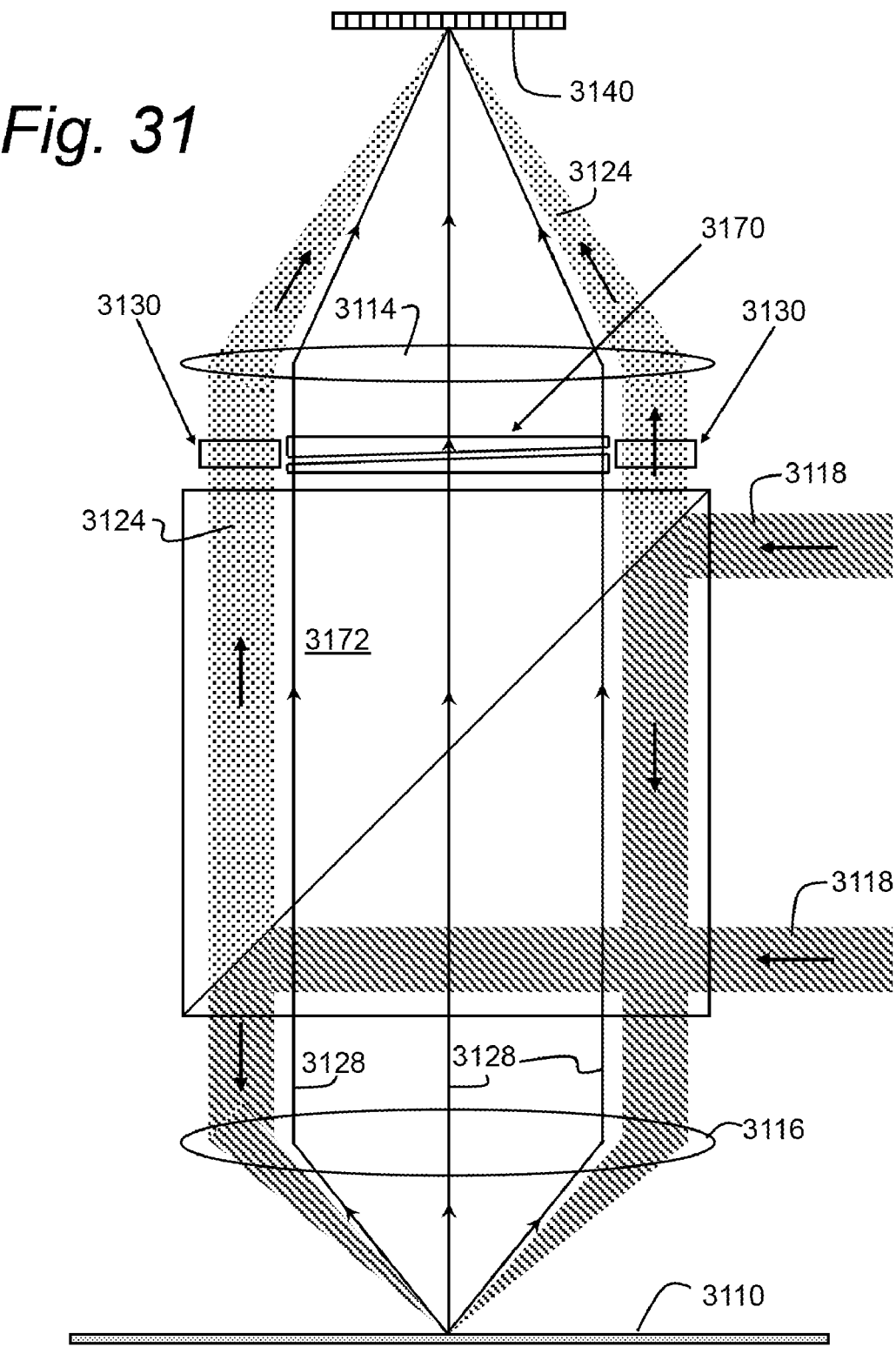
FIG. 31 shows an example of an interferometric defect detection system having a high incidence angle illumination with an extended light source and phase control in the path of the scattered light, according to some embodiments.

15. Extended Source. For many applications lasers in coherent illumination mode are the preferred light sources as previously discussed. However, according to some embodiments light sources other than lasers can also be used. For example, an extended source like an arc lamp can be used as shown in FIGS. 29 through 31. FIG. 29 shows an example of an interferometric defect detection system having a low incidence angle illumination with an extended light source, according to some embodiments. Incoming light beam 2918 is directed toward sample 2910 using beam splitter 2972. The specular reflected component is represented by beam 2924 and passes through a phase controller and attenuator 2970 that is analogous to any of the subsystems shown and described with respect to FIGS. 2a-b, 9-11 and 14. The scattered component represented by beams 2928 pass through compensation plate 2930. Front end optical system 2916 and back end optical system 2914 collect and direct the light towards imaging sensor 2940.

FIG. 30 shows an example of an interferometric defect detection system having a high incidence angle illumination with an extended light source, according to some embodiments. Incoming light beams 3018 are directed toward sample 3010 using beam splitter 3072. The specular reflected component is represented by beams 3024 and passes through a phase controllers and attenuators 3070 that are analogous to any of the subsystems shown and described with respect to FIGS. 2a-b, 9-11 and 14. The scattered component represented by beams 3028 pass through compensation plate 3030. Front end optical system 3016 and back end optical system 3014 collect and direct the light towards imaging sensor 3040.

FIG. 31 shows an example of an interferometric defect detection system having a high incidence angle illumination with an extended light source and phase control in the path of the scattered light, according to some embodiments. Incoming light beams 3118 are directed toward sample 3110 using beam splitter 3172. The specular reflected component is represented by beams 3124 and passes through a compensation plate 3130. The scattered component represented by beams 3128 pass though phase controllers and attenuators 3170 that are analogous to any of the subsystems shown and described with respect to FIGS. 2a-b, 9-11 and 14. Front end optical system 3116 and back end optical system 3114 collect and direct the light towards imaging sensor 3140.

An extended source has an advantage of spreading light energy over wider areas in the optical system. The spread of light energy reduces the possibility of material damage by high power density of the illumination light or specular component. However, there are disadvantages associated with extended light sources. For example, the collection of the signal light tends to be reduced. Also, it is generally more difficult to implement Fourier filters with extended sources.

III. Operation Modes. The Systems Described Herein can be Operated in Many Different Ways. Further Detail of Several Different Operation Modes will now be Provided.

1. High Sensitivity Mode. This mode targets specific types of defects. The relative phase between the scattered component and the specular component is usually set to maximize the defect signal. (The relative phase can also be set to minimize wafer pattern noise or maximize signal-to-noise ratio. But in most cases, these are very equivalent to each other.) If the detailed physical characteristics of the defect and surrounding circuit patterns is unknown, the ideal relative phase value should be determined experimentally. On the other hand, if their physical characteristics is known, the relative phase can be set based on theory or numerical simulations. Equation (3) shows that $\phi_s$, the relative phase between the defect signal amplitude and specular component, is important for maximizing the defect signal. It shows that extrema of the defect signal happen when $\phi_s=0°$ or 180°. However, if $\phi_s=0°$, the value of the interference term becomes positive and if $\phi_s=180°$, the value of the interference term becomes negative.

As mentioned previously, the total defect signal is composed of both dark field terms and the interference term. Therefore, in order to maximize the total defect signal, the sign of the interference term should be modified if necessary to be the same sign as the whole dark field term. The sign of the whole dark field term cannot be controlled. It can either be positive or negative depending on the physical characteristics of the defect and surrounding patterns. Therefore, there is no other way than controlling the phase of the interference term to get the maximum defect signal. If the sign of the whole dark field term is positive, the choice of $\phi_s=0°$ maximizes the total defect signal. If the sign of the whole dark field term is negative, the choice of $\phi_s=180°$ maximizes the total defect signal. They are confirmed by numerical simulations of defect signals. In order to show the benefit of the described techniques clearly, a realistic but simple defect is chosen for numerical simulations. Also, as mentioned previously, the relative phase can be varied by changing either the phase of the specular or scattered component. But, in practice it is much easier to change the phase of the specular component because the specular component has a lower etendue. Therefore, in all numerical simulations, the phase of the specular component is varied to get optimum relative phase values.

Figure 32A:
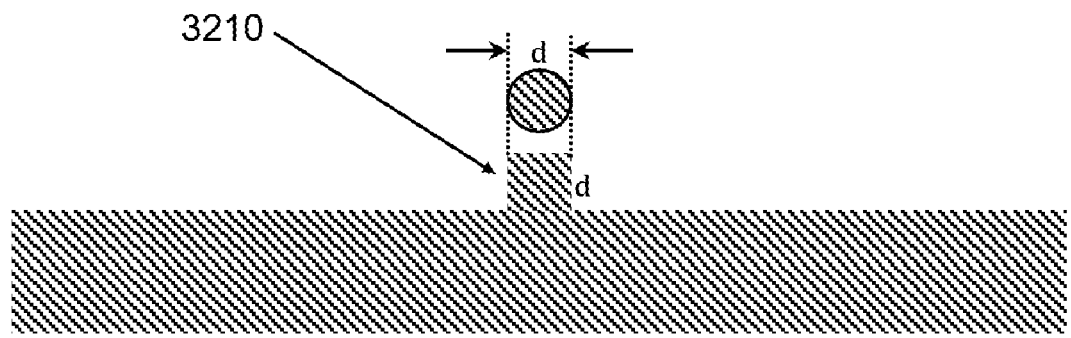
FIGS. 32a and 32b show the shapes of the defects used for numerical simulations herein.
Figure 32B:
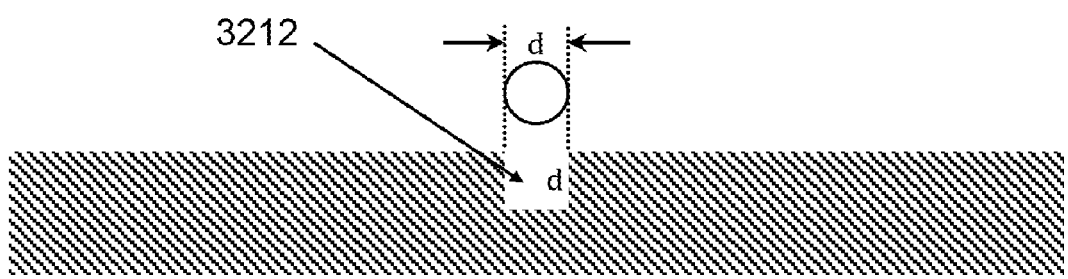

FIGS. 32a and 32b show the shapes of the defects used for numerical simulations herein. The defects are round-shaped having a height or depth the same as the diameter. FIG. 32a shows a particle type defect 3210 having a height and diameter of "d." FIG. 32b shows a void type defect 3212 having a depth and diameter of "d." The defect material is assumed to be the same as the sample material. These kinds of defects are called phase defects because they introduce phase change, not amplitude change, to the reflected light. A wavelength of 266 nm was used and a numerical aperture of the signal collection system was assumed to be 0.9. The central obscuration due to the phase controller and its mount was assumed to be 0.2, in terms of numerical aperture. Only particle type defects are chosen for defect signal simulations because void type defects will produce similar results with opposite signs on phase values.

Figure 33:
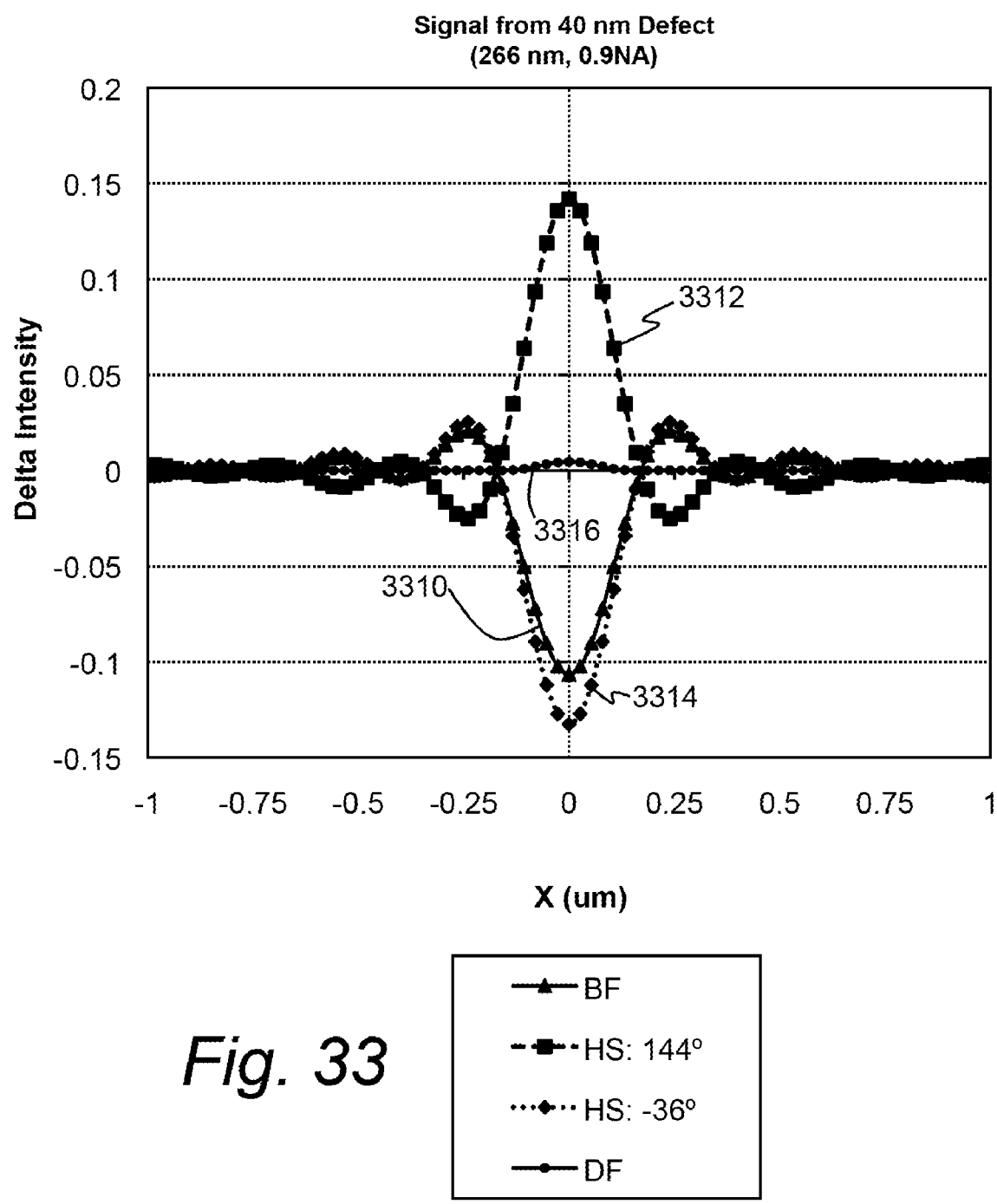
FIGS. 33 though 35 are graphs showing results of numerical simulations.
Figure 34:
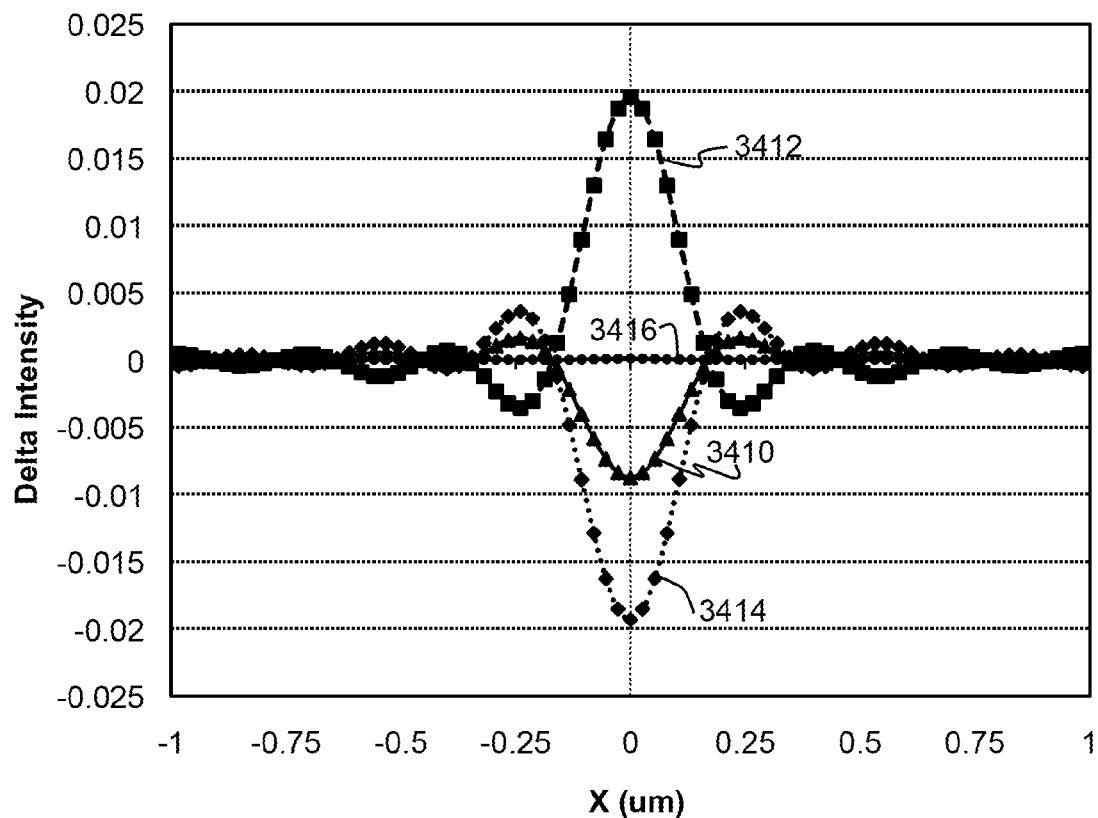
Figure 35:
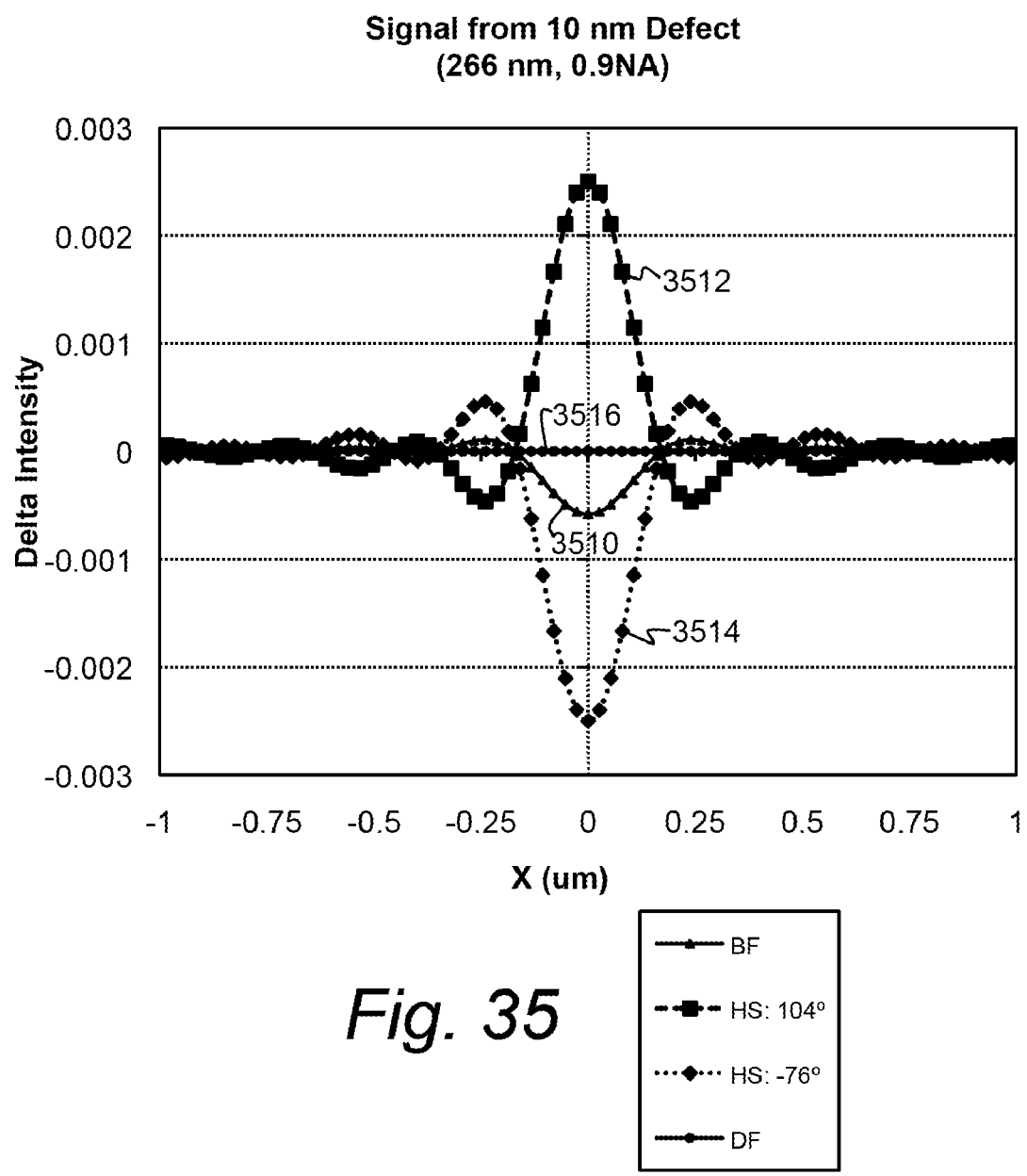

FIGS. 33-35 show the results of numerical simulation results. FIG. 33 shows simulation results for a 40 nm defect. Curve 3310 plots simulated results of a conventional bright field mode system. Curves 3312 and 3314 plot simulated results of the techniques described herein using a high sensitivity mode introducing phase angles of 144° and −36° to the specular component, respectively. Curve 3316 plots simulated results for a conventional dark field system. FIG. 34 shows simulation results for a 20 nm defect. Curve 3410 plots simulated results of a conventional bright field mode system. Curves 3412 and 3414 plot simulated results of the techniques described herein using a high sensitivity mode introducing phase angles of 117° and −63° to the specular component, respectively. Curve 3416 plots simulated results for a conventional dark field system. FIG. 35 shows simulation results for a 10 nm defect. Curve 3510 plots simulated results of a conventional bright field mode system. Curves 3512 and 3514 plot simulated results of the techniques described herein using a high sensitivity mode introducing phase angles of 104° and −76° to the specular component, respectively. Curve 3516 plots simulated results for a conventional dark field system. "BF" in the figure's legend means a conventional system using bright field mode. It is included in the figures for comparison purposes. "HS" in the figure's legend means high sensitivity mode. The angle values are the phase angles introduced to the specular component to get the two extrema of defect signals as mentioned previously. The positive angles correspond to $\phi_s=0°$ cases and negative angles correspond to $\phi_s=\pm 180°$ cases. (Note: $\phi_s$ is not the phase angle introduced to the specular component. $\phi_s$ is the sum of the phase angle introduced to the specular component and the innate phase angle difference between the defect signal and the specular component. The innate phase angle difference is the phase angle difference conventional bright field mode systems will have. The innate phase angle differences in the simulated defect signals are −144°, −117° and −104° for 40 nm, 20 nm and 10 nm defects respectively. These innate phase angle differences are quite different from 0° or ±180°. This is the reason why conventional bright field mode can perform neither well nor stably. The phase controller either adds (or subtracts) an appropriate amount of phase angle to make the total phase angle difference 0° or ±180°. In the simulated defect signals, the phase controller added 144°, 117° and 104° respectively to the innate signals from 40 nm, 20 nm, and 10 nm defects to make the total phase differences 0°. The phase controller also adds −36°, −63° and −76° respectively to the innate defect signals from 40 nm, 20 nm, and 10 nm defects to make the total phase difference −180°. The legends in the FIGS. 33 through 35 shows these phase angles the phase controller added to the innate phase angle differences. "BF" means no phase angle addition (or subtraction). Therefore, "BF" is equivalent to "HS:0°". Also, notice from the figures' legends that the difference between the two phase angles of two extreme defect signals is 180°.) "DF" in figures' legends represents dark field systems.

Several important facts can be derived from the simulation results. First, the strength of the dark field signal decreases very quickly as the size of the defect becomes smaller than a quarter of the wavelength. The dark field signal could be higher than those shown in the figures if it happens to interfere constructively with the scattered light by the surrounding patterns. But, that kind of interference is not controllable and relies completely on luck. Therefore, it is generally expected that the dark field defect signal will become too low to be detected reliably for defects whose size is smaller than a quarter of the wavelength. In the near future, a significant portion of critical defects in semiconductor wafers are expected to be much smaller than a quarter of the wavelength. Therefore, the future of current dark field technologies looks poor. Second, the required phase change on the specular component to make the relative phase between the defect signal and the specular component be 0° or 180° is not ±90°, even though the defects used in simulations are phase objects. Actually, the amount of phase change required on the specular component for a maximum defect signal depends on the size of the phase object. This is different than in the case of the phase-contrast microscopy where a fixed ±90° phase is added to the specular component for maximum image contrast. Even these simple examples show that continuous variability of the relative phase between the defect signal and the specular component is desirable for reliable defect detections. The techniques described herein employ a phase controller that can vary the relative phase in a continuous manner. Third, the defect signals are boosted or amplified significantly over the conventional bright field signal by varying the relative phase appropriately. Furthermore, the signal amplification becomes more significant when the defect size gets smaller. Another advantage of operating in a maximum defect signal mode is improved signal stability. This is because the first order signal sensitivity to external perturbation is zero if the signal intensity is an extremum. Thus, a much higher defect detection sensitivity with better stability can be provided.

Figure 36:
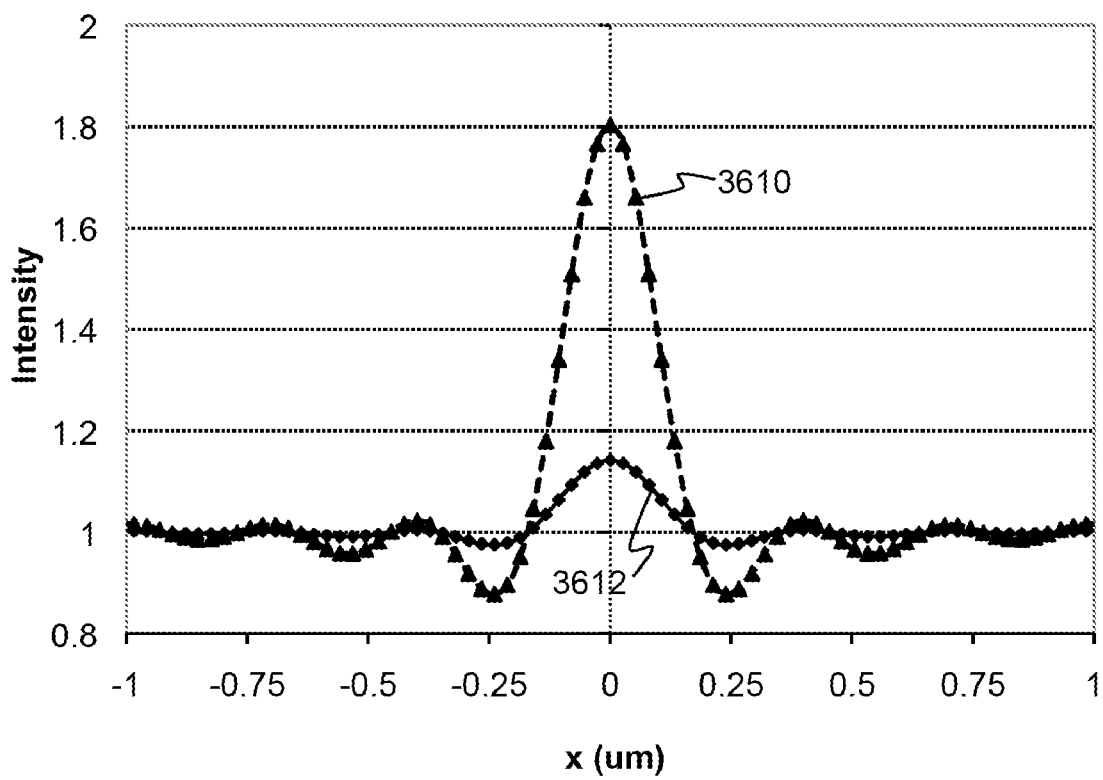
FIG. 36 shows plots of simulated enhanced contrast of an image of a 40 nm defect by attenuating the intensity of the specular component by 96%.
Figure 37:
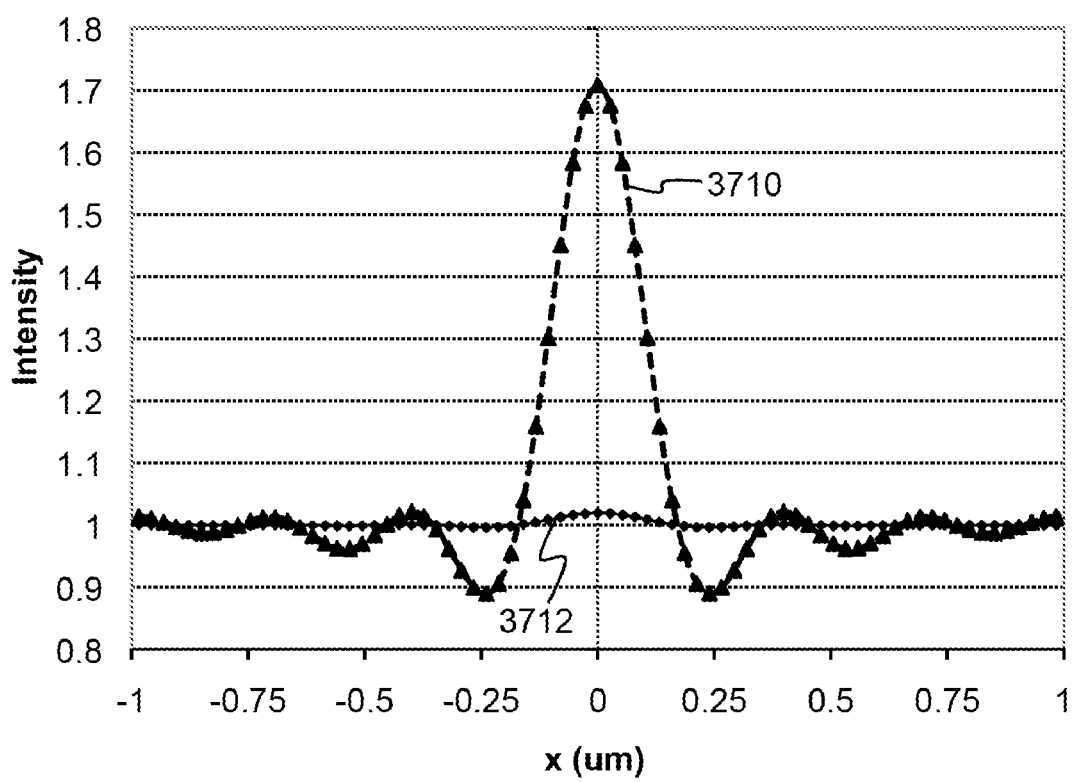
FIG. 37 shows plots of simulated enhanced contrast of an image of a 20 nm defect by attenuating the intensity of the specular component by 99.9%.

Contrast Enhancement. As stated previously, a strong specular component means high noiseless amplification of defect signal. High noiseless amplification of defect signals leads to high contrast of defect or subtracted images. The high contrast of defect or subtracted images leads to more sensitive and stable defect detection. Therefore, strong specular component is generally preferred herein. Note that strong specular component increases the contrast of subtracted images, but decreases the contrast of raw images. The contrast of concern for defect detection is the contrast of subtracted, not raw, images. This is quite the opposite of all conventional microscopies including phase-contrast types and all derivatives which care the contrast of raw images. However, too strong of a specular component can saturate the image sensor if its dynamic range is not very large and consequently distort defect signal. Therefore, when the dynamic range of image sensor is limited, the contrast of the raw sample image needs to be increased in order to avoid the distortion of the defect signal. If the defect or wafer pattern is much smaller than the wavelength, significant attenuation of the specular component may be useful in order to get suitably high enough image contrast. Numerical simulations confirm the effectiveness of this method of contrast enhancement. FIG. 36 shows an enhanced contrast of the image of a 40 nm defect by attenuating the intensity of the specular component by 96%. Curve 3610 plots the attenuated results, while curve 3612 plots the unattenuated results. FIG. 37 shows an enhanced contrast of the image of 20 nm defect by attenuating the intensity of the specular component by 99.9%. Curve 3710 plots the attenuated results, while curve 3712 plots the unattenuated results. Note that the amounts of attenuation used in the simulations are excessive. They are neither recommended nor practical in many cases. The reason for using excessive attenuations is to demonstrate the capability of the technique for contrast enhancement. As expected, smaller defects or wafer patterns require stronger attenuation of the specular component to achieve the same image contrast. The size of the defects and circuit patterns on the wafer will be decreased relentlessly and achieving high dynamic range in image sensors can be either difficult or costly in the future. Therefore, a strong attenuation of the specular component may be needed in the future. This is why in many embodiments an attenuator is in the path of the specular component. One of the drawbacks of this kind of contrast enhancement technique is the large loss of light energy. In order to compensate for the energy loss due to the attenuation of the specular component, more light can be produced in the illumination path or light can be collected for a longer period of time in collection path. In many applications, neither of these options is desirable because a strong illumination light can damage samples and a longer light collection will reduce throughput. Therefore, the contrast enhancement must be used with care with these and other undesirable side effects in mind. (Flood illumination on the sample as described herein can reduce the possibility of sample damage by intense illumination light.) Fortunately, even though the specular component was attenuated severely in the simulations to show the contrast enhancement clearly, most actual cases do not require that much contrast enhancement currently thanks to a large dynamic range of image sensors used in actual defect detection systems currently. Moderate contrast enhancement is not only very acceptable but also preferred considering the signal amplification, efficiency of light energy use or system throughput.

Selection of Polarization. As mentioned previously, in most cases, the signal-to-noise ratio of the defect signal depends on the polarizations of the illumination light and the collected light. Therefore, it is important to select correct polarizations for the defects of interest. The selection of correct polarizations can be done with either intuition, theoretical modeling, or numerical simulations. However, it is usually impractical to consider or test all different polarizations because of large numbers of different polarization states. As long as the defect and its neighboring patterns do not have helical structures, limiting the polarization choices to linear polarizations will be very acceptable.

2. Catch-all Mode. Defects can alter not only the amplitude but also the phase of scattered light. Different kinds of defects affect either the amplitude or the phase of signal light differently. Therefore, if both the amplitude and phase of signal light are measured, not only can more defects be caught but also more information about the defects can be obtained. The catch-all mode is based on the determination of both the amplitude and the phase of the defect signal. Because the defect signal is completely determined by the amplitude and the phase, if noise is low enough, the catch-all mode can, in principle, catch all different kinds of defects in one run. Thus, the catch-all mode is a powerful mode. A single run of the catch-all mode requires multiple scans of the sample. However, its throughput is not expected to be hit much compared with other modes because it can catch all different kinds of defects with a single run and there is no need for sample loading/unloading between multiple scans.

Three Scan Method. Equation (3) shows that the interference term contains the amplitude and cosine of the relative phase of the defect signal. In order to determine the amplitude and relative phase of the defect signal completely, at least three scans of sample should be used. The phase of the specular component should be set differently for each scan. The absolute phase values of the specular component need not be known. Rather what is important is the difference in phase values between the different scans. This can be achieved by calibrating the phase controller. For example, the phase controller can be calibrated using a step-phase object. The image of the step-phase object shows the contrast reversal around the phase-step area as the phase of the specular component passes the 90° point. The image contrast hits the extrema at zero and at a 180° phase angle of the specular component. Using this phenomenon and mechanical property of the phase controller, we can accurately calibrate the phase controller. Because the initial phase value of the specular component is not important, we can start from any phase setting of the specular component. For example, if the phase value of specular component for the first scan of sample is $\phi_b$ and the phase changes are $\theta_1$ and $\theta_2$ for second and third scan. Then, the complex amplitudes of the specular component for the first, second and third scans are expressed as follows:

$$b_0 \equiv b = |b|\exp(i\phi_b) \quad (4)$$

$$b_1 \equiv |b|\exp(i(\phi_b+\theta_1)) \quad (5)$$

$$b_2 \equiv |b|\exp(i(\phi_b+\theta_2)) \quad (6)$$

Then, the image intensities for the three sample scans are expressed as follows:

$$I_0 \equiv |b_0 + a + s|^2 + |q_a + q_s|^2 + |g|^2 \quad (7)$$
$$= |b|^2 + |a+s|^2 + |q_a+q_s|^2 + |g|^2 + 2|b||a+s|\cos(\varphi_{a+s})$$
$$= |b|^2 + |a+s|^2 + |q_a+q_s|^2 + |g|^2 + 2|b|(a_x+s_x)$$

-continued $$I_1 \equiv |b_1 + a + s|^2 + |q_a + q_s|^2 + |g|^2 \quad (8)$$
$$= |b|^2 + |a+s|^2 + |q_a+q_s|^2 + |g|^2 + 2|b||a+s|\cos(\varphi_{a+s} - \theta_1)$$
$$= |b|^2 + |a+s|^2 + |q_a+q_s|^2 + |g|^2 +$$
$$\quad 2|b||a+s|(\cos(\varphi_{a+s})\cos(\theta_1) + \sin(\varphi_{a+s})\sin(\theta_1))$$
$$= |b|^2 + |a+s|^2 + |q_a+q_s|^2 + |g|^2 +$$
$$\quad 2|b|((a_x+s_x)\cos(\theta_1) + (a_y+s_y)\sin(\theta_1))$$

$$I_2 \equiv |b_2 + a + s|^2 + |q_a + q_s|^2 + |g|^2 \quad (9)$$
$$= |b|^2 + |a+s|^2 + |q_a+q_s|^2 + |g|^2 + 2|b||a+s|\cos(\varphi_{a+s} - \theta_2)$$
$$= |b|^2 + |a+s|^2 + |q_a+q_s|^2 + |g|^2 +$$
$$\quad 2|b||a+s|(\cos(\varphi_{a+s})\cos(\theta_2) + \sin(\varphi_{a+s})\sin(\theta_2))$$
$$= |b|^2 + |a+s|^2 + |q_a+q_s|^2 + |g|^2 +$$
$$\quad 2|b|((a_x+s_x)\cos(\theta_2) + (a_y+s_y)\sin(\theta_2))$$

Then, the die-to-die (or cell-to-cell) subtracted intensities are:

$$\Delta I_0 \equiv I_0 - I_0(s=q_s=0) \quad (10)$$
$$= |a+s|^2 - |a|^2 + |q_a+q_s|^2 - |q_a|^2 + 2|b|s_x$$

$$\Delta I_1 \equiv I_1 - I_1(s=q_s=0) \quad (11)$$
$$= |a+s|^2 - |a|^2 + |q_a+q_s|^2 - |q_a|^2 +$$
$$\quad 2|b|(s_x\cos(\theta_1) + s_y\sin(\theta_1))$$

$$\Delta I_2 \equiv I_2 - I_2(s=q_s=0) \quad (12)$$
$$= |a+s|^2 - |a|^2 + |q_a+q_s|^2 - |q_a|^2 +$$
$$\quad 2|b|(s_x\cos(\theta_2) + s_y\sin(\theta_2))$$

These die-to-die subtracted intensities contain the needed amplitude and phase information of the defect signal. Therefore, these die-to-die subtracted intensities need to be stored for the whole wafer. This seems to require an unrealistic amount of memory space. But, in reality, it does not require too much memory space because the data are non-zero only in areas around defects which are extremely sparse in reality.

If $\theta_1$ and $\theta_2$ are not zero and $\theta_1 \neq \theta_2$, then, we can determine the complex amplitude (or equivalently the amplitude and phase) of the defect signal from equations (10), (11) and (12). The real and imaginary parts of the complex amplitude of the amplified defect signal are:

$$2|b|s_x = \frac{\Delta I_1 \sin(\theta_2) - \Delta I_2 \sin(\theta_1) - \Delta I_0 (\sin(\theta_2) - \sin(\theta_1))}{\sin(\theta_2 - \theta_1) - (\sin(\theta_2) - \sin(\theta_1))} \quad (13)$$

$$2|b|s_y = \frac{1}{\sin(\theta_2 - \theta_1)} \left\{ \begin{array}{l} -\left[\cos(\theta_2) + \dfrac{\sin(\theta_2)(\cos(\theta_2) - \cos(\theta_1))}{\sin(\theta_2 - \theta_1) - (\sin(\theta_2) - \sin(\theta_1))}\right]\Delta I_1 + \\ \left[\cos(\theta_1) + \dfrac{\sin(\theta_1)(\cos(\theta_2) - \cos(\theta_1))}{\sin(\theta_2 - \theta_1) - (\sin(\theta_2) - \sin(\theta_1))}\right]\Delta I_2 + \\ \left[1 + \dfrac{(\cos(\theta_2) - \cos(\theta_1))(\sin(\theta_2) - \sin(\theta_1))}{\sin(\theta_2 - \theta_1) - (\sin(\theta_2) - \sin(\theta_1))}\right]\Delta I_0 \end{array} \right\} \quad (14)$$

If $\theta_1=-\theta_2=\theta\neq 0$, then, equations (13) and (14) reduce to the following equations:

$$2|b|s_x = \frac{(2\Delta I_0 - \Delta I_1 - \Delta I_2)\sin(\theta)}{2\sin(\theta) - \sin(2\theta)} \quad (15)$$

$$2|b|s_y = \frac{(\Delta I_1 - \Delta I_2)\cos\theta}{\sin(2\theta)} \quad (16)$$

There are several good choices for $\theta_1$ and $\theta_2$ values. But, the best choice will be $$\theta_1 = -\theta_2 = \frac{2\pi}{3}$$

because of the resulting simplicity of signal intensity equation as shown by equation (19). (Other choices like $$\theta_1 = -\theta_2 = \frac{\pi}{3} \text{ or } \theta_1 = \frac{\pi}{3}, \theta_2 = \frac{2\pi}{3}$$

will work as well, but the expression of signal intensity will not be as simple and symmetric as equation (19).) If $$\theta_1 = -\theta_2 = \frac{2\pi}{3},$$

then, equations (15) and (16) further reduce to the following equations:

$$2|b|s_x = \frac{2\Delta I_0 - \Delta I_1 - \Delta I_2}{3} \quad (17)$$

$$2|b|s_y = \frac{\Delta I_1 - \Delta I_2}{\sqrt{3}} \quad (18)$$

The amplified defect signal intensity, $I_s$, for this case has the following simple expression:

$$I_s \equiv (2|b|s_x)^2 + (2|b|s_y)^2 \quad (19)$$
$$= \frac{4}{9}(\Delta I_0^2 + \Delta I_1^2 + \Delta I_2^2 - \Delta I_0\Delta I_1 - \Delta I_1\Delta I_2 - \Delta I_2\Delta I_0)$$
$$= \frac{2}{9}[(\Delta I_0 - \Delta I_1)^2 + (\Delta I_1 - \Delta I_2)^2 + (\Delta I_2 - \Delta I_0)^2]$$

$I_s$ is a raw signal intensity. Its magnitude depends not only on the intensity of illumination light but also on the intensity of specular component. Therefore, in order to make the defect signal more consistent, $I_s$ needs to be normalized against the intensities of illumination light and specular component. The illumination can be made pretty uniform across the field but the intensity of specular component can vary significantly over the whole field. An exact measurement of the intensity variation of the specular component is difficult to be done. Fortunately, exact values of the local intensity of the specular component are not needed. Approximate values are fine for normalization purpose. Local intensity values of the specular component can be approximated by the local average of the total light intensity in most cases. Therefore, the raw amplified defect signal intensity, $I_s$ can be properly normalized as follows.

$$I_s' \approx \frac{2}{9}\frac{[(\Delta I_0 - \Delta I_1)^2 + (\Delta I_1 - \Delta I_2)^2 + (\Delta I_2 - \Delta I_0)^2]}{I_{ill} \cdot I_{local}} \quad (20)$$

where $I_{ill}$=The intensity of illumination at sample plane.
$I_{local}$=The local average of total light intensity at image plane $I_s'$ is the normalized intensity of the amplified defect signal. Defects are usually detected by comparing the peak value of $I_s'$ with a preset value called threshold. More elaborate defect detection algorithms can also be used. The phase of the defect signal relative to the specular component, $\phi_s$, becomes $$\varphi_s = \tan^{-1}\left(\frac{s_y}{s_x}\right) = \tan^{-1}\left(\frac{\sqrt{3}(\Delta I_1 - \Delta I_2)}{2\Delta I_0 - \Delta I_1 - \Delta I_2}\right) \quad (21)$$

Figure 38:
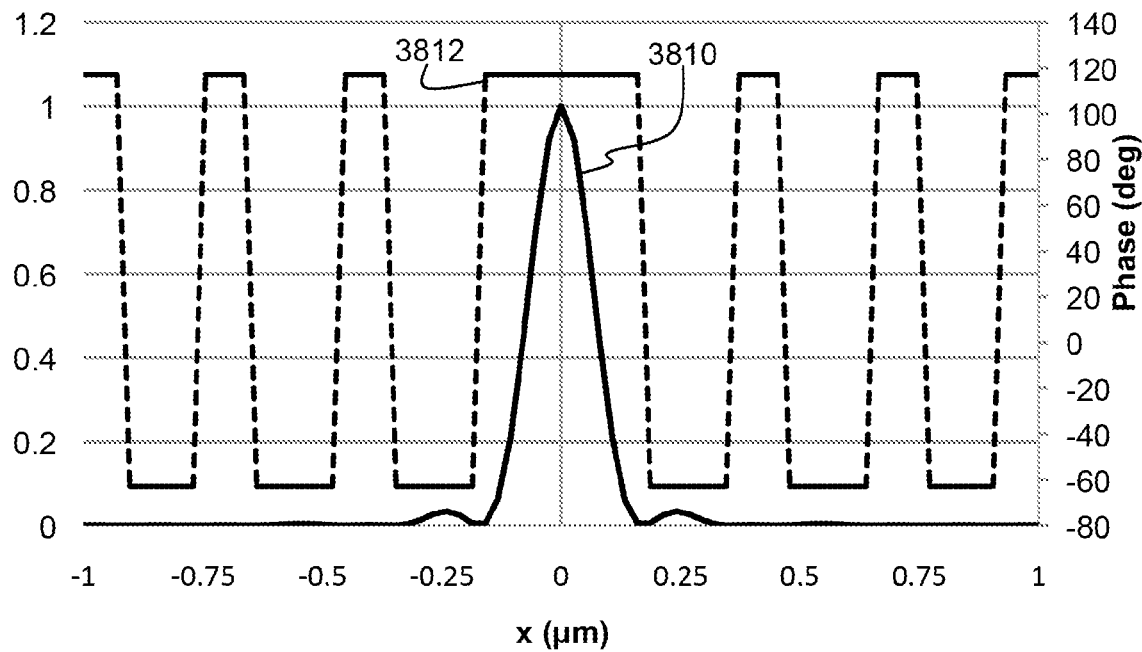
FIG. 38 shows plots of simulated signal intensity and the phase of 20 nm defect as an example.

FIG. 38 shows plots of the signal intensity and the phase of 20 nm defect as an example. Curve 3810 is the signal intensity and curve 3812 is the phase. For the detection of defect, only the peak value of signal intensity is usually needed.

Equations (17), (18), (19) and (20) can be especially useful in real systems because it does not take much computing time to calculate them and also they are the least sensitive to random noises thanks to an equal division of the phase angle range of the specular component by $\theta_1$ and $\theta_2$. By choosing $$\theta_1 = -\theta_2 = \frac{2\pi}{3}$$

and using those equations, the three scan method can determine the complex amplitude of the defect signal completely in a very effective manner.

Figure 39:
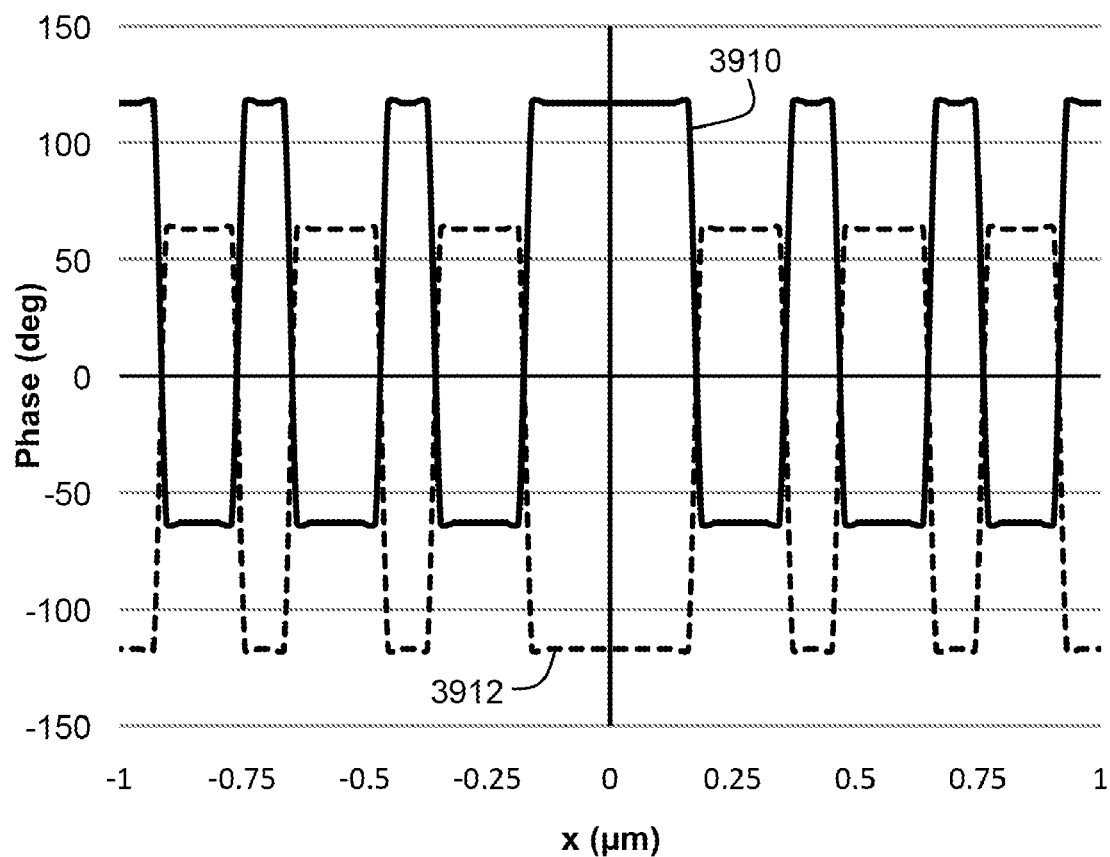
FIG. 39 shows plots of simulated phases of defect signals from 20 nm particle and 20 nm void.

The amplified defect signal intensity, equation (19) or (20), is the intensity of the whole, not just the real part, of the defect signal and, therefore, the true indicator of the existence of the defect. By comparing it with a predefined threshold, we can tell if a defect exists or not. If a defect exists, we can characterize it by calculating the complex amplitude of its signal using equations (17) and (18). This gives some crucial information about what kind of defect it is. For example, FIG. 39 shows plots of phases of defect signals from 20 nm particle and 20 nm void. Curve 3910 plots phases of the 20 nm void, and curve 3912 plots the phase of the 20 nm particle. From FIG. 39, it can be seen that the particle and voids give phase angles of opposite signs to the complex amplitudes of the defect signal. Therefore, even if the amplitudes of the defect signals are the same, we can tell which ones are particle type defects and which ones are void type defects. If the defect size is comparable or larger than the resolution of collection optics and noise is also low, we can even deconvolve the complex amplitude of the defect signal with the complex amplitude of the point spread function of imaging optics to get a more detailed picture of the defect. These kinds of capabilities will help defect classification immensely. Another important fact is that the strength of the amplified defect signal intensity, equation (19) or (20), does not depend on its orientation (or phase) in its complex plane. This means that the catch-all mode can potentially catch any kind of defects surrounded by any kind of patterns. This is why the catch-all mode is such a powerful mode. Conventional technologies cannot support the catch-all mode because they cannot measure both the real and imaginary parts of the complex amplitude of the defect signal. They can only measure the real part. In this case, the signal intensity critically depends on the orientation of the complex amplitude of the defect signal in its complex plane representation. Consequently, conventional technologies cannot find all the different kinds of defects. Rather, conventional technologies are likely to miss a significant number defects.

Two Scan Method. As stated previously, in general, it takes at least three sample scans in order to determine the complex amplitude of the defect signal completely. However, if the dark field part of the whole signal is negligible compared with the interference part, then two sample scans suffice to determine the complex amplitude of the defect signal. This can be seen easily from equations (10) and (11). If we ignore the dark field part in the equations and set $$\theta_l = \pm \frac{\pi}{2},$$

then, those equations give $$2|b|s_x \approx \Delta I_0 \quad (22)$$

$$2|b|s_y \approx \pm \Delta I_1 \quad (23)$$

The amplified defect signal intensity, $I_s$, becomes $$I_s \equiv (2|b|s_x)^2 + (2|b|s_y)^2 \approx \Delta I_0^2 + \Delta I_1^2 \quad (24)$$

The normalized amplified defect signal intensity, $I_s'$ becomes $$I_s' \approx \frac{\Delta I_0^2 + \Delta I_1^2}{I_{ill} \cdot I_{local}} \quad (25)$$

If the image sensor has a large dynamic range, then we can boost the interference part of the whole signal by a large amount. In this case, the dark field part of the whole signal can be so small that we may be able to use the two scan method to speed up the catch-all mode of the operation.

Four Scan Method. A simple choice for the four phase values of specular component is $0, \pi,$ $$\frac{\pi}{2} \text{ and } -\frac{\pi}{2}.$$

If we scan the sample four times with $0, \pi,$ $$\frac{\pi}{2} \text{ and } -\frac{\pi}{2}$$

phase change of the specular component per scan, then, $$b_0 \equiv b = |b|\exp(i\varphi_b) \quad (26)$$

$$b_1 \equiv |b|\exp(i(\varphi_b + \pi)) \quad (27)$$

$$b_2 \equiv |b|\exp\left(i\left(\varphi_b + \frac{\pi}{2}\right)\right) \quad (28)$$

$$b_3 \equiv |b|\exp\left(i\left(\varphi_b - \frac{\pi}{2}\right)\right) \quad (29)$$

Die-to-die subtracted intensities become $$\Delta I_0 \equiv I_0 - I_0(s = q_s = 0) = |a+s|^2 - |a|^2 + |q_a + q_a|^2 - |q_a|^2 + 2|b|s_x \quad (30)$$

$$\Delta I_1 \equiv I_1 - I_1(s = q_s = 0) = |a+s|^2 - |a|^2 + |q_a + q_a|^2 - |q_a|^2 - 2|b|s_x \quad (31)$$

$$\Delta I_2 \equiv I_2 - I_2(s = q_s = 0) = |a+s|^2 - |a|^2 + |q_a + q_a|^2 - |q_a|^2 + 2|b|s_y \quad (32)$$

$$\Delta I_3 \equiv I_3 - I_3(s = q_s = 0) = |a+s|^2 - |a|^2 + |q_a + q_a|^2 - |q_a|^2 - 2|b|s_y \quad (33)$$

The real and imaginary parts of the complex amplitude of the amplified defect signal become $$2|b|s_x = \frac{\Delta I_0 - \Delta I_1}{2} \quad (34)$$

$$2|b|s_y = \frac{\Delta I_2 - \Delta I_3}{2} \quad (35)$$

The amplified defect signal intensity, $I_s$, for this case has the following simple expression:

$$I_s \equiv (2|b|s_x)^2 + (2|b|s_y)^2 = \frac{1}{4}[(\Delta I_0 - \Delta I_1)^2 + (\Delta I_2 - \Delta I_3)^2] \quad (36)$$

The normalized amplified defect signal intensity becomes $$I_s' \approx \frac{1}{4}\frac{[(\Delta I_0 - \Delta I_1)^2 + (\Delta I_2 - \Delta I_3)^2]}{I_{ill} \cdot I_{local}} \quad (37)$$

The relative phase of the defect signal to the specular component, $\phi_s$, becomes $$\varphi_s = \tan^{-1}\left(\frac{s_y}{s_x}\right) = \tan^{-1}\left(\frac{\Delta I_2 - \Delta I_3}{\Delta I_0 - \Delta I_1}\right) \quad (38)$$

This four scan method provides simpler equations. However, its main drawback is that the relative phase angle between defect signal and specular component can be as large as 45°. (The maximum relative phase angle for three scan method is 30°.) This fact can make this four scan method less sensitive to some defects than three scan method. In order to achieve better sensitivity than three scan method, different phase values than $$\left\{0, \pi, \frac{\pi}{2} \text{ and } -\frac{\pi}{2}\right\}$$

must be chosen. Possible different choices are $$\left\{0, \frac{\pi}{4}, \frac{\pi}{2} \text{ and } \frac{3\pi}{4}\right\}, \left\{\pm\frac{\pi}{8}, \pm\frac{3\pi}{8}\right\},$$

etc. However, these other choices require the use of a regression method to determine the defect signal and make the analytical expression of defect signal more complicated. (See next subsection for a general expression of defect signal.) Other obvious drawback of four scan methods is reduced throughput compared with three scan methods thanks to one more sample scan needed.

Higher Scan Methods. A more independent image data means a better signal-to-noise ratio. Therefore, if we want to increase the signal-to-noise ratio, we can scan samples more than four times with a different phase setting of the specular component per scan. In this case, the amount of data is more than needed to determine uniquely the complex amplitude of the defect signal. Therefore, a regression method should be adopted to determine the defect signal. There are many different regression methods available with known pros and cons. One of the most popular regression methods is the least-square regression. It is the best choice if noises are random. It also allows analytical approach for the current case. Analytical regression is important because it can save a lot of computation time. Other regression methods can be more suitable if noises are not random but they usually do not allow analytical approaches. Therefore, only the least-square regression is presented here.

Let's assume that sample is scanned N times with different phase setting for each scan, then, the die-to-die subtracted image intensity for nth scan is expressed as follows.

$$\Delta I_n^{(0)} = D + 2|b|(s_x \cos(\theta_n) + s_y \sin(\theta_n)) \tag{39}$$

where $D \equiv |a+s|^2 - |a|^2 + |q_a+q_a|^2 - |q_a|^2$: dark field term (40)

The error function is defined as follows in least-square regression.

$$E = \sum_{n=0}^{N-1} (\Delta I_n - \Delta I_n^{(0)})^2 \tag{41}$$

where $\Delta I_n$=Measured die-to-die subtracted image intensity

We have to find D, $s_x$ and $s_y$ values that minimize the error function. The slopes of error function become zero at its minimum. Therefore, the solution satisfies following three equations.

$$\frac{-1}{2}\frac{\partial E}{\partial D} = \sum_{n=0}^{N-1}(\Delta I_n - \Delta I_n^{(0)}) = \tag{42}$$

$$0 = \sum_{n=0}^{N-1}\Delta I_n - \sum_{n=0}^{N-1}[D + 2|b|(s_x\cos(\theta_n) + s_y\sin(\theta_n))] =$$

$$\sum_{n=0}^{N-1}\Delta I_n - ND - 2|b|\sum_{n=0}^{N-1}(s_x\cos(\theta_n) + s_y\sin(\theta_n))$$

-continued $$\frac{-1}{4|b|}\frac{\partial E}{\partial s_x} = \tag{43}$$

$$\sum_{n=0}^{N-1}\cos(\theta_n)(\Delta I_n - \Delta I_n^{(0)}) = 0 = \sum_{n=0}^{N-1}\Delta I_n\cos(\theta_n) - \sum_{n=0}^{N-1}[D\cos(\theta_n) +$$

$$2|b|(s_x\cos^2(\theta_n) + s_y\sin(\theta_n)\cos(\theta_n))] = \sum_{n=0}^{N-1}\Delta I_n\cos(\theta_n) -$$

$$D\sum_{n=0}^{N-1}\cos(\theta_n) - |b|s_x\left[N + \sum_{n=0}^{N-1}\cos(2\theta_n)\right] - |b|s_y\sum_{n=0}^{N-1}\sin(2\theta_n)$$

$$\frac{-1}{4|b|}\frac{\partial E}{\partial s_y} = \tag{44}$$

$$\sum_{n=0}^{N-1}\sin(\theta_n)(\Delta I_n - \Delta I_n^{(0)}) = 0 = \sum_{n=0}^{N-1}\Delta I_n\sin(\theta_n) - \sum_{n=0}^{N-1}[D\sin(\theta_n) +$$

$$2|b|(s_x\sin(\theta_n)\cos(\theta_n) + s_y\sin^2(\theta_n))] = \sum_{n=0}^{N-1}\Delta I_n\sin(\theta_n) -$$

$$D\sum_{n=0}^{N-1}\sin(\theta_n) - |b|s_x\sum_{n=0}^{N-1}\sin(2\theta_n) - |b|s_y\left[N - \sum_{n=0}^{N-1}\cos(2\theta_n)\right]$$

Then, from equation (42), $$D = \frac{1}{N}\sum_{n=0}^{N-1}\Delta I_n - \frac{2|b|}{N}\sum_{n=0}^{N-1}(s_x\cos(\theta_n) + s_y\sin(\theta_n)) \tag{45}$$

By substituting equation (45) into equations (43) and (44), $$\frac{-1}{4|b|}\frac{\partial E}{\partial s_x} = A - B|b|s_x - C|b|s_y = 0 \tag{46}$$

$$\frac{-1}{4|b|}\frac{\partial E}{\partial s_y} = A' - C|b|s_x - B'|b|s_y = 0 \tag{47}$$

$$\text{where } A \equiv \sum_{n=0}^{N-1}\Delta I_n\cos(\theta_n) - \frac{1}{N}\left(\sum_{n=0}^{N-1}\Delta I_n\right)\left(\sum_{n=0}^{N-1}\cos(\theta_n)\right) \tag{48}$$

$$B \equiv N + \sum_{n=0}^{N-1}\cos(2\theta_n) - \frac{2}{N}\left(\sum_{n=0}^{N-1}\cos(\theta_n)\right)^2 \tag{49}$$

$$C \equiv \sum_{n=0}^{N-1}\sin(2\theta_n) - \frac{2}{N}\left(\sum_{n=0}^{N-1}\cos(\theta_n)\right)\left(\sum_{n=0}^{N-1}\sin(\theta_n)\right) \tag{50}$$

$$A' \equiv \sum_{n=0}^{N-1}\Delta I_n\sin(\theta_n) - \frac{1}{N}\left(\sum_{n=0}^{N-1}\Delta I_n\right)\left(\sum_{n=0}^{N-1}\sin(\theta_n)\right) \tag{51}$$

$$B' \equiv N - \sum_{n=0}^{N-1}\cos(2\theta_n) - \frac{2}{N}\left(\sum_{n=0}^{N-1}\sin(\theta_n)\right)^2 \tag{52}$$

From equations (46) and (47), $$|b|s_x = \frac{AB' - A'C}{BB' - C^2} \tag{53}$$

$$|b|s_y = \frac{A'B - AC}{BB' - C^2} \tag{54}$$

Equations (53) and (54) are the general best solutions for the complex amplitude of amplified defect signal. By substituting equations (53) and (54) into equation (45), $$D = \frac{1}{N}\sum_{n=0}^{N-1}\Delta I_n - \frac{2}{N}\left[\left(\frac{AB' - A'C}{BB' - C^2}\right)\left(\sum_{n=0}^{N-1}\cos(\theta_n)\right) + \left(\frac{A'B - AC}{BB' - C^2}\right)\left(\sum_{n=0}^{N-1}\sin(\theta_n)\right)\right] \quad (55)$$

The signal intensity can be computed quickly using its defining equation (36) and be used for defect detection in the manner described previously.

Generally, if $N \geq 4$, we can also estimate the integrity of measurement data by computing the amount of residual error after the regression. The residual error can be computed quickly by substituting equations (53), (54) and (55) into equation (41) and summing up each terms in the equation. By comparing the residual error with a preset value, we can tell the soundness of measurements. The checking of residual error is especially helpful in system trouble shootings. It is usually the first step in system trouble shooting process.

Equations (53) and (54) reduce to equations (13) and (14) respectively when N=3.

If the phase settings are chosen to meet following condition, $$\sum_{n=0}^{N-1}\cos(\theta_n) = \sum_{n=0}^{N-1}\sin(\theta_n) = \sum_{n=0}^{N-1}\cos(2\theta_n) = \sum_{n=0}^{N-1}\sin(2\theta_n) = 0 \quad (56)$$

(As an example, the above condition can be met if all the $\theta_n$ are chosen with even angular intervals.)
then, $$A = \sum_{n=0}^{N-1}\Delta I_n \cos(\theta_n), \, A' = \sum_{n=0}^{N-1}\Delta I_n \sin(\theta_n), \, B = B' = N, \, C = 0 \quad (57)$$

and, consequently, in this case, $$|b|s_x = \frac{A}{N} = \frac{1}{N}\sum_{n=0}^{N-1}\Delta I_n \cos(\theta_n) \quad (58)$$

$$|b|s_y = \frac{A'}{N} = \frac{1}{N}\sum_{n=0}^{N-1}\Delta I_n \sin(\theta_n) \quad (59)$$

$$D = \frac{1}{N}\sum_{n=0}^{N-1}\Delta I_n \quad (60)$$

It is easy to see that equations (58) and (59) reduce to equations (17) and (18) respectively when N=3 and $\theta_0=0$, $$\theta_1 = -\theta_2 = \frac{2\pi}{3}.$$

They also reduce to equations (34) and (35) when N=4 and $\theta_0=0$, $\theta_1=\pi$, $$\theta_2 = -\theta_3 = \frac{\pi}{2}.$$

As shown above, the regression process for catch-all mode can be done analytically. Therefore, the operation in catch-all mode does not require excessive computing time even if sample is scanned a lot more than three times in order to obtain more reliable defect signals. Definitely, more scans mean lower throughput. However, if the signal-to-noise ratio is low, more sample scans can help significantly.

Contrast Enhancement. If the dynamic range of image sensor is limited, the contrast of the image needs to be increased in the catch-all mode for the same reason described in the section of the high sensitivity mode. The same contrast enhancement technique described in the section of high sensitivity mode can be used.

Polarization Diversity. As mentioned previously, the strength of the defect signal can depend on the polarizations of the illumination light and also collected light. Therefore, if defects of interest are composed of different kinds of defects, whose signal strengths depend on polarizations differently, then in order to capture all different kinds of defects, sample images need to be collected with multiple different polarizations. This is called polarization diversity. Polarization diversity inevitably increases the number of sample scans and consequently reduces throughput. Therefore, in practice, polarization diversity should be minimized and balanced with its undesirable impact to throughput. Sometimes, a basic understanding of optical physics helps in reducing polarization diversity. For example, as long as the defect and its neighboring patterns do not have helical structures, limiting polarization diversity to linear polarizations will be very acceptable.

Spatial Bandwidth. Maximum spatial frequency of the complex amplitude distribution of the optical signal collected by the collection lens is $$\frac{\lambda}{NA}$$

where NA is the numerical aperture of the collection lens. However, the maximum spatial frequency for the intensity distribution is $$\frac{2\lambda}{NA}$$

because the intensity is the absolute square of the complex amplitude. But, if we take a look at equation (1) in more detail, we find that in actuality, only the dark field terms have a maximum spatial frequency of $$\frac{2\lambda}{NA}.$$

A maximum spatial frequency of interference term is only $$\frac{\lambda}{NA}.$$

Figure 40:
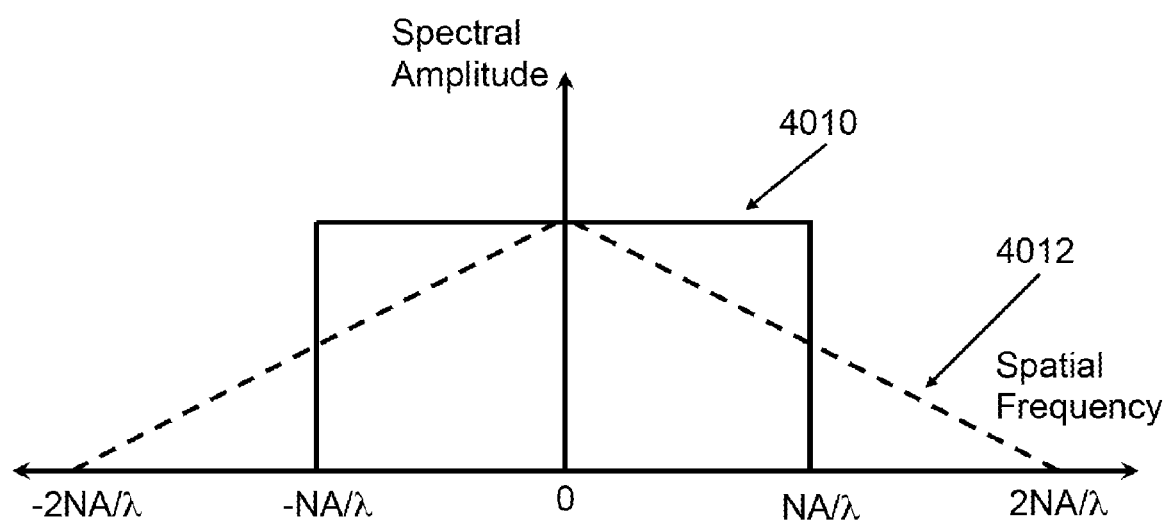
FIG. 40 shows plots of spatial frequency bandwidths of defect signal components.

This is because the maximum spatial frequency of the specular component is virtually zero. This fact is depicted in FIG. 40, which plots spatial frequency bandwidths of defect signal components. Curve 4010 plots the interference term and curve 4012 plots the dark field terms. Maximum spatial frequency for high sensitivity mode and dark field mode is $$\frac{2\lambda}{NA}$$

because they have dark field terms in their image measurements and utilize them. However, the catch-all mode drops out all dark field terms during the signal processing and utilizes only interference terms. Therefore, the maximum spatial frequency for the catch-all mode is $$\frac{\lambda}{NA}, \text{not } \frac{2\lambda}{NA}.$$

This has a significant implication. Nyquist sampling theorem states that the spatial frequency of the image sampling should be at least two times the maximum spatial frequency of the image in order to pick up all information in the image and to avoid signal aliasings. This means that if we use the same image sensor for all modes, the image magnification of the catch-all mode does not need to be as high as that of the high sensitivity mode or dark field mode to pick tip all needed information about the defect and to prevent signal aliasing. This means that the same image sensor can cover a larger field of view at the sample plane in the catch-all mode. A larger field of view means a higher throughput. Thus, the throughput reduction of the catch-all mode due to multiple sample scans can be significantly compensated by the increase of the field of view.

Note that the Nyquist theorem assumes delta function as the sampling function. But, any real sampling function cannot be delta function. Therefore, Nyquist theorem cannot be applied to real systems without modification. However, the general arguments presented here still hold.

3. Dark Field Mode. The dark field mode is realized by completely blocking out the specular component. The additional two-dimensional Fourier filtering of noise-generating light will make the dark field mode very quiet (or of very low noise). It will have much less photon noise than the existing dark field modes with line illumination which allow only one dimensional Fourier filtering. However, as explained previously, even with two-dimensional Fourier filtering, the dark field mode is not a good choice for the detection of tiny defects whose sizes are smaller than $$\frac{\lambda}{4}.$$

However, the dark field mode is a good choice for the detection of large defects because it produces strong enough signals for a variety of different kinds of large defects and a single scan of sample is usually enough. Another good use of the dark field mode is finding the best focus for the image sensor. This is because the dark field mode block out the specular component which does not carry any focus information but still can affect the image critically during image focusing through its interference with scattered component.

IV. Applications

As already mentioned, the originally intended application of the techniques described herein is finding defects in wafers and reticles. However, the application of these techniques is not so limited. Any high-resolution optical inspection or measurement that can be benefited from the determination of both the amplitude and phase of the optical signal can be a good application. The following is a partial list of possible applications: defect detection of patterned wafers; defect detection of bare wafers; crystal defect detection of bare wafers; defect review; defect detection of reticles; complex amplitude measurement of reticle transmission or reflection; complex amplitude measurement of optical proximity correctors in OPC reticles; complex amplitude measurement of phase masks; high resolution measurement of surface topology; inspection of nano structures; overlay error measurement of circuit patterns; phase-contrast imaging; and high contrast imaging.

Many of advantages of the various embodiments have been described herein. Such advantages include: high defect signal; high defect detection sensitivity; less false defect detections; ability to catch different kinds of defects at a time; ability to distinguish between voids and particles or mesa and valley; increased consistent performance; increased uniform image intensity across the field leading to effective utilization of image sensor dynamic range for the amplification of defect signal; mode-locked laser rather than CW laser can be used thereby lowering cost; no speckle busting leading to lower cost; ability to use flood illumination thereby decreasing the chance of wafer damage; ability to use coherent illumination leading to well-defined diffraction orders, thereby providing for straightforward Fourier filtering; simple system configuration leading to lower cost; no pupil or aperture stop relay needed leading to lower cost and decreasing energy loss; and efficient energy use.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the inventive body of work is not to be limited to the details given herein, which may be modified within the scope and equivalents of the appended claims.

What is claimed is:

1. A common-path interferometry system for the detection of defects in a sample, the system comprising:
    an illumination source for generating electromagnetic energy directed toward the sample;
    an optical imaging system for collecting a portion of the electromagnetic energy from the sample including a scattered component of the electromagnetic energy that is predominantly scattered by the sample, and a specular component of the electromagnetic energy that is predominantly undiffracted by the sample;

a variable phase controlling system for adjusting a relative phase of the scattered component and the specular component so as to improve the ability to detect defects in the sample; and a sensing system for sensing at least portions of the scattered component and specular component.

2. A system according to claim 1 wherein the sample is a wafer.

3. A system according to claim 1 wherein the sample is a reticle.

4. A system according to claim 1 wherein the scattered and specular components are reflected from a surface of the sample.

5. A system according to claim 1 wherein the variable phase controlling system is positioned such that the relative phase is adjusted at or near an aperture stop of the optical imaging system.

6. A system according to claim 1 wherein the variable phase controlling system is positioned such that the relative phase is adjusted at or near a conjugate plane of an aperture stop of the optical imaging system.

7. A system according to claim 1 wherein defect detection is facilitated by comparing the sensed portions of scattered and specular components with reference information.

8. A system according to claim 6 wherein the sample includes a die of circuit patterns on a semiconductor wafer, and the reference information includes sensed portions of scattered and specular components of a neighboring die of circuit patterns on the wafer.

9. A system according to claim 6 wherein the sample includes a memory area and sensed portions of scattered and specular components from one memory cell are compared with that of another memory cell.

10. A system according to claim 7 wherein the sample is a reticle and the reference information includes at least a portion of a computer generated defect-free reticle image.

11. A system according to claim 1 wherein the relative phase is primarily adjusted by adjusting a phase of the specular component relative to a phase of the scattered component.

12. A system according to claim 11 wherein the phase of the specular component is adjusted primarily using a moveable wedge shaped member positioned in a path of the specular component.

13. A system according to claim 11 wherein the phase of the specular component is adjusted primarily using a moveable mirror positioned in a path of the specular component.

14. A system according to claim 1 further comprising an attenuation system for adjustably attenuating the specular component.

15. A system according to claim 14 wherein the attenuation system adjustably attenuates the specular component using a member having a step-varied reflective coating.

16. A system according to claim 14 wherein the attenuation system uses polarization optical components to provide continuously-variable attenuation of the specular component.

17. A system according to claim 14 wherein an amplitude of specular component is attenuated to increase image contrast.

18. A system according to claim 14 wherein the attenuation system is primarily non-absorbing.

19. A system according to claim 14 wherein an amplitude of the scattered component is attenuated to increase image contrast.

20. A system according to claim 1 wherein the specular component is used to amplify electromagnetic energy scattered by defects in the sample.

21. A system according to claim 20 wherein the amplification does not substantially degrade a signal to noise ratio for the electromagnetic energy scattered by defects in the sample.

22. A system according to claim 1 further comprising polarization optical components selected and arranged such that polarization of the specular and/or scattered components can be varied.

23. A system according to claim 22 wherein the polarization of specular component can be set to maximize a signal-to-noise ratio of electromagnetic energy scattered by defects in the sample.

24. A system according to claim 1 wherein the electromagnetic energy directed toward the sample is at a substantially low angle of incidence.

25. A system according to claim 1 wherein the electromagnetic energy directed toward the sample is at a substantially high angle of incidence so as to reduce pattern noise from the sample.

26. A system according to claim 25 wherein the electromagnetic energy directed toward the sample is such that a reduced amount of flare occurs.

27. A system according to claim 1 wherein the electromagnetic energy can be directed toward the sample from a plurality of different azimuthal angles of incidence.

28. A system according to claim 27 further comprising a rotating mirror or a rotating prism for providing the different azimuthal angles of incidence.

29. A system according to claim 1 wherein the sensing system senses both amplitude and phase information from the scattered and specular components.

30. A system according to claim 1 wherein the electromagnetic energy generated by the illumination source is substantially coherent and is predominantly of a first wavelength.

31. A system according to claim 30 wherein the illumination source includes a laser.

32. A system according to claim 30 wherein the sample is illuminated coherently by the electromagnetic energy.

33. A system according to claim 30 further comprising:

a second illumination source for generating substantially coherent electromagnetic energy of a second wavelength, wherein the sample is illuminated coherently by the electromagnetic energy of the first wavelength and the second wavelength; and a second sensing system for sensing at least portions of a scattered component and specular component of the electromagnetic energy from the sample of the second wavelength.

34. A system according to claim 33 further comprising a wavelength splitter for simultaneous multiple wavelength operation which transmits the first wavelength and reflects the second wavelength, and a compensation plate for each wavelength each of which compensates an optical path length for electromagnetic energy having the corresponding wavelength.

35. A system according to claim 30 further comprising a second illumination source for generating a electromagnetic energy predominantly of a second wavelength directed toward the sample, and a plurality of waveplate sections with at least one waveplate for the two different wavelengths of electromagnetic energy.

36. A system according to claim 35 wherein the waveplate sections are arranged as segments on one or more circular rotatable members.

37. A system according to claim 1 further comprising a Fourier filtering system for selectively blocking light at or near an aperture stop of the optical imaging system.

38. A system according to claim 1 further comprising a Fourier filtering system for selectively blocking light at or near a conjugate plane of an aperture stop of the optical imaging system.

39. A system according to claim 38 wherein light is blocked by the Fourier filtering system in two orthogonal directions corresponding to a type of noise-generating electromagnetic energy scattered from the sample.

40. A system according to claim 1 wherein a portion of the electromagnetic energy directed toward the sample transmits through the sample thereby generating the scattered and specular components.

41. A system according to claim 40 wherein the sample is a reticle.

42. A system according to claim 40 wherein a portion of the electromagnetic energy directed toward the sample is reflected from a surface of the sample thereby generating a second specular component and a second scattered component, and the system further comprising a second sensing system for sensing at least portions of the second scattered and second specular components.

43. A system according to claim 1 wherein the illumination source is an extended illumination source.

44. A system according to claim 1 wherein the relative phase of the scattered component and the specular component is adjusted such that an expected signal from defects on the sample is maximized.

45. A system according to claim 1 wherein the relative phase of the scattered component and the specular component is adjusted such that a signal to noise ratio of an expected signal from defects on the sample is maximized.

46. A system according to claim 1 wherein the relative phase of the specular and scattered components is adjusted such that a determination of both amplitude and phase of a signal from defects on the sample can be made.

47. A system according to claim 1 wherein the system is used for one or more applications selected from the group consisting of: detection of defects in densely-patterned, sparsely-patterned or bare semiconductor wafers, reticles, crystal or glass substrates, nano structures, or biological samples; defect review; high resolution measurement of surface topology; high-contrast imaging; phase-contrast imaging; and overlay error measurement.

48. A system according to claim 1 wherein the optical imaging system has a relatively high numerical aperture thereby providing high spatial resolution to the sensing system.

49. A system according to claim 1 wherein the optical imaging system includes a front-end optical imaging lens group for collecting the scattered component and the specular component from the sample.

50. A system according to claim 1 wherein the scattered component and the specular component interfere with each other at an image plane of the sensing system.

51. A system according to claim 1 wherein the optical imaging system includes an adjustable aperture for the specular component.

52. A system according to claim 1 further comprising an analysis system which is programmed to perform two-dimensional signal processing to detect defects.

53. A method of using common-path interferometry to detect defects in a sample, the method comprising:
directing electromagnetic energy toward the sample;
collecting with an optical imaging system from the sample
 a scattered component of the electromagnetic energy that is predominantly scattered by the sample, and a specular component of the electromagnetic energy that is predominantly undiffracted by the sample;
adjusting a relative phase of the scattered component and the specular component using a variable phase controlling system so as to improve the ability to detect defects in the sample; and
sensing at least portions of the scattered component and specular component after said phase adjustment.

54. A method according to claim 53 wherein the sample is a wafer.

55. A method according to claim 53 wherein the sample is a reticle.

56. A method according to claim 53 wherein the scattered and specular components are reflected from a surface of the sample.

57. A method according to claim 53 wherein said adjusting the relative phase occurs at or near an aperture stop of the optical imaging system.

58. A method according to claim 53 wherein said adjusting the relative phase occurs at or near a conjugate plane of the aperture stop of the optical imaging system.

59. A method according to claim 53 further comprising comparing the sensed portions of scattered and specular components with reference information.

60. A method according to claim 59 wherein the sample includes a die of circuit patterns on a semiconductor wafer, and the reference information includes sensed portions of scattered and specular components of a neighboring die of circuit patterns on the wafer.

61. A method according to claim 59 wherein the sample includes a memory area and sensed portions of scattered and specular components from one memory cell are compared with that of another memory cell.

62. A method according to claim 59 wherein the sample is a reticle and the reference information includes at least a portion of a computer generated defect-free reticle image.

63. A method according to claim 53 wherein the relative phase is primarily adjusted by adjusting a phase of the specular component relative to a phase of the scattered component.

64. A method according to claim 63 wherein the phase of the specular component is adjusted primarily using a moveable wedge shaped member positioned in a path of the specular component.

65. A method according to claim 63 wherein the phase of the specular component is adjusted primarily using a moveable mirror positioned in a path of the specular component.

66. A method according to claim 53 further comprising adjustably attenuating the specular component.

67. A method according to claim 66 wherein the specular component is adjustably attenuated using a member having step-varied reflective coating.

68. A method according to claim 66 wherein the specular component is adjustably attenuated using polarization optical components that allow for continuously-variable attenuation of the specular component.

69. A method according to claim 66 wherein an amplitude of the specular component is attenuated so as to increase image contrast.

70. A method according to claim 53 wherein the specular component is used to amplify electromagnetic energy scattered by defects in the sample.

71. A method according to claim 70 wherein the amplification does not substantially degrade a signal to noise ratio for the electromagnetic energy scattered by defects in the sample.

72. A method according to claim 53 further comprising changing polarization of at least one of the specular and scattered components.

73. A method according to claim 72 wherein a polarization of the specular component is changed so as to maximize a signal-to-noise ratio of electromagnetic energy scattered by defects in the sample.

74. A method according to claim 53 wherein the electromagnetic energy directed toward the sample is at a substantially low angle of incidence.

75. A method according to claim 53 wherein the electromagnetic energy directed toward the sample is at a substantially high angle of incidence so as to reduce pattern noise from the sample.

76. A method according to claim 75 wherein the electromagnetic energy is directed toward the sample so as to reduce an amount of flare.

77. A method according to claim 53 wherein the electromagnetic energy can be directed toward the sample from a plurality of different azimuthal angles of incidence.

78. A method according to claim 77 wherein a rotating mirror or a rotating prism is used to provide different azimuthal angles of incidence.

79. A method according to claim 53 wherein the sensing system senses amplitude and phase information from the scattered and specular components.

80. A method according to claim 53 wherein the electromagnetic energy is substantially coherent and is predominantly of a first wavelength.

81. A method according to claim 80 wherein the electromagnetic energy is generated using a laser.

82. A method according to claim 80 wherein the sample is illuminated coherently by the electromagnetic energy.

83. A method according to claim 80 further comprising:
directing electromagnetic energy of predominantly a second wavelength toward the sample, wherein the sample is illuminated coherently by the electromagnetic energy of the first wavelength and the second wavelength; and
sensing at least portions of a scattered component and specular component of the electromagnetic energy from the sample of the second wavelength.

84. A method according to claim 83 wherein said directing and sensing electromagnetic energy of predominantly the first wavelength and said directing and sensing the electromagnetic energy of predominantly the second wavelength occur during the same time.

85. A method according to claim 83 wherein said directing and sensing electromagnetic energy of predominantly the first wavelength and said directing and sensing the electromagnetic energy of predominantly the second wavelength occur sequentially.

86. A method according to claim 53 further comprising selectively blocking light at or near an aperture stop of the optical imaging system so as to provide Fourier filtering capability.

87. A method according to claim 86 wherein light is blocked in two orthogonal directions corresponding to a type of noise-generating electromagnetic energy scattered from the sample.

88. A method according to claim 53 further comprising selectively blocking light at or near a conjugate plane of an aperture stop of the optical imaging system so as to provide Fourier filtering capability.

89. A method according to claim 53 wherein a portion of the electromagnetic energy directed toward the sample transmits through the sample thereby generating the scattered and specular components.

90. A method according to claim 89 wherein the sample is a reticle.

91. A method according to claim 89 wherein a portion of the electromagnetic energy directed toward the sample is reflected from a surface of the sample thereby generating a second specular component and a second scattered component, and the method further comprising sensing at least portions of the second scattered and second specular components.

92. A method according to claim 53 wherein the electromagnetic energy is emitted from an extended illumination source.

93. A method according to claim 53 wherein the relative phase of the scattered component and the specular component is adjusted such that an expected signal from defects on the sample is maximized.

94. A method according to claim 53 wherein the relative phase of the scattered component and the specular component is adjusted such that a signal to noise ratios of an expected signal from defects on the sample is maximized.

95. A method according to claim 53 wherein the relative phase between specular and scattered components is adjusted such that the sign of a term representing interference between the scattered and specular components term is the same as that of a term representing a dark field.

96. A method according to claim 53 wherein the relative phase of the specular and scattered components is adjusted such that a determination of both amplitude and phase of a signal from defects on the sample can be made.

97. A method according to claim 53 wherein said sensing and said directing electromagnetic energy are repeated for different adjustments made to the relative phase of the scattered and specular components.

98. A method according to claim 97 further comprising determining a complex amplitude of a defect signal.

99. A method according to claim 97 further comprising attenuating the amplitude of the specular component so as to increase image contrast.

100. A method according to claim 97 further comprising changing a polarization of the specular component such that a complex amplitude of a defect signal can be determined.

101. A method according to claim 97 further comprising comparing the sensed portions of scattered and specular components with reference information; and storing data relating to the comparison.

102. A method according to claim 53 wherein the system is used for one or more applications selected from the group consisting of: detection of defects in densely-patterned, sparsely-patterned or bare semiconductor wafers, reticles, crystal or glass substrates, nano structures, or biological samples; defect review; high resolution measurement of surface topology; high-contrast imaging; phase-contrast imaging; and overlay error measurement.

103. A method according to claim 53 wherein the scattered component and the specular component interfere with each other at an image plane where said sensing takes place.

104. A method according to claim 53 further comprising adjusting an adjustable aperture for the specular component.

105. A common-path interferometry system comprising:
an illumination source for generating electromagnetic energy directed toward a sample;
an optical imaging system for collecting a portion of the electromagnetic energy from the sample including a scattered component of the electromagnetic energy that is predominantly scattered by the sample, and a specular component of the electromagnetic energy that is predominantly undiffracted by the sample;

a variable phase controlling system for adjusting a relative phase of the scattered component and the specular component so as to improve the ability to observe the sample; and a sensing system for sensing at least portions of the scattered component and specular component.

106. A system according to claim 105 wherein the variable phase controlling system is positioned such that the relative phase is adjusted at or near the aperture stop of the optical imaging system.

107. A system according to claim 105 further comprising comparing the sensed portions of scattered and specular components with reference information.

108. A system according to claim 105 wherein the relative phase is primarily adjusted by adjusting a phase of the specular component relative to a phase of the scattered component.

109. A system according to claim 105 further comprising an attenuation system for adjustably attenuating the specular component.

110. A system according to claim 105 wherein the specular component is used to amplify electromagnetic energy scattered by artifacts of interest in the sample.

111. A system according to claim 110 wherein the amplification does not substantially degrade a signal to noise ratio for the electromagnetic energy scattered by the artifacts of interest in the sample.

112. A system according to claim 105 further comprising a Fourier filtering system for selectively blocking light at or near an aperture stop of the optical imaging system.

113. A system according to claim 112 wherein light is blocked by the Fourier filtering system in two orthogonal directions corresponding to a type of noise-generating electromagnetic energy scattered from the sample.

114. A system according to claim 105 wherein the system is used for one or more applications selected from the group consisting of: detection of defects in densely-patterned, sparsely-patterned or bare semiconductor wafers, reticles, crystal or glass substrates, nano structures, or biological samples; defect review; high resolution measurement of surface topology; high-contrast imaging; phase-contrast imaging; and overlay error measurement.

115. A method of using common-path interferometry to observe a sample, the method comprising:

directing electromagnetic energy toward the sample;

collecting with an optical imaging system from the sample a scattered component of the electromagnetic energy that is predominantly scattered by the sample, and a specular component of the electromagnetic energy that is predominantly undiffracted by the sample;

adjusting a relative phase of the scattered component and the specular component using a variable phase controlling system so as to improve observation of the sample; and sensing at least portions of the scattered component and specular component after said phase adjustment.

116. A method according to claim 115 wherein said adjusting the relative phase occurs at or near an aperture stop of the optical imaging system.

117. A method according to claim 115 further comprising comparing the sensed portions of scattered and specular components with reference information.

118. A method according to claim 115 wherein the relative phase is primarily adjusted by adjusting a phase of the specular component relative to a phase of the scattered component.

119. A method according to claim 115 further comprising adjustably attenuating the specular component.

120. A method according to claim 119 wherein the specular component is attenuated so as to increase image contrast.

121. A method according to claim 115 wherein the specular component is used to amplify electromagnetic energy scattered by artifacts of interest in the sample.

122. A method according to claim 121 wherein the amplification does not substantially degrade a signal to noise ratio for the electromagnetic energy scattered by the artifacts in the sample.

123. A method according to claim 115 further comprising changing a polarization of the specular component so as to maximize a signal-to-noise ratio of electromagnetic energy scattered by defects in the sample.

124. A method according to claim 115 wherein the electromagnetic energy is substantially coherent and is predominantly of a first wavelength.

125. A method according to claim 115 wherein the electromagnetic energy is generated using a laser.

126. A method according to claim 125 wherein the sample is illuminated coherently by the electromagnetic energy.

127. A method according to claim 125 wherein the electromagnetic energy is substantially is predominantly of a first wavelength, and the method further comprising:

directing electromagnetic energy of predominantly a second wavelength toward the sample, wherein the sample is illuminated coherently by the electromagnetic energy of the first wavelength and the second wavelength; and sensing at least portions of a scattered component and specular component of the electromagnetic energy from the sample of the second wavelength.

128. A method according to claim 115 further comprising selectively blocking light at or near an aperture stop of the optical imaging system so as to provide Fourier filtering capability.

129. A method according to claim 115 wherein the system is used for one or more applications selected from the group consisting of: detection of defects in densely-patterned, sparsely-patterned or bare semiconductor wafers, reticles, crystal or glass substrates, nano structures, or biological samples; defect review; high resolution measurement of surface topology; high-contrast imaging; phase-contrast imaging; and overlay error measurement.

* * * * *